(12) United States Patent
Smigocki et al.

(10) Patent No.: US 10,415,051 B2
(45) Date of Patent: Sep. 17, 2019

(54) GENETICALLY ALTERED PLANTS PRODUCING FATTY ACIDS

(71) Applicants: The United States of America, as represented by the Secretary of Agriculture, Washington, DC (US); Audacious Energy, LLC, Glastonbury, CT (US)

(72) Inventors: Anna C. Smigocki, Silver Spring, MD (US); Robert Edward Bruccoleri, Glastonbury, CT (US)

(73) Assignees: The United States of America, as Represented by the Secretary of Agriculture, Washignton, DC (US); Audacious Energy, LLC, Glastonbury, CT (US)

( * ) Notice: Subject to any disclaimer, the term of this patent is extended or adjusted under 35 U.S.C. 154(b) by 193 days.

(21) Appl. No.: 15/226,106

(22) Filed: Aug. 2, 2016

(65) Prior Publication Data

US 2017/0037420 A1 Feb. 9, 2017

Related U.S. Application Data

(60) Provisional application No. 62/201,005, filed on Aug. 4, 2015.

(51) Int. Cl.
 C12N 15/82 (2006.01)
(52) U.S. Cl.
 CPC ...... *C12N 15/8247* (2013.01); *C12N 15/8286* (2013.01); *Y02A 40/162* (2018.01)
(58) Field of Classification Search
 None
 See application file for complete search history.

(56) References Cited

U.S. PATENT DOCUMENTS

| 7,230,160 | B2 | 6/2007 | Benning | |
|---|---|---|---|---|
| 2010/0257639 | A1 | 10/2010 | Bruccoleri | |
| 2011/0162103 | A1* | 6/2011 | Hartel | C07K 14/415 800/281 |
| 2013/0247451 | A1* | 9/2013 | Vanhercke | C07K 14/415 44/388 |

OTHER PUBLICATIONS

Baud et al (Role of Wrinkled1 in the transcriptional regulation of glycolytic and fatty acid biosynthetic genes in *Arabidopsis*. The Plant Journal. 60, 933-947, 2009).*
Dohm et al (The genome of the recently domesticated crop plant sugar beet (*Beta vulgaris*). Nature. 505, 546-549, Jan. 2014).*
Andrianov, Vyacheslav, et al. "Tobacco as a production platform for biofuel: overexpression of *Arabidopsis* DGAT and LEC2 gene increases accumulation and shifts the composition of lipids in green biomass", (2010), Plant Biotechnology Journal 8:277-187.
Cernac, Alex, et al. "Wrinkled1 encodes an AP2/EREB domain protein involved in the control of storage compound biosynthesis in *Arabidopsis*", (2004), The Plant Journal, 40:575-585.
Davis, E. L., et al. "Nematicidal Activity of Fatty Acid Esters on Soybean Cyst and Root-knot Nematodes1", (1997), Supplement to the Journal of Nematology 29(4S):677-684.
Ivic-Haymes, Snezana D., et al. "Identification of Highly Regenerative Plants Within Sugar Beet (*Beta vulgaris* L.) Breeding Lines for Molecular Breeding", (2005), In Vitro Cell, Dev. Biol.—Plant, 41: 483-488.
Mendoza, Monica Santos, et al. "Leafy Cotyledon 2 activiation is sufficient to trigger the accumulation of oil and seed specific mRNAs in *Arabidopsis* leaves", (2005), FEBS Letters, 579:4666-4670.
Mu, Jinye, et al., "Leafy Cotyledon1 is a Key Regulator of Fatty Acid Biosynthesis in *Arabidopsis* 1 (C][W][OA]", (2008), Plant Physiology 148:1042-1054.
Oltmanns, Heiko, et al., "Taproot promoters cause tissue specific gen expression within the storage root of sugar beet", (2006), Planta 224:485-495.
Panella, L.W., et al. "Registration of Annual O-Type ad CMS Sugarbeet Germplasm Lines FC404 and FC404CMS", (1995), Crop Sci., 35:1721.
Smigocki, A.C., et al. "Low efficiency processing of an insectitcidal Nicotianna proteinase inhibitor precursor in Beta vulgaris hairy roots", (2009), Plant Cell Organ Cult, 97:167-174.
Zale, Janice et al., "Metabolic engineering of sugarcane to accumulate energy-dense triacylglycerols in vegetative biomass", (2016) Plant Boitechnology Journal 14:661-669.
Adhikari, Neil D. et al, "Wrinkled1 Rescues Feedback Inhibition of Fatty Acid Synthesis in Hydroxylase-Expressing Seeds", (2016), Plant Physiology 171:179-191.
Desoignies, Nicolas and Legreve, Anne, "In Vitro Dual Culture of Polymyxa betae in Agrobacterium rhizogenes Transformed Sugar Beet Hairy Roots in Liquid Media", (2011), J. Eukaryotic Microbiology 58(5):424-425.
Gryson, N. et al., "Detection of DNA During the Refining of Soybean Oil", (2002), JAOCS 79(2):171-174.
Lee, Kyeong-Ryeol et al., "Current progress towards the metabolic engineering of plant seed oil for hydroxy fatty acids production", (2015), Plant Cell Rep 34:603-615.
Pavli, Ourania I. et al., "The hrpZ Gene of *Pseudomonas syringae* pv. phaseolicola Enhances Resistance to Rhizomania Disease in Transgenic Nicotiana benthamiana and Sugar Beet", (2011) Plos One 6(3):e17306, 9 pgs.
Pavli, Ourania I. et al., "BNYVV-derived dsRNA confers resistance to rhizomania disease of sugar beet as evidenced by a novel transgenic hairy root approach", (2010)Transgenic Res 19:915-922.
Rahman, Laiq ur et al., "HCHL expression in hairy roots of Beta vulgaris yields a high accumulation of p-hydroxybenzoic acid (pHBA) glucose ester, and linkage of pHBA into cell walls", (2009) Bioresource Technology 100:4836-4842.
Ricano-Rodriguez, Jorge et al., "Plant gene co-suppression; basis of the molecular machinery of interfering RNA", (2016), Plant Omics Journal 9(4):261-269.

(Continued)

*Primary Examiner* — Medina A Ibrahim
*Assistant Examiner* — Wayne Zhong
(74) *Attorney, Agent, or Firm* — John Fado; Ariel Atkinson

(57) ABSTRACT

Methods and compositions for genetically altered plants that produce higher amounts of at least one fatty acid compared to the amount of the fatty acid produced by a wild-type plant are provided. The genetically altered plant can be a root crop plant (e.g., sugar beet) or *Nicotiana* spp., or any dicot.

27 Claims, 13 Drawing Sheets

Specification includes a Sequence Listing.

(56) References Cited

OTHER PUBLICATIONS

Shadmehr, Atena et al., "Study of Sugar Beet Cyst Nematode Life Cycle Using Plant Tissue Culture Method", (2007), Pakistan Journal of Biological Sciences 10(17):2910-2914.
Singh, Pooja et al., "Vanillin production in metabolically engineered Beta vulgaris hairy roots through heterologous expression of Pseudomonas fluorescens HCHL gene", (2015) Industrial Crops and Products 74:839-848.
Smigocki, Ann C. et al., "A Sugarbeet Root Maggot (*Tetanops myopaeformis Röder*) Bioassay Using *Beta vulgaris* L. Seedlings and In vitro Propagated Transformed Hairy Roots", (Jan.-Jun. 2006), Journal of Sugar Beet Research 43(No. 1&2).
Xu, Changcheng and Shanklin, John, "Triacylglycerol Metabolism, Function, and Accumulation in Plant Vegetative Tissues", (2016), Annu. Rev. Plant Biol. 67:179-206.

\* cited by examiner

GENETICALLY ALTERED PLANTS PRODUCING FATTY ACIDS

CROSS-REFERENCE TO RELATED APPLICATIONS

This application claims the benefit under 35 U.S.C. § 119(e) to U.S. Patent Application 62/201,005 filed on Aug. 4, 2015, the contents of which are incorporated herein by reference in its entirety.

BACKGROUND OF THE INVENTION

Field of Invention

The present invention relates to methods and compositions for increasing production of fatty acids in genetically altered sugar beet, other root crops, and/or *Nicotiana* spp. More specifically, the present invention relates to genetically altered sugar beet, other root crops, and/or *Nicotiana* spp. plants that express increased levels of one or more transcription factors and/or diacylglycerol O-acyltransferase 1 to produce higher amounts of at least one fatty acids (compared to levels of the fatty acid(s) in wild-type/non-modified plants) which are useful as a feedstock for production of biofuels; and the methods of generating these genetically altered plants. These genetically altered plants also have enhanced resistance to insects that feed on the genetically altered plant.

Brief Description of the Prior Art

Global warming, fossil fuel depletion, and the growth of worldwide energy consumption are major issues facing the $21^{st}$ century. Governments and companies worldwide have been searching for solutions to these problems, in particular searching for approaches to increasing production of alternative fuels. Using corn to produce ethanol is one approach to producing an alternative fuel. Another method uses enzymes to increase the breakdown of cellulose for conversion to ethanol.

Currently, crops cannot be used to produce sufficient fuel to meet the increasing worldwide demand because of a lack of optimization for fuel production. For example, corn ethanol uses a small fraction of the total corn plant mass for fuel, and significant energy losses are incurred by the fermentation and distillation processes. In contrast, plant fats (also referred to as oils, fatty acids, and/or lipids) are chemically much more similar to crude oil. Most plant fats are long chain hydrocarbons (approximately 16 carbons) with a carboxylic acid group at one end. A primary difference between plant hydrocarbons and crude oil are the carboxylic acid groups present in plant hydrocarbons. Further, plant fats are already commercialized by the biodiesel industry which converts cooking oils (e.g., soybean, canola, sunflower, peanut) into fuel via chemistry. The cooking oils are fatty acids containing glycerin. The biodiesel processor performs a transesterification reaction which removes the glycerin and replaces it with an ethyl ester. These esters can be used instead of diesel fuel. However, the amount of hydrocarbons in various plants are not sufficiently high enough for commercially viable use of plant hydrocarbons as a complete replacement of fossil fuel hydrocarbons. Thus, a need exists for plants that can produce higher quantities of oils.

Interestingly, Andrianov, et al. (*Plant Biotech. J.* 8:277-287 (2010)) describes generating genetically altered *Nicotiana tabacum* cv. Wisconsin-38 and *N. tabacum* cv. NC-55 with DNA encoding *Arabidopsis thaliana* diacylglycerol O-acyltransferase 1 (Dgat or Tag1) under control of ribulose-1,5-bisphosphate carboxylase promoter (ssRBCS, a tissue-specific, inducible promoter) and with DNA encoding *Arabidopsis thaliana* leafy cotyledon 2 (Lec2) under control of AlcA, an inducible promoter. They then determined that these genetically altered plants produced higher amounts of fatty acids compared to wild-type plants (up to 5.6% fatty acids per dry biomass in their genetically altered tobacco compared to 2.8-4% fatty acids per dry biomass in wild-type plants). While the transgenic plants in Andrianov, et al. (2010) produced some higher levels of fatty acids (in particular, oleic acid), the genetically altered plants had dramatically lower amounts of linolenate acid compared to wild-type plants (from 67% of fatty acids in wild type plants to ~35% of fatty acids in genetically altered tobacco plants). Linolenate acid is a major component of fatty acids in wild-type plants. In contrast to Andrianov, et al. (2010), the genetically altered plants described herein produce higher amounts of linolenic acid than achieved by Andrianov, et al. (2010), and higher percentage of fatty acids per dry biomass compared to Andrianov, et al. (2010); a surprising result. In addition, the genetically altered plants described herein also produced higher amounts of palmitic acid, linoleic acid, and palmitoleic acid than wild-type plants. Andrianov, et al. (2010) did not report the levels of palmitic acid, palmitoleic acid, nor linoleic acid produced by their *N. tabacum* plants transformed with either AtLec2 or AtTag1, possibly because their plants did not produce increased amounts of these fatty acids compared to the amount produced by wild-type plants.

SUMMARY OF THE INVENTION

It is an object of this invention to have a method for increasing the amount of at least one fatty acid produced in a genetically altered plant (or part thereof) compared to the amount of the at least one fatty acid produced in a wild-type plant (or part thereof). It is a further object of this invention that the method involves transforming a wild-type plant cell with an expression cassette (or vector) encoding a heterologous promoter operably linked to a polynucleotide encoding at least one fatty acid biosynthesis protein to generate a transformed plant cell, and culturing the transformed plant cell to produce the genetically altered plant (or part thereof) such that the genetically altered plant produces the at least one fatty acid biosynthesis protein and produces a higher amount of at least one fatty acid compared to the amount of at least one fatty acid produced by the wild-type plant. It is another object of this invention that the fatty acid biosynthesis protein can be BvLec1, BvLec2/Fusca3, BvWri1, BvTag1, AtLec1, AtLec2, AtWri1, or a combination thereof and that the heterologous promoter is a constitutive promoter or a tissue-specific promoter, but not ssRBCS. It is a further object of this invention that the genetically altered plant can be a root crop plant (e.g., sugar beet, carrot, potato, etc.) or *Nicotiana* spp. In an alternative embodiment, when the genetically altered plant is *N. tabacum*, the fatty acid biosynthesis protein is not AtLec2. It is another object of this invention that the heterologous promoter in the expression vector (cassette) is CaMV 35S promoter, a BvSTI promoter, or Bv major latex-like protein promoter. It is another object of this invention that the least one fatty acid can be linolenic acid, linoleic acid, palmitic acid, palmitoleic acid, oleic acid, or a combination thereof.

It is another object of the method described above that BvLec1 has the amino acid sequence of SEQ ID NO: 6 or a sequence at least 95% identical thereof, that BvLec2/Fusca3 has the amino acid sequence of SEQ ID NO: 7 or a sequence at least 95% identical thereof, that BvWri1 has the amino acid sequence of SEQ ID NO: 8 or a sequence at least 95% identical thereof, that BvTag1 has the amino acid sequence of SEQ ID NO: 9 or a sequence at least 95% identical thereof, that AtLec1 has the amino acid sequence of SEQ ID NO: 14, that AtLec2 has the amino acid sequence of SEQ ID NO: 15, and that AtWri1 has the amino acid sequence of SEQ ID NO: 16. It is an alternative object of the above described invention that BvLec1 is encoded by the DNA sequence of SEQ ID NO: 2 or a sequence at least 90% identical thereof, that BvLec2/Fusca3 is encoded by the DNA sequence of SEQ ID NO: 3 or a sequence at least 90% identical thereof, that BvWri1 is encoded by the DNA sequence of SEQ ID NO: 4 or a sequence at least 90% identical thereof, that BvTag1 is encoded by the DNA sequence of SEQ ID NO: 5 or a sequence at least 90% identical thereof, that AtLec1 is encoded by the DNA sequence of SEQ ID NO: 11, that AtLec2 is encoded by the DNA sequence of SEQ ID NO: 12, and that AtWri1 is encoded by the DNA sequence of SEQ ID NO: 13.

It is another object of this invention to have a genetically altered plant (or part thereof or progeny thereof) produced by the above described method, such that the genetically altered plant (or part thereof or progeny thereof) produces a higher amount of at least one fatty acid compared to the amount of the at least one fatty acid produced by a wild-type plant. It is another object of this invention that the genetically altered plant is a root crop plant (e.g., sugar beet, carrot, potato, etc.) or *Nicotiana* spp. In an alternative embodiment of this invention, when the genetically altered plant is *N. tabacum*, then the fatty acid biosynthesis protein is not AtLec2. It is another object of this invention that the heterologous promoter in the expression cassette or vector is CaMV 35S promoter, a BvSTI promoter, and By major latex-like protein promoter. It is a further object of this invention that the at least one fatty acid can be linolenic acid, linoleic acid, palmitic acid, palmitoleic acid, oleic acid, or a combination thereof. It is another object of this invention to have a cell, a pollen, an ovary, a flower, a seed, a leaf, a root, a stem, and a protoplasm, etc., of this genetically altered plant.

An object of this invention is to have a genetically altered plant (or part thereof) that produces a higher amount of at least one fatty acid compared to the amount of the at least one fatty acid produced by a wild-type plant (or part thereof). It is a further object of this invention that the genetically altered plant (or part thereof) contains an expression cassette which contains a heterologous promoter operably linked a polynucleotide that encodes at least one fatty acid biosynthesis protein, such that the at least one fatty acid biosynthesis protein can be BvLec1, BvLec2/*Fusca*3, BvWri1, BvTag1, AtLec1, AtLec2, AtWri1, or a combination thereof. It is a further object of this invention that the genetically altered plant (or part thereof) produces the at least one fatty acid biosynthesis protein encoded by the polynucleotide, and that the produced at least one fatty acid biosynthesis protein increases the production of at least one fatty acid in the genetically altered plant (or part thereof) compared to the amount of the at least one fatty acid produced by said wild-type plant (or part thereof). In one embodiment of this invention, the heterologous promoter in the expression cassette (or vector) in the genetically altered plant (or part thereof) is a constitutive promoter or a tissue-specific promoter. In an alternative embodiment, the heterologous promoter in the expression cassette (or vector) is not ssRBCS. In another alternative embodiment, the heterologous promoter is CaMV 35S promoter, a BvSTI promoter, or By major latex-like protein promoter. It is an object of this invention that the genetically altered plant (or part thereof) produces higher amounts of linolenic acid, linoleic acid, palmitic acid, palmitoleic acid, oleic acid, or a combination thereof. It is another object of this invention that the part of the genetically altered plant includes, but is not limited to, a cell, a pollen, an ovary, a flower, a seed, a leaf, a root, a stem, and a protoplasm. It is another object of this invention that the genetically altered plant (or part thereof) is a root crop plant (e.g., sugar beet, carrot, potato, etc.) or *Nicotiana* spp. In an alternative embodiment of this invention, when the genetically altered plant is *N. tabacum*, then the fatty acid biosynthesis protein is not AtLec2. A further object of this invention is to have progeny of the genetically altered plant or parts thereof.

It is another object of the genetically altered plant (or part thereof or progeny) described above that BvLec1 has the amino acid sequence of SEQ ID NO: 6 or a sequence at least 95% identical thereof, that BvLec2/Fusca3 has the amino acid sequence of SEQ ID NO: 7 or a sequence at least 95% identical thereof, that BvWri1 has the amino acid sequence of SEQ ID NO: 8 or a sequence at least 95% identical thereof, that BvTag1 has the amino acid sequence of SEQ ID NO: 9 or a sequence at least 95% identical thereof, that AtLec1 has the amino acid sequence of SEQ ID NO: 14, that AtLec2 has the amino acid sequence of SEQ ID NO: 15, and that AtWri1 has the amino acid sequence of SEQ ID NO: 16. It is an alternative object of the above described invention that BvLec1 is encoded by the DNA sequence of SEQ ID NO: 2 or a sequence at least 90% identical thereof, that BvLec2/Fusca3 is encoded by the DNA sequence of SEQ ID NO: 3 or a sequence at least 90% identical thereof, that BvWri1 is encoded by the DNA sequence of SEQ ID NO: 4 or a sequence at least 90% identical thereof, that BvTag1 is encoded by the DNA sequence of SEQ ID NO: 5 or a sequence at least 90% identical thereof, that AtLec1 is encoded by the DNA sequence of SEQ ID NO: 11, that AtLec2 is encoded by the DNA sequence of SEQ ID NO: 12, and that AtWri1 is encoded by the DNA sequence of SEQ ID NO: 13.

It is an object of this invention to have a method for increasing a genetically altered plant's resistance to an insect that feeds on the genetically altered plant (or part thereof) compared to a wild-type plant's resistance to the insect feeding on the wild-type plant (or part thereof). It is another object of this invention that the method involves transforming a wild-type plant cell with an expression cassette (or vector) encoding a heterologous promoter operably linked to a polynucleotide encoding at least one fatty acid biosynthesis protein to generate a transformed plant cell, and culturing the transformed plant cell to develop the genetically altered plant (or part thereof) such that the genetically altered plant produces at least one fatty acid biosynthesis protein, and the genetically altered plant produces at least one fatty acid in an amount higher than the amount produced by the wild-type plant. It is a further object of this invention that the higher amount of the at least one fatty acid in the genetically altered plant increases that genetically altered plant's resistance to the insect compared to the wild-type plant's resistance to the insect. It is yet another object of this invention that the one fatty acid biosynthesis protein can be BvLec1, BvLec2/*Fusca*3, BvWri1, BvTag1, AtLec1, AtLec2, AtWri1, or a combination thereof. It is another object of this invention that the genetically altered plant (or part thereof) is a root crop plant (e.g., sugar beet, carrot, potato, etc.) or *Nicotiana* spp. In an alternative embodiment of this invention, when the genetically altered plant is *N. tabacum*, then the fatty acid biosynthesis protein is not AtLec2. It is another object of this invention that the heterologous promoter can be a constitutive promoter or a tissue-specific promoter. In an alternative embodiment, the tissue-specific promoter is not ssRBCS. In yet another embodiment, the heterologous promoter can be CaMV 35S promoter, a BvSTI promoter, or By major latex-like protein promoter. It is another object of this invention that the part of the genetically altered plant includes, but is not limited to, a cell, a pollen, an ovary, a flower, a seed, a leaf, a root, a stem, and a protoplasm. It is another object of this invention that the fatty acid is linolenic acid, linoleic acid, palmitic acid, palmitoleic acid, oleic acid, or a combination thereof.

It is another object of the method described above concerning increasing a genetically altered plant's resistance to an insect that BvLec1 has the amino acid sequence of SEQ ID NO: 6 or a sequence at least 95% identical thereof, that BvLec2/Fusca3 has the amino acid sequence of SEQ ID NO: 7 or a sequence at least 95% identical thereof, that BvWri1 has the amino acid sequence of SEQ ID NO: 8 or a sequence at least 95% identical thereof, that BvTag1 has the amino acid sequence of SEQ ID NO: 9 or a sequence at least 95% identical thereof, that AtLec1 has the amino acid sequence of SEQ ID NO: 14, that AtLec2 has the amino acid sequence of SEQ ID NO: 15, and that AtWri1 has the amino acid sequence of SEQ ID NO: 16. It is an alternative object of the above described invention that BvLec1 is encoded by the DNA sequence of SEQ ID NO: 2 or a sequence at least 90% identical thereof, that BvLec2/Fusca3 is encoded by the DNA sequence of SEQ ID NO: 3 or a sequence at least 90% identical thereof, that BvWri1 is encoded by the DNA sequence of SEQ ID NO: 4 or a sequence at least 90% identical thereof, that BvTag1 is encoded by the DNA sequence of SEQ ID NO: 5 or a sequence at least 90% identical thereof, that AtLec1 is encoded by the DNA sequence of SEQ ID NO: 11, that AtLec2 is encoded by the DNA sequence of SEQ ID NO: 12, and that AtWri1 is encoded by the DNA sequence of SEQ ID NO: 13.

BRIEF DESCRIPTION OF THE DRAWINGS

In FIG. 3, "BvL2/F3" means BvLec2/Fusca3, and "blank" means an empty expression cassette.

In FIG. 4, "BvL2/F3" means BvLec2/Fusca3, and "blank" means an empty expression cassette.

In FIG. 5, "BvL2/F3" means BvLec2/Fusca3, and "blank" means an empty expression cassette.

In FIG. 6, "BvL2/F3" means BvLec2/Fusca3, and "blank" means an empty expression cassette.

In FIG. 7, "BvL2/F3" means BvLec2/Fusca3, and "blank" means an empty expression cassette.

In FIG. 8, "BvL2/F3" means BvLec2/Fusca3, and "blank" means an empty expression cassette.

In FIG. 9, "BvL2/F3" means BvLec2/Fusca3, and "blank" means an empty expression cassette.

In FIG. 10, "BvL2/F3" means BvLec2/Fusca3, and "blank" means an empty expression cassette.

In FIG. 11, "BvL2/F3" means BvLec2/Fusca3, and "blank" means an empty expression cassette.

In FIG. 12, "BvL2/F3" means BvLec2/Fusca3, and "blank" means an empty expression cassette.

In FIG. 13, "BvL2/F3" means BvLec2/Fusca3, and "blank" means an empty expression cassette.

DETAILED DESCRIPTION OF THE INVENTION

Figure 1:
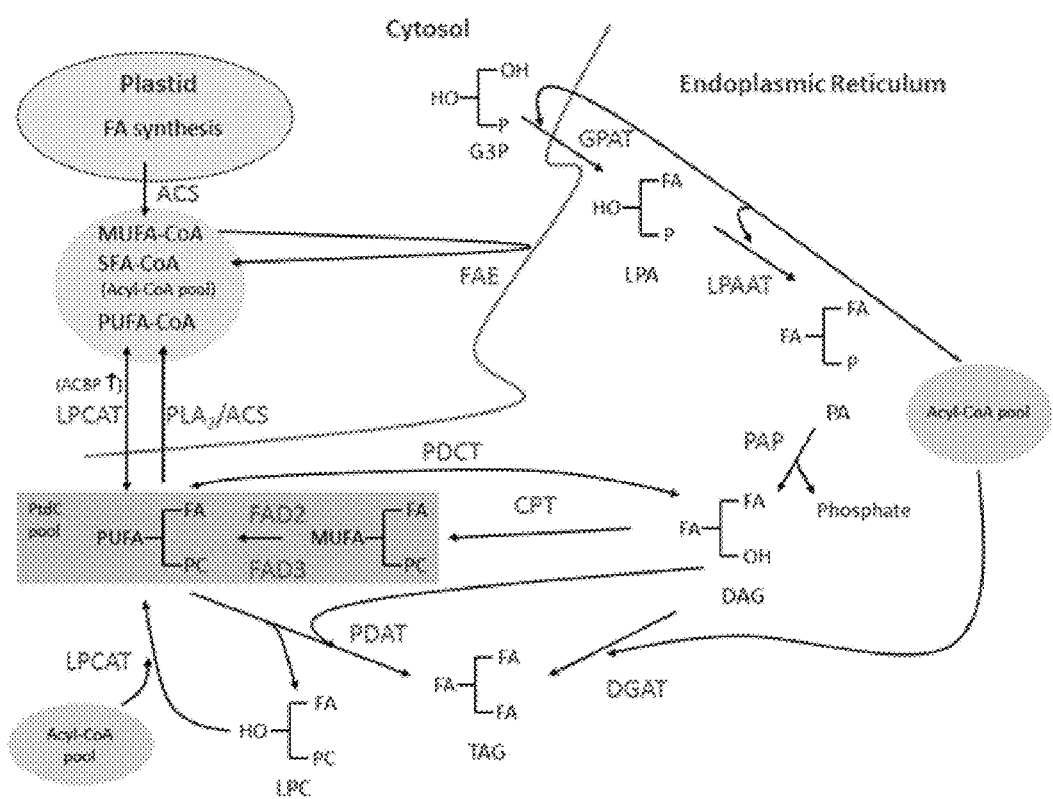
FIG. 1 illustrates the triacylglycerol biosynthetic pathway. Information about the abbreviations is provided infra.

A need exists for genetically altered plants that produce sufficiently high quantities of oils so that it becomes commercially viable to grow such plants and harvest that oil for use instead of hydrocarbon oils. As such, genetically altered plants described herein solve this need. One genetically altered plant described herein (Nicotiana) is not a food-source for animals nor humans, and, thus, the use of it in this manner does not reduce the amount of food available for consumption. The other genetically altered plant described herein (Beta vulgaris) is a food source for animals and humans, but such usage has decreased with time. Thus, the use of this genetically altered plant in this manner will not adversely impact the food supply.

One of the genetically altered plants described herein is sugar beet. These genetically altered sugar beets produce vegetable oil in their roots and could possibly significantly improve the agricultural practice of fattening livestock prior to slaughter. Commonly, livestock for meat are initially grown in pastoral settings. When they reach an appropriate size, the animals are transferred to a feed lot, where they are fed a high energy density (i.e., grains), at least compared to the pastoral diet, and their mobility is reduced, thereby reducing their caloric expenditures. As a result, the animals become fat. This fattening process improves the tenderness of the meat, and increases its market value.

The genetically altered sugar beets described herein could be a more efficient source of food for fattening compared to grains because the number of calories per acre of feed is much larger. Assuming a yield of approximately 7000 pounds per acre of vegetable oil from beets versus approximately 151 bushels per acre of corn, the total caloric yield would be 28 million food calories for genetically altered sugar beets versus 18.5 million food calories for corn. In addition, the animals would be able to store the fats from the genetically altered sugar beets directly with less metabolism compared to the metabolism of sugars and starches which require biochemical energy to convert them into fats.

The other genetically altered plant described is tobacco, and more specifically N. benthamiana. With the reduction of tobacco usage in cigarettes and other smoking products, the genetically altered tobacco described herein can provide an alternative usage for this crop. Many tobacco farmers would welcome an alternative market for tobacco.

The genetically altered plants contain one or more expression cassettes containing DNA that encodes one or more proteins obtained from Beta vulgaris (sugar beet; abbreviated as Three of these proteins, named Lec1, Lec2/Fusca3, and Wri1, are transcription factors that increase the transcriptional activity of genes involved the plant's oil biosynthetic pathway. The fourth protein, diacylglycerol O-acyltransferase 1 (Tag1), is an enzyme involved in the plant's oil biosynthetic pathway. Also described herein are the transcription factors Lec1, Lec2, and Wri1 obtained from Arabidopsis thaliana (abbreviated as "At"). Table 1, infra, lists the sequence identification number of the proteins and genes involved in this invention.

TABLE 1

| Gene or Protein (GenBank Access. No.) | Sequence ID Number |
|---|---|
| Bv major latex-like protein promoter (GenBank AX449164) | SEQ ID NO: 1 |
| BvLec1 (DNA) | SEQ ID NO: 2 |
| BvLec2/Fusca3 (DNA) | SEQ ID NO: 3 |
| BvWri1 (DNA) | SEQ ID NO: 4 |
| BvTag1 (DNA) | SEQ ID NO: 5 |
| BvLec1 (amino acid) | SEQ ID NO: 6 |
| BvLec2/Fusca3 (amino acid) | SEQ ID NO: 7 |
| BvWri1 (amino acid) | SEQ ID NO: 8 |
| BvTag1 (amino acid) | SEQ ID NO: 9 |
| BvSTI promoter from Beta vulgaris strain 1016 | SEQ ID NO: 10 |
| AtLec1 (DNA) | SEQ ID NO: 11 |
| AtLec2 (DNA) (GenBank AT3G54320.3) | SEQ ID NO: 12 |
| AtWri1 (DNA) | SEQ ID NO: 13 |
| AtLec1 (amino acid) | SEQ ID NO: 14 |
| AtLec2 (amino acid) | SEQ ID NO: 15 |
| AtWri1 (amino acid) | SEQ ID NO: 16 |
| CaMV 35S promoter (GenBank AF234297.1) | SEQ ID NO: 35 |

Because this invention involves production of genetically altered plants and using recombinant DNA techniques, the following definitions are provided to assist in describing this invention. The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein that gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The terms "approximately" and "about" refers to a quantity, level, value or amount that varies by as much as 30% in one embodiment, or in another embodiment by as much as 20%, in a third embodiment by as much as 10%, or in a fourth embodiment by as much as 5% to a reference quantity, level, value or amount. As used herein, the singular form "a", "an", and "the" include plural references unless the context clearly dictates otherwise. For example, the term "a bacterium" includes both a single bacterium and a plurality of bacteria.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

For nucleic acids, sizes are given in either kilobases (kb) or base pairs (bp). Estimates are typically derived from agarose or polyacrylamide gel electrophoresis, from sequenced nucleic acids, or from published DNA sequences. For proteins, sizes are given in kilodaltons (kDa or KDa) or amino acid residue numbers. Proteins sizes are estimated from gel electrophoresis, from sequenced proteins, from derived amino acid sequences, or from published protein sequences. A nucleotide can be referred to as "nt".

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98(1994)). Because of the degeneracy of nucleic acid codons, one can use various different polynucleotides to encode identical polypeptides. Table 2, infra, contains information about which nucleic acid codons encode which amino acids.

TABLE 2

| Amino acid | Nucleic acid codons |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |

In addition to the degenerate nature of the nucleotide codons which encode amino acids, alterations in a polynucleotide that result in the production of a chemically equivalent amino acid at a given site, but do not affect the functional properties of the encoded polypeptide, are well known in the art. "Conservative amino acid substitutions" are those substitutions that are predicted to interfere least with the properties of the reference polypeptide. In other words, conservative amino acid substitutions substantially conserve the structure and the function of the reference protein. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide. Table 3 provides a list of exemplary conservative amino acid substitutions. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

TABLE 3

| Amino Acid | Conservative Substitute |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Ile, Leu |
| Phe | His, Leu, Met, Trp, Tyr |
| Ser | Cys, Thr |
| Thr | Ser, Val |
| Trp | Phe, Tyr |
| Tyr | His, Phe, Trp |
| Val | Ile, Leu, Thr |

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native polyacrylamide gel electrophoresis or by anion-exchange HPLC as described in Pearson & Reanier, *J. Chrom.* 255: 137-149 (1983).

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant or wild-type) form of the cell or express native genes that are otherwise abnormally expressed—over-expressed, under-expressed or not expressed at all.

The terms "transgenic", "transformed", "transformation", and "transfection" are similar in meaning to "recombinant". "Transformation", "transgenic", and "transfection" refer to the transfer of a polynucleotide (usually a heterologous polynucleotide) into the genome of a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host's chromosome remain as an expression vector within the cell. One may need to grow the cell under certain growth or environmental conditions (e.g., using a selection agent or marker) in order for the expression vector or cassette to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants", as well as recombinant organisms or cells.

A genetically altered organism is any organism with any changes to its genetic material, whether in the nucleus or cytoplasm (organelle). A genetically altered organism can be a recombinant or transformed organism and its progeny (i.e., containing an expression vector or cassette encoding a desired protein or RNA). A genetically altered organism can also be an organism that was subjected to one or more mutagens that resulted in at least one change in its DNA caused by the mutagen(s) or its progeny. Also, an organism that has been bred to incorporate a mutation or alteration into its genetic material, as compared to the wild-type organism, is a genetically altered organism. For the purposes of this invention, the organism can be a fungi, bacteria, insect cell lines, etc.

An "expression vector" or simply a "vector" is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette". In contrast, as described in the examples herein, a "cassette" or "expression cassette" is a polynucleotide containing a section of an expression vector of this invention. The use of the cassettes assists in the assembly of the expression vectors and can contain a promoter operably linked to a polynucleotide encoding the protein of interest. An expression vector is a replicon, such as plasmid, phage, virus, chimeric virus, or cosmid, and which contains the desired polynucleotide sequence operably linked to the expression control sequence(s). Expression vectors contain a promoter operably linked to the polynucleotide encoding the protein of interest. Usually, the promoter and the polynucleotide encoding the protein of interest are heterologous to each other.

As used herein, the term "promoter" refers to a polynucleotide that, in its native state, is located upstream or 5' to a translational start codon of an open reading frame (or protein-coding region) and that is involved in recognition and binding of RNA polymerase and other proteins (trans-acting transcription factors) to initiate transcription. A "plant promoter" is a native or non-native promoter that is functional in plant cells. Some promoters described herein are predominately functional in cells of specific tissue and thus are considered "tissue-specific promoters". Other promoters described herein are active in all tissue at all times and are referred to as constitutive promoters. A plant promoter can be used as a 5' regulatory element for modulating expression of a particular desired polynucleotide operably linked thereto. When the promoter sequence is not naturally operably linked to the desired polynucleotide, the promoter or the desired polynucleotide are considered heterologous to each other. Thus, one can refer to the promoter as a heterologous promoter or to the desired polynucleotide as a heterologous polynucleotide. When operably linked to a heterologous polynucleotide, a promoter typically causes the heterologous polynucleotide to be transcribed in a manner that is similar to that of which the promoter is normally associated. In this invention, the promoters and polynucleotides encoding the proteins are heterologous to each other, even though at least one promoter exists in one of the indicated plants and the proteins encoded by the desired polynucleotides exist in that indicated plant(s).

In certain embodiments of the present invention, the expression vectors or cassettes described herein contain an inducible-promoter operably linked to the polynucleotide that encodes the protein of interest. In general, inducible promoters cause a polynucleotide to be expressed under specific conditions such as, but not limited to, in specific tissue, at specific stages of development, or in response to specific environmental conditions, e.g., wounding of tissue or presence or absence of a particular compounds. Inducible promoters for plants respond to various forms of environmental stresses, or other stimuli, including, for example, mechanical shock, heat, cold, salt, flooding, drought, salt, anoxia, pathogens, such as bacteria, fungi, and viruses, and nutritional deprivation, including deprivation during times of flowering and/or fruiting, and other forms of plant stress. For example, the promoter can be induced by one or more of the following: abiotic stresses such as wounding, cold, desiccation, ultraviolet-B (van Der Krol, et al., *Plant Physiol.* 121:1153-1162 (1999)), heat shock (Shinmyo, et al., *Biotechnol. Bioeng.* 58:329-332 (1998)) or other heat stress, drought stress, or water stress. The promoter may further be one induced by biotic stresses, including pathogen stress, such as stress induced by a virus (Sohal, et al., *Plant Mol. Biol.* 41:75-87 (1999)) or fungi (Eulgem, et al., *Embo J.* 18:4689-4699 (1999); Cormack, et al., *Biochim Biophys Acta* 1576:92-100 (2002)); stresses induced as part of the plant defense pathway (Lebel, et al., *Plant J.* 16:223-33 (1998)); or promoters induced by other environmental signals, such as light (Ngai, et al., *Plant J.* 12:1021-1034 (1997)), carbon dioxide (Kucho, et al., *Plant Physiol.* 121: 1329-1338 (1999); Kucho, et al., *Plant Physiol.* 133:783-7893 (2003)), hormones or other signaling molecules such as auxin, hydrogen peroxide and salicylic acid (Chen, et al., *Plant J.* 19:667-677 (1999); Chen, et al., *Plant J.* 10:955-966 (1996)), sugars and gibberellin (Lu, et al., *J. Biol. Chem.* 273:10120-10131 (1998)) or abscisic acid and ethylene (Leubner-Metzger, et al., *Plant Mol. Biol.* 38:785-795 (1998)). Numerous examples may be found in Okamuro and Goldberg, *Biochemistry of Plants* 15:1-82 (1989).

In other embodiments of the invention, tissue-specific promoters are used in the expression vectors or cassettes. Tissue-specific expression patterns are controlled by tissue- or stage-specific promoters that include, but are not limited to, fiber-specific, green tissue-specific, root-specific, stem-specific, root-specific, and flower-specific. Examples of the utilization of tissue-specific expression include, but are not limit to, the expression in leaves of the desired peptide for the protection of plants against foliar pathogens, the expression in roots of the desired peptide for the protection of plants against root pathogens, and the expression in roots or seedlings of the desired peptide for the protection of seedlings against soil-borne pathogens. In many cases, however, protection against more than one type of pathogen may be sought, and expression in multiple tissues will be desirable. Another example of promoters that are expressed in specific tissue are chlorophyll A/B binding protein (CAB) promoter (Bansal, et al., *Proc. Natl. Acad. Sci. USA* 89(8):3654-8 (1992)), small subunit of ribulose-1,5-bisphosphate carboxylase (ssRBCS) promoter (Bansal, et al., *Proc. Natl. Acad. Sci. USA* 89(8):3654-8 (1992)), phosphoenolpyruvate carboxylase 1 (PPC1) promoter (Kausch, et al., *Plant Mol.*

*Biol.* 45(1):1-15 (2001)), a senescence activated promoter, SEE1, (Robson, et al., *Plant Biotechnol. J.* 2(2):101-12 (2004)), and the sorghum leaf primordia specific promoter, RS2, (GenBank Accession No. EI979305.1).

In other embodiments, one can use constitutive promoters to drive expression of the polynucleotides described herein. Plant constitutive promoters are well-known in the art field, and include, but are not limited to, cauliflower mosaic virus promoter (CaMV) 35S, CaMV 19S, figwort mosaic virus promoter (FMV) 35S, coat protein promoter of tobacco mosaic virus (TMV), ubiquitin promoter, opine promoter, actin 1 promoter, and alcohol dehydrogenase 1 promoter. It is recognized that because, in most cases, the exact boundaries of regulatory sequences have not been completely defined, nucleic acid fragments of different lengths may have identical promoter activity.

A transcription regulator is a protein that helps control the transcription of one or more other genes by interacting with a promoter or other upstream regulatory element. A transcription regulator may increase or "turn on" the transcription of one or more genes, or it may decrease or "turn off" the transcription of one or more genes.

The utilization of up-regulation, down-regulation, or gene silencing to change the level of expression of a gene or amount of a protein present in a genetically modified cell or organism compared to the level present in the wild-type cell or organism is referred to as "altering" the expression of the gene.

In some embodiments, one can screen for genetically altered plant cells and/or genetically altered plants that contain and express the expression cassette by including DNA encoding a selection marker (also referred to "selection agent") in the expression cassette. The gene encoding the selection marker can encode a protein that imparts resistance to an antibiotic, a herbicide, or other compound that could kill the plant cells or plant if the expression cassette is not be transcribed. The gene could also encode a non-lethal protein that acts as a selection marker such as green fluorescent protein or red fluorescent protein. In another embodiment, the gene encodes an enzyme that cleaves a compound present in the media and causes a color change or other visual change. Non-limiting examples of selection markers include genes encoding resisting to glufosinate, kanamycin, ampicillin, hygromycin, cefotaxime, carbenicilline, carbenicillin, tetracycline, ampicillin, bleomycin, streptomycin, spectinomycin, and phosphinothricin acetyltransferase; and genes encoding enzymes such as β-glucuronidase (Gus) (UidA) (see, e.g., U.S. Pat. Nos. 5,268,463, 5,432,081, 5,599,670), β-galactosidase, and luciferase (Lux) (see e.g., Ow et al., (1986) *Science,* 234: 856-859; Sheen et al., (1995) *Plant J.,* 8(5):777-784; and WO 97/41228).

"Biodiesel" refers to plant oils which have been transesterified with a short chain alcohol and which can be used directly in diesel fuel engines. "Feedstock" means a substitute for petroleum for a refinery that is economically comparable to crude oil.

Percent identity as used herein refers to the comparison of the homozygous alleles or DNA sequences. The terms "identical" or percent "identity", in the context of two or more nucleic acids or polypeptide sequences, refer to two or more sequences or subsequences that are the same or have a specified percentage of amino acid residues or nucleotides that are the same (e.g., 85% identity, 90% identity, 99%, or 100% identity), when compared and aligned for maximum correspondence over a comparison window, or designated region as measured using a sequence comparison algorithm or by manual alignment and visual inspection. Two or more polynucleotides or polypeptides are identical or have a preferred percentage of identity when the two or more sequences or sub-sequences have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, a substantial identity exists over a region of the sequences that is at least about 50 residues in length. In another exemplary embodiment, a substantial identity exists over a region of the sequences that is at least about 100 residues in length. In still another exemplary embodiment, a substantial identity exists over a region of the sequences that is at least about 150 residues or more in length. In one exemplary embodiment, the sequences are substantially identical over the entire length of the nucleic acid or protein sequence. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from about 20 to about 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., eds., *Current Protocols in Molecular Biology,* 1995 supplement).

Another example of algorithm that is suitable for determining percent sequence identity and sequence similarity are the BLAST® and BLAST® 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST® analyses is publicly available through the National Center for Biotechnology Information (ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST® algorithm parameters W, T, and X determine the sensitivity and speed of the alignment. The BLAST®N program (for nucleotide sequences) uses as defaults a word length (W) of 11, an expectation (E) or 10, M=5, N4 and a comparison of both strands. For amino acid sequences, the BLAST® P program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=4, and a comparison of both strands.

As used herein, the term "plant" includes reference to an immature or mature whole plant, including a plant from which seed, grain, anthers or pistils have been removed. A seed or embryo that will produce the plant is also considered to be the plant or part thereof.

As used herein, the term "plant part" (as in a "genetically altered plant or part thereof") includes protoplasts, leaves, stems, roots, root tips, anthers, seed, embryo, pollen, ovules, cotyledon, hypocotyls, flower, shoot, tissue, petiole, cells, meristematic cells and the like. The cambium is a layer of undifferentiated cells in a plant that divide and differentiate into other plant tissues.

Regeneration of a plant refers to the development of a plant from plant cells in tissue culture. Usually, the plant cells have been transformed with an expression vector or cassettes and selected for producing a protein encoded on that expression vector or cassette.

A root crop is any plant that uses its root, tuber, corm, rhizome, bulb, etc., as a place to store food (i.e., sugar, starch, other carbohydrates). Non-limiting examples of root crops include sugar beet, onion, garlic, potato, yams, cassava, ginger, taro, jicama, carrots, parsnips, radishes, turnips and rutabagas.

Root vasculature tissue in the plant root is responsible for carrying nutrients to and from the root. The root vascular tissue are generally tubular. In the sugar beet root or other root crops, there are specific tissues for the storage of sugar. These storage tissues are physically and visually distinct from the root vasculature.

This invention utilizes routine techniques in the field of molecular biology. Basic texts disclosing the general methods of use in this invention include Green and Sambrook, 4th ed. 2012, Cold Spring Harbor Laboratory; Kriegler, *Gene Transfer and Expression: A Laboratory Manual* (1993); and Ausubel et al., eds., *Current Protocols in Molecular Biology*, 1994—current, John Wiley & Sons. Unless otherwise noted, technical terms are used according to conventional usage. Definitions of common terms in molecular biology maybe found in e.g., Benjamin Lewin, *Genes IX*, published by Oxford University Press, 2007 (ISBN 0763740632); Krebs, et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Methods for sugar beet transformation are described in Gurel, et al., *Critical Reviews in Plant Sciences*, 27:108-140 (2008) and in Smigocki, et al. (eds.), *Compendium of Transgenic Crop Plants: Transgenic Sugar, Tuber and Fiber Crops*, Blackwell Publishing, Oxford, UK, pp 59-96 (2008).

The present invention provides methods of generating genetically altered plants, and the genetically altered plant themselves, to efficiently make high quality oil feedstocks for the petroleum industry from carbon dioxide and water using solar energy at a nearly constant cost. It is anticipated that the present invention will cost less than crude oil extracted from the earth as crude oil is consumed over the upcoming years. These genetically altered plants can also be fed to animals in feedlots. The genetically altered plants can be sugar beet plants, other root crop plants, *Nicotiana* spp. (*N. benthamiana* in one embodiment), and other dicots. These genetically altered plants may also have increased resistance to insects that feed on the genetically altered plant compared to a wild-type plant's resistance to insect feeding. The present invention also provides certain transcription regulators of fatty acid synthesis needed to generate genetically altered sugar beet plants, other root crop plants, *Nicotiana* spp., and the like to produce large quantities of fats in the root(s), leaves, and/or stems and branches of the genetically altered plant. The present invention identifies sugar beet genomic regions which contain transcripts that are expressed in the sugar storage regions of the tap root, and which can be modified to express additional genes in those regions. The present invention also covers promoters that are active in plants' roots or storage tissue and which are operably linked to the cDNA sequences of the genes described herein. Two such promoters are the major latex-like protein promoter and a BvSTI promoter. In yet another embodiment, a constitutive promoter may be operably linked to DNA encoding the transcription regulators and/or enzyme described herein.

In one embodiment of this invention, an expression vector or cassette containing the major latex-like protein promoter is operably linked to a polynucleotide encoding BvLec1, AtLec1, BvLec2/Fusca3, AtLec2, BvWri1, AtWri1, and/or BvTag1 and transformed into cells from sugar beet, other root crop, *Nicotiana* spp or other plants. In another embodiment of this invention, an expression vector or cassette contains tissue specific promoter (e.g., a BvSTI promoter (of which SEQ ID NO: 10 is one example) and Bv major latex-like protein promoter) operably linked to a polynucleotide encoding BvLec1, AtLec1, BvLec2/Fusca3, AtLec2, BvWri1, AtWri1, and/or BvTag1, and the expression vector or cassette is transformed into cells from sugar beet, other root crop, *Nicotiana* spp., or other plants. In a third embodiment of this invention, an expression vector or cassette contains a constitutive promoter (e.g., CaMV 35S promoter) operably linked to a polynucleotide encoding BvLec1, AtLec1, BvLec2/Fusca3, AtLec2, BvWri1, AtWri1, and/or BvTag1, and the expression vector or cassette is transformed into cells from sugar beet, other root crop, *Nicotiana* spp., or other plants. In one embodiment, one selects genetically altered plant cells that express the indicated protein or transcribes the indicated gene, and then cultures the selected cells to form a genetically altered plant (regenerate the genetically altered plant) that produces the indicated protein or transcribes the indicated gene, and which also produces more fatty acids than a wild-type plant (not genetically altered) produces. In other embodiment, the indicated gene encodes BvLec1, AtLec1, BvLec2/Fusca3, AtLec2, BvWri1, AtWri1, and/or BvTag1. In other embodiment, the indicated gene encodes a selection marker, as described above, for which one can select. In yet another embodiment, one selects genetically modified plant cells and/or genetically modified plants (or part thereof) that produce higher amounts of at least one fatty acid than is produced by a wild-type plant (or part thereof). In another embodiment, one selects for genetically modified plants (or part thereof) that have higher resistance to an insect feeding on the genetically modified plant or part thereof, compared to a wild-type plant's resistance to the insect feeding on the wild-type plant.

As a class of agricultural products, root crops have nearly an order of magnitude higher yield of harvested weight per acre than any other crop—approximately 20-25 tons per acre (see earthtrends.wri.org/text/agriculture-food/country-profile-190). The cost of production is low, about $0.021 per pound for sugar beets, which includes the farmer's profit (The National Agricultural Statistics Service, nass.usda.gov/, statistics for "Sugarbeets" in 2006). They can be grown in any part of the US. The sucrose storage tissue in the tap root is anatomically distinct from the root vasculature and cambium layer (Artschwager E, "Anatomy of the Vegetative Organs of the Sugar Beet", *J. Ag. Res.* 33(2):143-176 (1926)). In principle, plants can be optimized for fuel production by genetically modifying them to produce oil directly in a form that can be delivered to a refinery. For example, *Arabidopsis thaliana* has been transformed to make omega-3 and omega-6 fatty acids (Qi B, et al. "Production of very long chain polyunsaturated omega-3 and omega-6 fatty acids in plants", *Nature Biotechnology* 22(6): 739-745 (2004)). Relatively simple chemical refinement (transesterification) can efficiently transform fatty acids into biodiesel.

The efficiencies of using sugar beets for oil production are very favorable compared to producing ethanol from corn. In 2007, corn yields averaged approximately 151 bushels per acre and the average yield of ethanol per bushel was 2.7 gallons, thus 408 gallons of ethanol/acre. In contrast, an acre of sugar beets can produce approximately 7000 pounds of sugar (sugarbeet.ucdavis.edu/sugar_industry). If this quantity of product is fat and converted to biodiesel (using a conversion factor of 7 pounds per gallon of diesel fuel (chevron.com/products/ourfuels/prodserv/fuels/documents/Diesel_Fuel_Tech_Review.pdf), it would yield approximately 1000 gallons of fuel, a 2.5 fold improvement over ethanol, and that factor ignores the higher energy density of diesel vs. ethanol. Economically, the comparison is also favorable. The cost per gallon for the agricultural product input for sugar beets is approximately $1.05/gallon. The cost of corn for one gallon of ethanol is approximately $1.48, and the cost of fermentation and distillation would be higher than the extraction from fat laden beets.

Most importantly, the present invention has some similarities to the overarching concept of self-replicating machines (see U.S. Pat. No. 6,510,359, "Method and system for self-replicating manufacturing stations"), in that genetically altered plants described herein are self-replicating chemical factories. The inputs to these factories are solar energy, carbon dioxide, water, and fertilizer, and the output is liquid fuel in the form of long chain fatty acids. The important contrast to all other biofuel inventions is that the present invention uses the plant for as much chemistry as possible, so no additional chemical process infrastructure is needed. Only new facilities needed to extract oils from the genetically altered sugar beet and/or *Nicotiana* spp. will be needed. Thus, the cost per gallon of fuel will be minimized relative to fermentation or algal biofuel methods.

Because the present invention uses carbon dioxide from the atmosphere as the carbon source for its oil, and because the amount of oil that can be produced from an acre of land has far more energy than the amount needed to make the fertilizer to grow an acre of sugar beets or *Nicotiana* spp., this invention has a negative carbon footprint. Thus, the exclusive use of this invention for all liquid fuel needs may reduce the growth in greenhouse gases from liquid fuels.

The present invention results in the modification of the biochemical pathways expressed in the genetically altered sugar beet and *Nicotiana* spp. plants to produce fats. Not wishing to be bound to any particular theory, it is currently hypothesized that these genetically altered plants are altered to up-regulate fatty acid biosynthesis pathways by transforming the plants with one or more expression vectors or cassettes containing one or more genes encoding transcription regulators that control the expression of genes involved in the fatty acid biosynthetic pathway. In the expression vector or cassette, the transcription regulator genes are operably linked to and controlled by one or more promoters. In addition, one can up-regulate fatty acid biosynthesis pathways in these plants by transforming the plants with expression vector(s) or cassette(s) containing a gene encoding an enzyme involved in fatty acid production (diacylglycerol-O-acyltransferase 1 (Tag1)) operably linked to the appropriate promoters. Because the root vasculature and the cambium layer are both distinct from the storage tissues, such modifications are not lethal.

FIG. 1 provides a generalized scheme for triacylglycerol (TAG) biosynthesis in developing seeds of oleaginous plants. Monounsaturated fatty acids (MUFAs) and saturated fatty acids (SFA) are synthesized in the plastid and, following export from this organelle, are converted to acyl-Coenzyme A (CoAs). Acyl-CoA can be further elongated through the catalytic action of fatty acid elongase (FAE) on the endoplasmic reticulum (ER). TAG can be synthesized via the acyl-CoA-dependent acylation of the glycerol backbone derived from sn-glycerol-3-phosphate (G3P). Phosphatidic acid phosphatase (PAP) catalyzes the dephosphorylation of phosphatidic acid (PA) to produce sn-1,2-diacylglycerol (DAG) prior to the final acylation catalyzed by acyl-CoA: diacylglycerol acyltransferase (DGAT or TAG1). DAG can also be converted to phosphatidylcholine (PtdC) via the action of sn-1,2-diacylglycerol:cholinephosphotransferase (CPT) and/or phosphatidylcholine:diacylglycerol cholinephosphotransferase (PDCT). MUFA at the sn-2 position of PtdC can undergo desaturation catalyzed by fatty acid desaturases 1 and 2 (FAD1 and FAD2), respectively. PtdC enriched in polyunsaturated fatty acid (PUFA) can be returned as DAG into the linear part of the G3P pathway leading to TAG via the action of PDCT. Phospholipase $A_2$ ($PLA_2$) may also catalyze the removal of PUFA from the sn-2 position PtdC which in turn is converted to acyl-CoA via the action acyl-CoA synthetase (ACS). In addition, acyl-CoA:lyso-phosphatidylcholine acyltransferase (LPCAT) may catalyze acyl-exchange between the sn-2 position of PUFA-enriched PtdC and the acyl-CoA pool. Low molecular mass soluble acyl-CoA-binding protein (ACBP) may interact with acyl-CoA and encourage the reverse reaction of LPCAT leading to acyl-CoA. Phospholipid: diacylglycerol acyltransferase (PDAT) catalyzes the transfer of fatty acid (FA) at the sn-2 position of PtdC to DAG to also generate TAG. PLA2 and PDAT have been implicated in catalyzing the removal of unusual FAs from the PtdC. LPCAT may catalyze the reacylation of lyso-phosphatidylcholine (LPC) produced through the action of PLA2 or PDAT. Other abbreviations contained in FIG. 1 are GPAT for acyl-CoA:sn-glycerol-3-phosphate acyltransferase; LPA for lyso-phosphatidic acid; LPAAT for acyl-CoA:lyso-phosphatidic acid acyltransferase; and PC for phosphocholine.

Figure 2:
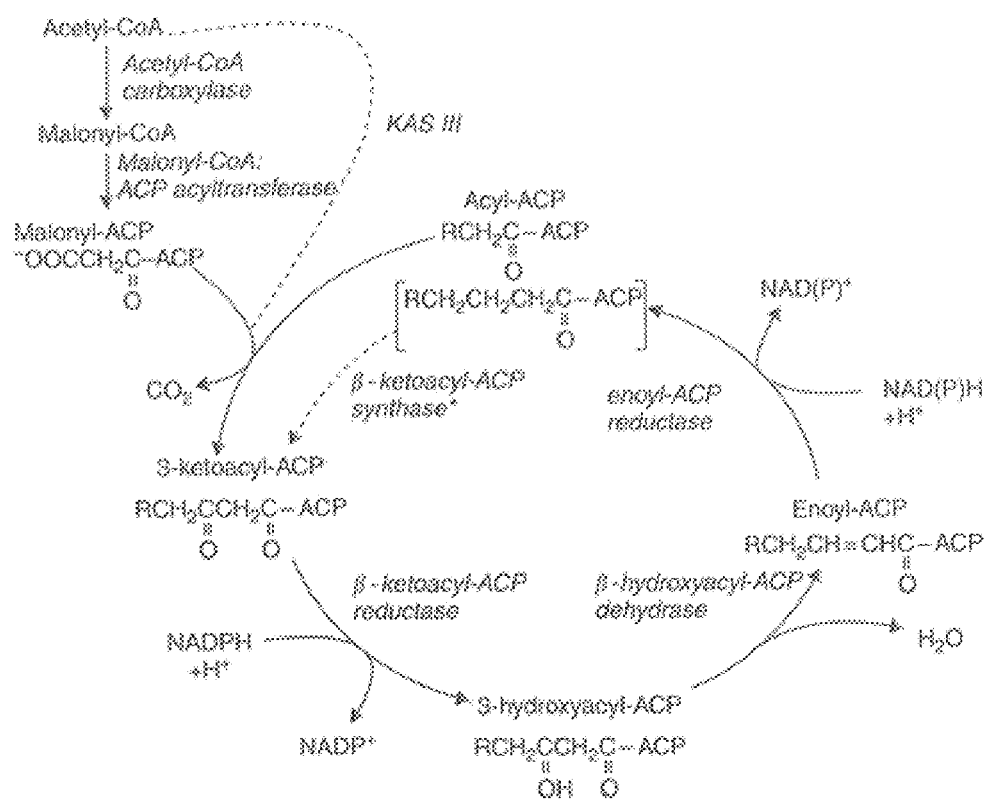
FIG. 2 illustrates the plant fatty acid biosynthetic pathway.

FIG. 2 is an overview of the fatty acid biosynthetic pathway in plants. In FIG. 2, ACP means acyl-carrier protein. CoA is Coenzyme A. KAS means β-ketoacyl-ACP synthase III. A fatty acid is a carboxylic acid with a long aliphatic tail (chain), which is either saturated or unsaturated. Non-limiting examples of unsaturated fatty acids include myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid. Non-limiting examples of saturated fatty acids include caprylic acid, capric acid, lauric acid, myristic acid, palmitic acid, stearic acid, arachidic acid, behenic acid, lignoceric acid, and cerotic acid.

The polynucleotides encoding the transcription regulators described in this invention appear to exert control on many aspects of fatty acid synthesis, sucrose production and metabolism, and reproduction. Two transcription regulators from sugar beets are leafy cotyledon 1 (Lec1) and wrinkled 1 (Wri1). The third transcription regulator from sugar beets, as explained below, has some homology to both leafy cotyledon 2 (Lec2) and Fusca3 present in *Arabidopsis* and is referred to here as Lec2/Fusca3. Not wishing to be bound to any particular theory, below is the current understanding of the activity of the transcription regulators disclosed herein. *Arabidopsis* Lec1, Lec2, and Fusca3 control the expression of genes encoding other transcription regulators that are involved in embryogenesis and seed maturation. *Arabidopsis* Lec1, Lec2, and Fusca3 directly and indirectly control the expression of genes involved in carbohydrate and lipid metabolism (catabolism and anabolism). Lec2 and possibly Fusca3 directly control expression of transcription of Wri1, while Lec1 indirectly controls expression of Wri1. Lec1 and Fusca3 appear to regulate greater than 50% of the genes in the plastidial fatty acid synthesis and modification pathways, including genes encoding several subunits of acetyl-CoA carboxylase; acyl carrier protein (ACP); stearoyl-acyl carrier protein desaturase; fatty acid desaturase 2; fatty acid desaturase 3; fatty acid elongases; diacylglycerol acyltransferase (Tag); and oleosin. Lec1 and Fusca3 also appear to positively control the expression of genes implicated in sucrose synthesis, sucrose transport, and glycolysis (including several sucrose synthases and multiple subunits of plastidial pyruvate kinase and plastidial pyruvate dehydrogenase). Pyruvate kinase and pyruvate dehydrogenase catalyze, respectively, the irreversible synthesis of pyruvate and its decarboxylation to acetyl-CoA for fatty acid synthesis. Lec2 indirectly controls the transcription of Fusca3 and several genes involved in fatty acid synthesis and, perhaps, directly controls expression of Lec1. Mutations within or over-expression of Lec2 and Fusca3 are often associated with pleiotropic effects. Seed-specific over-expression of maize Lec1 (ZmLec1) results in an average 35% increase in seed oil but reduced germination and vegetative growth in the field. Over-expression of Wri1 elevates relative oil levels in some plants' seeds by up to 20%, and constitutive Wri1 expression throughout the plant can induce ectopic seed oil synthesis in vegetative tissues when transformed seedlings are grown on sucrose-containing media. In one study, constitutive expression of Wri1 had no adverse effects on the plant; while in another study, constitutive expression led to numerous pleiotropic effects, ranging from stunted growth and reduced apical dominance, to poor seed set, reduced seed size and reduced seed oil content. Wri1's primary function in seed oil deposition appears to be a positive regulator of genes involved in late glycolysis and fatty acid biosynthesis. Some genes regulated by Wri1 include genes encoding several subunits of plastidial pyruvate kinase, several subunits of plastidial pyruvate dehydrogenase, ACP, ketoacyl-ACP synthase III, and acyl-ACP thio-esterase. Wri1 does not appear to control expression of Tag1.

The polynucleotide sequences encoding the transcription regulators (Lec1, Lec2/Fusca3, and Wri1) and encoding the enzyme Tag1 are obtained from *Beta vulgaris* (sugar beet). Also, *Arabidopsis* Lec1, Lec2, and Wri1 are used in this invention. Information about the DNA and amino acid sequences of these genes and the encoded proteins are in Table 1, supra. BvLec1, AtLec1, BvLec2/Fusca3, AtLec2, BvWri1, AtWri1, and BvTag1 each encode a "fatty acid biosynthesis protein", namely BvLec1, AtLec1, BvLec2/Fusca3, AtLec2, BvWri1, AtWri1, and BvTag1, respectively.

The present invention results in the modification of the biochemical pathways expressed in the genetically altered sugar beet, other genetically altered root crops, and genetically altered tobacco to produce and store fats in various plant tissue, includes the roots, leaves, stems, bark, etc. The genetically altered plants described herein are transformed with an expression vector or cassette containing a heterologous promoter operably linked to a polynucleotide encoding the desired protein and result in the up-regulation of the fatty acid biosynthesis pathways compared to wild-type (non-transformed) plants. It is also possible that such transformed plants will also up-regulate sucrose degradation enzymes compared to wild-type plants. Not wishing to be bound to any particular hypothesis, the genetically altered plant converts the sucrose produced by the leaves into fatty acids and/or triacylglycerol. Expression of the transcription regulator(s) and/or enzyme(s) of this invention within the genetically altered plant does not affect the growth of the genetically altered plant.

Furthermore, the genetically altered plants of this invention have an additional and surprising characteristic of having increased resistance to various insects. A combination of fatty acids with ivermectin or milbemycin appear to have enhanced insecticidal activity over the activity of ivermectin or milbemycin alone (see U.S. Pat. Nos. 5,192,546 and 5,346,698). Further, microemulsions of certain fatty acid esters also appear to have insecticidal activity (see, U.S. Pat. Nos. 5,674,897; 5,698,592; and 6,124,359). Various fatty acids are being commercialized for a variety of pesticidal applications, including but not limited to, herbicides (e.g., SCYTHE® by Dow Agrosciences contains perlargonic acid, a C9 saturated fatty acid); bactericides and fungicides (see U.S. Pat. Nos. 4,771,571 and 5,246,716); and insecticides (e.g., SAFER INSECTICIDAL SOAP® by Safer, Inc.). However, until now, it was unknown if enhanced levels of triacylglycerol and/or fatty acids in a genetically altered plant would impart enhanced resistance to insects that feed on the tissue of the genetically altered plant compared to the wild-type plant's resistance to insects that feed on it. Not wishing to be bound to any particular hypothesis, fatty acids and/or triacylglycerol may derive their pesticidal effects by adversely interfering with a pest's cuticle or hypodermis via a detergent effect or through direct interaction between the fatty acid/triacylglycerol and lipophilic regions of the pest's plasma membranes (Davis, et al., *Journal of Nematology* 29:4S, 677-684 (1997)). In addition, numerous reports of fatty acids having a role as antimicrobial agents have been published. See Carballeira, *Progress in Lipid Research* 47:50-61 (2008).

In wild-type sugar beet plant (prior to any selective breeding to increase sucrose yield), the taproot is used as a food source for the second year growth which produces flowers. It is possible that sugar beets transformed with the expression vectors (or cassettes) and polynucleotides described herein may prevent flowering. However, some sugar beet mutants do not require large taproot formation for flowering (see, Panella and Hecker, *Crop Science* 35:6, 1721 (1995)). Thus, the recombinant sugar beets and other root crop plants described herein may flower normally. Should the plants not reproduce normally, it is possible for one to use inducible promoters so that one can induce expression of the polynucleotides described herein in a limited number of transformed plants, thereby allowing a portion of the transformed plants to reproduce by not inducing expression of the promoters.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference. No language in the specification should be construed as indicating any non-claimed element as essential to the practice of the invention.

Example 1. Promoters for Expression Vectors/Cassettes

In one embodiment of this invention, a known *Beta vulgaris* storage tissue specific promoter, the major latex-like protein promoter, Genbank accession AX449164, SEQ ID NO: 1 (Oltmanns, et al., *Planta* 224:3, 485-495 (2006)) is used in the expression vectors or cassettes of this invention. The *B. vulgaris* major latex-like protein has sequence similarity to the major latex proteins from the opium poppy, but has unknown function. This *B. vulgaris* promoter drives expression of genes encoding proteins within the storage tissue, albeit weakly. The sugar beet major latex-like protein promoter is active in storage tissue of at least one root crop.

In another embodiment of this invention, the expression vectors or cassettes of this invention can use one of the *Beta vulgaris* promoters discovered by the U.S.D.A. and which are described in U.S. Patent Application Publication 2014/0150138. The promoters were obtained from different strains of *B. vulgaris* and possess high percentage identity to each other. The promoters are referred to as "BvSTI promoters" because they control the expression of BvSTI in each of the strains from which they were obtained. The DNA sequence of one of these highly conserved BvSTI promoter sequences is in SEQ ID NO: 10. The BvSTI promoters are active in the storage tissue of at least one root crop, sugar beets. The DNA sequences of the BvSTI promoters described in U.S. Patent Application Publication 2014/0150138 are expressly incorporated herein (see SEQ ID NOs: 36-42 of the sequence listing for this patent application).

In another embodiment of this invention, CaMV 35S promoter, a constitutive promoter, is used to drive the transcription of the polynucleotides described herein. Other constitutive promoters, examples of which are discussed supra, can be used. However, in one embodiment, ssRBCS, a tissue-specific promoter, and the *Aspergillus nidulans* inducible promoter AlcA are expressly not used in the expression vectors or cassettes of this invention.

Example 2. Sugar Beet Specific Polynucleotides and Expression Vectors/Cassettes

The present invention also involves polynucleotides, obtained from sugar beets, encoding transcription regulators (Lec1, Lec2/Fusca3, and Wri1) and one enzyme (Tag1) involved in triacylglycerol synthesis, the proteins encoded by these polynucleotides, and expression vectors or cassettes containing one or more of the polynucleotides linked to one or more of the heterologous promoters discussed supra. The polynucleotides encoding the enzyme and transcription regulators are the sugar beet derived sequence for (1) Lec1 (Leafy Cotyledon1, SEQ ID NO: 2; amino acid sequence in SEQ ID NO: 6); (2) Lec2/Fusca3 (Leafy Cotyledon2/Fusca3, SEQ ID NO: 3; amino acid sequence in SEQ ID NO: 7); (3) Wri1 (Wrinkled1; SEQ ID NO: 4; amino acid sequence in SEQ ID NO: 8); and (4) Tag1 (diacylglycerol O-acyltransferase 1 (also referred to as "Dgat"), SEQ ID NO: 5; amino acid sequence in SEQ ID NO: 9).

In addition, the present invention also involves polynucleotides encoding *Arabidopsis thaliana* (At) transcription regulators Lec1 (see Mu, et al., *Plant Physiology* 148:2 1042-1054 (2008)), Lec2 (Mendoza, et al., *FEBS Letters* 579:21 4666-4670 (2005)), and Wri1 (Cernac and Benning, *The Plant Journal* 40:4 575-585 (2004)), and expression vectors or cassettes containing a heterologous promoter operably linked to one or more of these polynucleotides. AtLec1, AtLec2, and AtWri1 have been shown to induce fatty acid synthesis throughout *Arabidopsis* when these genes were over-expressed in all tissues of the plant. AtTag1 increases the production of oleic acid when over-expressed in *Nicotiana tabacum*. See, Andrianov, et al. (2010).

The cDNA sequences for the BvLec1, BvLec2/Fusca3, BvWri1, and BvTag1 (SEQ ID NO: 2-5, respectively) are identified by isolating RNA from approximately 100 mg of fresh immature sugar beet seeds taken from sugar beet flowering stalks using RNeasy Plant Mini Kit (Qiagen, Germantown, Md.) per manufacturer's instructions and treating it with RNase-free DNase (Qiagen, Germantown, Md.). The isolated RNA is sent to Tufts Genome Center (Boston, Mass.) for the generation of cDNA libraries which are sequenced on an Illumina Hiseq 2000 system (San Diego, Calif.). The sequencing reads (cDNA) are mapped and assembled onto a draft sugar beet genome published by the BeetSeq consortium using the Tophat and Cufflinks programs (Trapnell, et al., *Nat. Protocols* 7:562-578 (2012)). Sugar beet cDNA sequences having some homology to the AtLec1, AtLec2, AtWri1, and AtTag are selected. The sugar beet cDNA sequences obtained are also compared to *Arabidopsis thaliana* sequences using BLAST®.

Using a BLASTN® analysis, the cDNA sequence for BvWri1 between nt 247 and nt 764 is approximately 81% identical to *Jatropha curcas* Wri1. The cDNA sequence for BvWri1 between nt 233 to nt 764 is approximately 77% identical to AtWri1. Using a BLASTP® analysis, the amino acid sequence for BvWri1 from aa 54 to aa 410 is approximately 58% identical to hypothetical protein CARUB from *Capsella rubella*. The amino acid sequence from aa 54 to aa 410 of BvWri1 is approximately 58% identical to AtWri1.

Using a BLASTN® analysis, the cDNA sequence for BvLec1 from nt 103 to nt 404 is approximately 82% identical to soybean Lec1. The cDNA sequence for BvLec1 from nt 106 to nt 402 is approximately 77% identical to an AtLec1 like transcript. Using a BLASTP® analysis, the amino acid sequence of BvLec1 from aa 24 to aa 198 is approximately 72% identical to a putative transcription factor in *Vitis vinifera*. The amino acid sequence for BvLec1 from aa 24 to aa 161 is approximately 75% identical to AtLec1.

Using a BLASTN® analysis, the cDNA sequence for BvTag1 from nt 299 to nt 1543 is approximately 79% identical to *V. vinifera* diacylglycerol O-acyltransferase 1-like mRNA. The cDNA sequence for BvTag1 from nt 299 to nt 1544 is approximately 75% identical to AtTAG1. Using a BLASTP® analysis, the amino acid sequence of BvTag1 from aa 1 to aa 516 is approximately 69% identical to a hypothetical protein PRUPE in *Prunus persica*. The amino acid sequence of BvTag1 from aa 99 to aa 518 is approximately 77% identical to AtTag1.

Using a BLASTN® analysis, the cDNA sequence for BvLec2/Fusca3 from nt 281 to nt 518 is approximately 68% identical to AtLec2. The cDNA sequence for BvLec2/Fusca3 from nt 233 to nt 619 is approximately 74% identical to *Brassica napus* Fusca3. Using a BLASTP® analysis, the complete amino acid sequence of BvLec2/Fusca3 is approximately 50% identical to an uncharacterized transcription factor in *A. thaliana*, and only 50% identical to AtFusca3. The amino acid sequence of BvLec2/Fusca3 from aa 75 to aa 298 is 59% identical to *B. napus Fusca*3. Because of the poor matches for this last gene/protein, this last transcription regulator is referred to herein as BvLec2/Fusca3. It is hypothesized that BvLec2/Fsuca3 is a transcription regulator for lipid synthesis, similar to AtLec2 and AtFusca3.

Example 3. Expression Vectors Generation

The nucleotide sequences for BvLec1, BvLec2/Fusca3, BvWri1, BvTag1, AtLec1, AtLec2, and AtWri1 are synthesized using DNA synthesis at Geneviz, Inc. (South Plainfield, N.J.), incorporating a BglII restriction enzyme sequence 5' of the ATG start codon and a 3' BstEII sequence after the stop codon sequence in each gene, except with BvLEC1, where a 3' AflII restriction enzyme site was synthesized after the stop codon. Each newly synthesized gene is individually incorporated into the pCambia 1301 plant expression vector under control of CaMV 35S (35S) promoter, a constitutive promoter, to generate pCAMBIABvLec1, pCAMBIABvLec2/Fusca3, pCAMBIABvWri1, pCAMBIABvTag1, pCAMBIAAtLec1, pCAMBIAAtLec2, and pCAMBIAAtWri1, respectively (Genewiz, Inc., South Plainfield, N.J.). pCAMBIA1301 carries the hpt marker gene for selection of hygromycin resistant transformed plant cells.

Example 4. Generation of Genetically Altered *Nicotiana benthamiana*

*A. tumefaciens* EHA 105 strain harboring either pCAMBIABvLec1, pCAMBIABvLec2/Fusca3, pCAMBIABvWri1, pCAMBIABvTag1, pCAMBIAAtLec1, pCAMBIAAtLec2, pCAMBIAAtWri1, or pCAMBIA35S-Gus (pCAMBIA 1301 empty vector control) are used as inocula for *N. benthamiana* Domin plants transformation. Prior to co-cultivation, bacteria are grown for two days at 28° C. in YEB liquid medium (Van Larebeke et al. 1977) supplemented with kanamycin and ampicillin in concentrations of 50 mg/l and 100 mg/l, respectively. Bacteria are harvested by centrifugation at 4000×g for ten minutes and re-suspended in 30 ml liquid MS (Murashige and Skoog 1962).

*N. benthamiana* leaf explants (1 cm$^2$) are cut from fully expanded leaves of greenhouse-grown plants and are surface-sterilized in 70% ethanol and 10% commercial bleach solution, then are washed five times with sterile water. Explants are then placed in the *A. tumefaciens* bacterial suspension for ten minutes, gently blotted on sterile filter paper and are placed on nutrition medium containing MS salts, B5 vitamins (Murashige and Skoog, 1962. *Physiologia Plantarum* 15:473-479; Gamborg et al. 1965. In vitro 12(7), 473-478), 3% sucrose and 0.7% agar. After two days of co-cultivation in the dark at 25° C., explants are washed with sterile solutions of cefotaxime and carbenicillin (500 mg/leach) and are placed on MS plus B5 vitamins agar solidified media, 20 mg/l hygromycin sulfate, 200 mg/l cefotaxime and 500 mg/l carbenicilline (Smigocki et al., 2008. *SugarTech* 10(1):91-98; Smigocki, et al., 2009. *Plant Cell Tissue and Orgran Culture* 97:167-174, 2009). Regenerated shoots are excised and placed on the same media. Nicely developed 1-2 cm tall shoots are transferred to the same media supplemented with 5 mg hygromycin sulfate/l for rooting. After few weeks growing in vitro, putatively transformed *N. benthamiana* plants (T0) are acclimated and transferred to greenhouse where they are maintained under controlled environmental conditions (25±5° C. during the day and 22±3° C. overnight, with day length of 12-14±1 h). All plants are fertilized monthly with Osmocote (Scott's Miracle-Gro, Marysville, Ohio). T1 and T2 progeny derived T0 transgenic plants are germinated on hygromycin containing media for further studies. Untransformed *N. benthamiana* plants are included in all experiments as negative controls.

The seeds harvested from self-fertilized T0 plants are imbibed overnight in water. Seeds are surface sterilized in 70% ethanol and 10% commercial bleach solution containing 4% sodium hypochlorite for eight minutes. Seeds are then rinsed with sterile water and are germinated on hormone-free ½ strength MS salts, B5 vitamins, 0.6% agar medium supplemented with hygromycin in concentration 40 mg/l in dark. After five days, the plates with germinated seeds are moved to sixteen hours light/eight hours dark conditions. *N. benthamiana* seedlings with normal growth are counted as hygromycin resistant and, based on the number of resistant and susceptible plants, the expected segregation ratio for each T1 line is tested using the chi-square ($\chi^2$) test (Greenwood and Nikulin 1996. A Guide to Chi-squared Testing, Wiley, N.Y.). All seeds from the greenhouse-grown transformed T1 plants which are tested for hygromycin resistance are resistant to hygromycin. Using the chi-square test, it is believed that a single locus insertion of the hptII gene occurred for tested T1 plants.

Example 5. Generation of Genetically Altered *Beta vulgaris* Hairy Roots

A single colony of *Agrobacterium rhizogenes* strain 15834 harboring either pCAMBIABvLec1, pCAMBIABvLec2/Fusca3, pCAMBIABvWri1, pCAMBIABvTag1, pCAMBIAAtLec1, pCAMBIAAtLec2, pCAMBIAAtWri1, or pCAMBIA35S-Gus (pCAMBIA 1301 empty vector control) is used as inocula for grown overnight in YEB medium with kanamycin sulfate (50 mg l$^{-1}$) at 190 rpm. At 1.0 OD$_{600}$, bacterial cells are pelleted by centrifugation at 4000×g for 10 minutes and re-suspended in antibiotic-free liquid ½ B5 (½×Gamborg salts, 1×B5 vitamins, 3% sucrose, pH 5.8; Gamborg et al., *Exp. Cell Res.* 50: 48-51, 1968) medium for inoculation of plant tissues.

Sugar beet petiole transformation is essentially done as described by Smigocki, et al. (*Plant Cell Tiss. Org. Cult.* 97:167-174, 2009). Petioles are excised from fully expanded leaves of greenhouse-grown plants of sugar beet germplasm F1010 and surface-sterilized in 1% sodium hypochlorite with 0.01% SDS. Petioles are cut into 1 cm long pieces and infected with *A. rhizogenes* strain for 10 minutes, blotted dry and plated on ½ B5 medium. After 2 days of co-cultivation in the dark at 25° C., explants are washed with cefotaxime and carbenicillin (500 mg $l^{-1}$ each) and plated on ½ B5 medium containing 250 mg 0 of the above antibiotics to eliminate *Agrobacterium*. Regenerated hairy roots are excised and cultured at 20° C. in the dark on ½ B5 agar medium containing hygromycin sulfate at 5 mg $l^{-1}$. These hairy roots are micro-propagated in-vitro multiple times until large quantities of plant material are produced using the protocol described in Smigocki, et al., *Plant Cell Tiss. Org. Cult.* 97:167-174, 2009.

Example 6. Confirmation of BvLec1, BvLec2/Fusca3, BvWri1, BvTag1, AtLec1, AtLec2, and AtWri1 in Genetically Altered *N. benthamiana* Plants and *B. vulgaris* Hairy Root Cell Cultures To confirm the presence of each transgene in the T1 *N. benthamiana* genome, PCR analysis of the genetically altered plants is performed using universal primers for the transformation vector pCAMBIA 1301 (F: TCATTTGGA-GAGAACACGGG (SEQ ID NO: 34) and R: AAGACCG-GCAACAGGATTC (SEQ ID NO: 35)). Genomic DNA is purified using DNeasy Plant Mini Kit (Qiagen, Germantown, Md.) per manufacturer's instructions from approximately 100 mg of fresh leaf tissue. DNA concentration and purity are determined using an ND-8000 Spectrophotometer (NanoDrop Technologies Inc., Wilmington, Del.). PCR is used to amplify each transgene DNA from about 100 ng of total DNA under the following conditions: 94° C. for 2 minute, followed by 30 cycles of 94° C. for 30 seconds, 55° C. for 45 seconds, 72° C. for 1 minute 30 seconds, ending with the final extension at 72° C. for 5 minutes. Histochemical β-glucuronidase (Gus) assays are used to determine Gus expression in negative control plants transformed with the vector control plasmid (Jefferson, *Plant Mol. Biol. Rep.* 5:387-405 1987).

TABLE 4

| Gene | Primers (5'-3') (forward (F) and reverse (R)) | Amplicon size (bp) |
| --- | --- | --- |
| AtLec1 | F: ATGGAACGTGGAGCTCCCTT CT (SEQ ID NO: 17) R: TTCACTTATACTGACCATAA TGG (SEQ ID NO: 18) | 718 |
| AtLec2 | F: ATGGATAACTTCTTACCCTT TC (SEQ ID NO: 19) R: TCACCACCACTCAAAGTCGT TA (SEQ ID NO: 20) | 1,092 |
| AtWri1 | F: ATGAAGAAGCGCTTAACCAC (SEQ ID NO: 21) R: CTCAGACCAAATAGTTACAA (SEQ ID NO: 22) | 1,294 |
| BvLec1 | F: ATGACCAATCACAGCAGCAA CAAC (SEQ ID NO: 23) R: TTAGTTGTGGTGACCATATG GCTC (SEQ ID NO: 24) | 708 |

TABLE 4-continued

| Gene | Primers (5'-3') (forward (F) and reverse (R)) | Amplicon size (bp) |
| --- | --- | --- |
| BvLec2/ Fusca3 | F: ATGATGATGATGGTGGAGGA GAGAG (SEQ ID NO: 25) R: TCAATAGAAGTCGTCAAGGG ACAAAT (SEQ ID NO: 26) | 900 |
| BvWri1 | F: ATGAAGAAGAGGTCAATTAC TAA (SEQ ID NO: 27) R: TTACAATTGACATGAGACTA AGC (SEQ ID NO: 28) | 1,374 |
| BvTag1 | F: ATGGCGATTTCGGATTCGCC TGAG (SEQ ID NO: 29) R: TCATGCTAAATTGCCTTTGC GATTC (SEQ ID NO: 30) | 1,557 |
| Bv actin | F: GTATTGTKAGCAACTGGGAT GA (SEQ ID NO: 31) R: AACKYTCAGCCCRATGGTAA T (SEQ ID NO: 32) | 540 |

For sugar beet hairy root cultures, RT-PCR analysis is used to examine the relative amount of mRNA for each of the transgenes, BvLec1, BvLec2/Fusca3, BvWri1, BvTag1, AtLec1, AtLec2, and AtWri1, using the gene specific primers listed in Table 4, supra. To assist with determining the relative amounts of mRNA present, the amount of mRNA of each of the transgenes, BvLec1, BvLec2/Fusca3, BvWri1, BvTag1, AtLec1, AtLec2, and AtWri1, is normalized to the constitutively expressed *B. vulgaris* actin gene. Total RNA is isolated using RNeasy Plant Mini Kit (Qiagen, Germantown, Md.) per manufacturer's instructions from approximately 100 mg of leaf tissue (either fresh leaf tissue or leaf tissue that was frozen at −80° C.) and treated with RNase-free DNase (Qiagen, Germantown, Md.). Titanium One-Step RT-PCR Kit (Clontech Laboratories Inc., Mountain View, Calif.) is used per manufacturer's instructions to amplify each transgene's transcripts from about 100 ng of total RNA under the following conditions: 50° C. for 1 hour, 94° C. for 2 minute 40 seconds, followed by 30 cycles of 94° C. for 30 seconds, 60° C. for 40 seconds, 72° C. for 1 minute 30 seconds, ending with the final extension at 72° C. for 5 minutes. The indicated forward and reverse primers in Table 4 for BvLec1, BvLec2/Fusca3, BvWri1, BvTag1, AtLec1, AtLec2, and AtWri1 are used to amplify amplicons of the indicated size. To normalize the RT-PCR results, transcripts of the constitutively expressed *B. vulgaris* actin gene are used as loading controls using the forward and reverse primers indicated in Table 4, supra, to generate an amplicon of 0.54 Kb using the same reaction conditions as described above.

PCR assays reveal the presence of BvLec1, BvLec2/Fusca3, BvWri1, BvTag1, AtLec1, AtLec2, and AtWri1 DNA in transgenic *N. benthamiana* plants. No signals are detected in the vector control (empty vector) transgenic plants (pCAMBIA 1301) and normal untransformed plants used as negative controls.

RT-PCR assays reveal moderate levels of BvLec1, BvLec2/Fusca3, BvWri1, BvTag1, AtLec1, AtLec2, and AtWri1 mRNA in each of the transformants. No detectable background mRNA is observed in any of the transformed hairy root lines except for low levels of BvLec2/Fusca3 and BvTag1 mRNA that are detected in the *B. vulgaris* negative control transformed with the empty vector plasmid (pCAMBIA 1301).

Example 7. Fatty Acid Profiling

Samples of each genetically altered hairy root cultures and genetically altered *N. benthamiana* plants made supra, as well as negative controls and baseline standard controls, are sent to New Jersey Feed Laboratory, Inc., (Trenton, N.J.) and Cumberland Valley Analytical Services (Hagerstown, Md.) for fatty acid profiling to determine the amount of fatty acids produced when BvLec1, BvLec2/Fusca3, BvWri1, BvTag1, AtLec1, AtLec2, and AtWri1 are constitutively expressed in the indicated genetically altered plants. The negative controls are genetically altered sugar beet hairy root cells and genetically altered *N. benthamiana* plants transformed with a "blank" expression vector (lacking one of the fatty acid biosynthesis transgenes). *N. benthamiana* leaves or sugarbeet taproot spiked with 1% olive oil, red beet taproot spiked with 1% olive oil, and red beet taproot spiked with 2% olive oil, are positive controls to confirm detection of fatty acids by the instrument used in the assay. Samples of wild-type sugar beet and wild-type red beet taproots and wild-type *N. benthamiana* leaves are used to determine a baseline standard for amount of fatty acids present in untransformed samples. All samples are freeze dried and stored at −80° C. temperature until the fatty acid levels are determined in order to prevent degradation of the fatty acids. Table 5, infra, shows the percentage of total fatty acid (FA) content, as well as the percentage of linolenic acid (contained in parentheses) in particular identified isolates of genetically altered *N. benthamiana* plants containing and expressing BvLec1, BvLec2/Fusca3, BvWri1, BvTag1, AtLec1, AtLec2, and AtWri1 or the empty vector control. Total fatty acid (and linolenic acid) is expressed as percentage (%) of sample basis. An empty vector is a transgenic plant that contains the vector only; none of the gene sequences described herein (negative control). "No vector" is untransformed *N. benthamiana*. Table 6, infra, shows the total fatty acid (FA) content in the identified isolates of genetically altered *B. vulgaris* F1010 roots containing and expressing BvLec1, BvLec2/Fusca3, BvWri1, BvTag1, AtLec1, AtLec2, and AtWri1. Total fatty acid is expressed as percent (%) of sample basis. An "empty vector" is a transgenic plant that contains the vector only; none of the gene sequences described herein (negative control). "No vector" are untransformed F1010 *B. vulgaris* roots (roots) and red beet roots.

TABLE 5

Fatty acid (FA) content as indicated by a percentage (and the percentage of linolenic acid - inside the parentheses) in the leaves of the identified genetically altered isolates of *N. benthamiana* transformed with BvLec1, BvLec2/Fusca3, BvWri1, BvTag1, AtLec1, AtLec2, and AtWri1.
Transformed *N. benthamiana* plants

| Sugar beet genes | % FA (Linolenic acid %) | Arabidopsis genes | % FA (Linolenic acid %) |
|---|---|---|---|
| BvLec1 | | AtLec1 | |
| 29-3 | 4.9 (2.4) | 2-4 | 4.7 (2.4) |
| 29-7 | 5.0 (2.5) | 3-1 | 3.6 (1.5) |
| 30-1 | 3.5 (1.8) | 3-2 | 2.9 (1.3) |
| 30-2 | 3.2 (1.6) | 3-5 | 5-0 (2.6) |
| 78-3 | 5.0 (2.5) | | |
| 134-9 | 4.9 (2.5) | | |
| 136-2 | 5.5 (2.7) | | |
| 136-8 | 4.9 (2.5) | | |
| BvLec2/Fusca3 | | AtLec2 | |
| 36-1 | 3.4 (1.9) | 74-3 | 3.4 (1.7) |
| 38-1 | 4.6 (2.4) | 74-4 | 3.5 (1.8) |
| 42-1 | 2.9 (1.5) | | |
| 42-2 | 3.1 (1.6) | | |
| 43-1 | 4.5 (2.5) | | |
| 43-4 | 4.6 (2.5) | | |
| 45-2 | 5.4 (2.9) | | |
| 45-3 | 4.2 (2.3) | | |
| 56-1 | 3.3 (1.7) | | |
| 56-2 | 4.9 (2.5) | | |
| 62-2 | 3.4 (1.6) | | |
| 62-7 | 2.8 (1.4) | | |
| 65-1 | 5.1 (2.8) | | |
| 65-9 | 3.7 (2.0) | | |
| 66-2 | 4.6 (2.3) | | |
| 66-4 | 4.9 (2.4) | | |
| 89-3 | 3.0 (1.6) | | |
| 89-5 | 5.2 (2.6) | | |
| BvWri1 | | AtWri1 | |
| 24-2 | 4.7 (2.5) | 16-1 | 4.6 (2.4) |
| 24-4 | 5.4 (2.8) | 16-9 | 4.9 (2.2) |
| 25-1 | 3.6 (1.8) | 17-4 | 2.8 (1.4) |
| 27-1 | 4.3 (2.2) | 22-5 | 4.6 (2.3) |
| 27-4 | 4.8 (2.4) | 23-3 | 3.6 (1.8) |
| 75-1 | 5.4 (2.8) | 23-5 | 5.4 (2.7) |
| 77-3 | 4.6 (2.4) | | |
| 125-2 | 5.2 (2.5) | | |
| 128-1 | 3.5 (1.7) | | |
| BvTag1 | | | |
| 53-5 | 4.9 (2.4) | | |
| 54-1 | 3.7 (1.8) | | |
| 54-3 | 3.2 (1.6) | | |
| 82-3 | 4.8 (2.4) | | |
| 82-4 | 5.6 (2.9) | | |
| 84-1 | 3.9 (1.9) | | |
| 84-3 | 2.8 (1.3) | | |
| 84-4 | 4.3 (2.2) | | |
| Empty Vector | | | |
| 68-1 | 2.6, 2.7, 2.9 (1.3) | | |
| 69-5 | 4.0 (2.0) | | |
| 133-1 | 3.2 (1.7) | | |
| 133-3 | 3.9 (1.9) | | |
| No Vector | | | |
| 72-1 | 2.5, 2.7, 2.4, 2.5 (1.3) | | |

TABLE 6

Fatty acid (FA) content (%) in identified isolates of sugar beet (*B. vulgaris*) hairy roots transformed with BvLec1, BvLec2/Fusca3, BvWri1, BvTag1, AtLec1, AtLec2, and AtWri1.
Transformed *B. vulgaris* roots

| Sugar beet genes | % FA | Arabidopsis genes | % FA |
|---|---|---|---|
| BvLec1 | | AtLec1 | |
| 6-2 | 1.8 | 1-4 | 2.3 |
| 6-7 | 1.6 | 1-7 | 1.7 |
| 6-9 | 1.6 | 1-10 | 1.8 |
| 6-10 | 1.6 | | |
| BvLec2/Fusca3 | | AtLec2 | |
| 8-3 | 1.6 | 2-2 | 1.1 |
| 8-4 | 1.6 | 2-4 | 1.8 |

TABLE 6-continued

Fatty acid (FA) content (%) in identified isolates of sugar beet
(*B. vulgaris*) hairy roots transformed with BvLec1, BvLec2/Fusca3,
BvWri1, BvTag1, AtLec1, AtLec2, and AtWri1.
Transformed *B. vulgaris* roots

| Sugar beet genes | % FA | Arabidopsis genes | % FA |
|---|---|---|---|
| 8-9 | 1.6 | 2-9 | 1.8 |
| 8-10 | 1.7 | | |
| BvWri1 | | AtWri1 | |
| 5-4 | 1.7 | 3-3 | 2.2 |
| 5-5 | 1.7 | 3-4 | 2.1 |
| 5-8 | 1.6 | 3-5 | 2.0 |
| 5-9 | 1.8 | | |
| BvTag1 | | | |
| 7-1 | 1.7 | | |
| 7-4 | 1.5 | | |
| 7-9 | 1.5 | | |
| Empty Vector | | | |
| 31-11 | 0.9, 0.9 | | |
| 31-18 | 0.6, 0.9 | | |
| 31-9 | 0.9, 1.1, 1.1 | | |
| No Vector | | | |
| Roots | 0.4, 0.5, 0.4, 0.4, 0.6, | | |
| Red beet roots | 0.4, 0.6, 0.4 | | |

Figure 4:
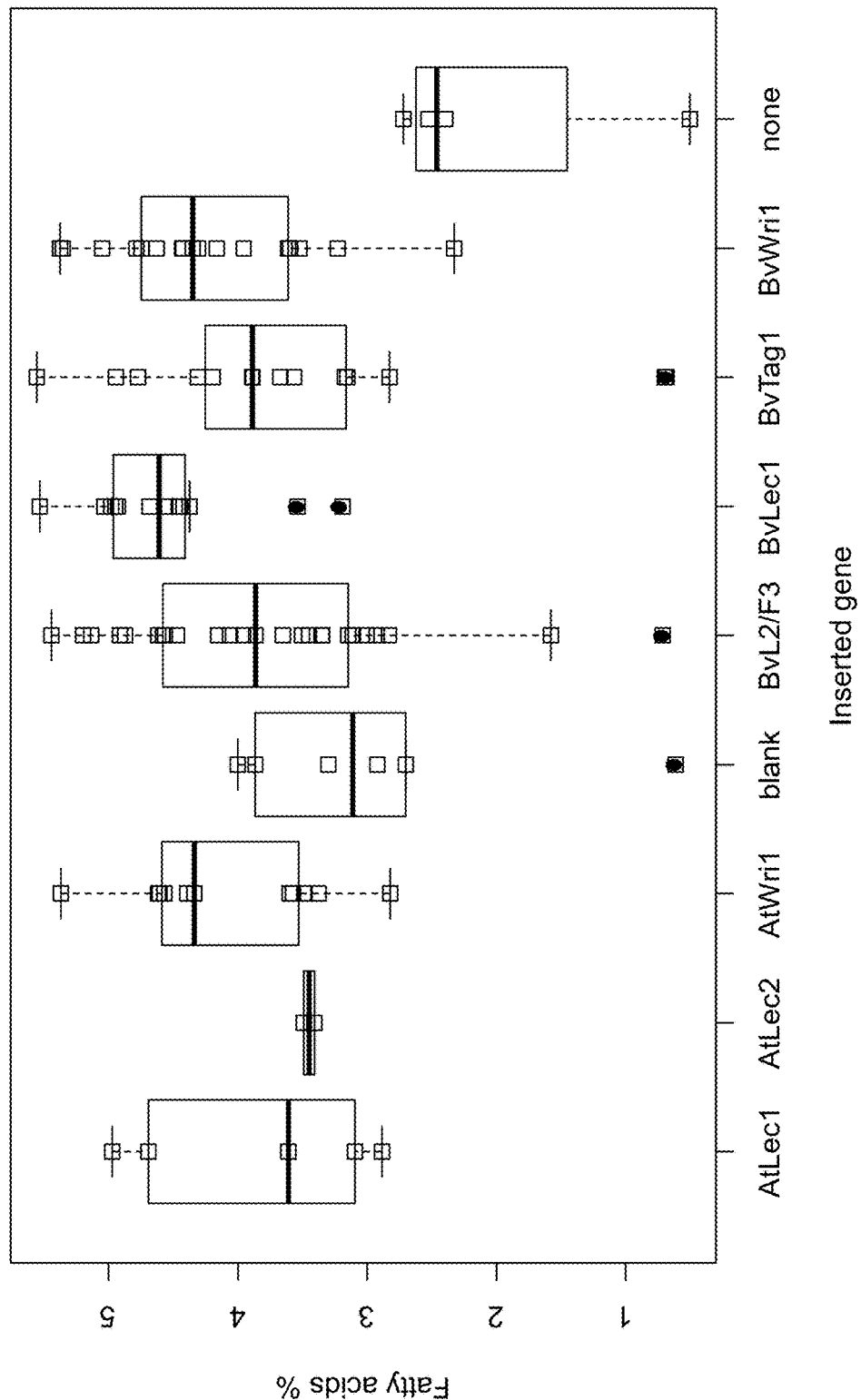
FIG. 4 shows the total fatty acid content in N. benthamiana samples transformed with either BvLec1, BvLec2/Fusca3, BvWri1, BvTag1, AtLec1, AtLec2, or AtWri1.
Figure 5:
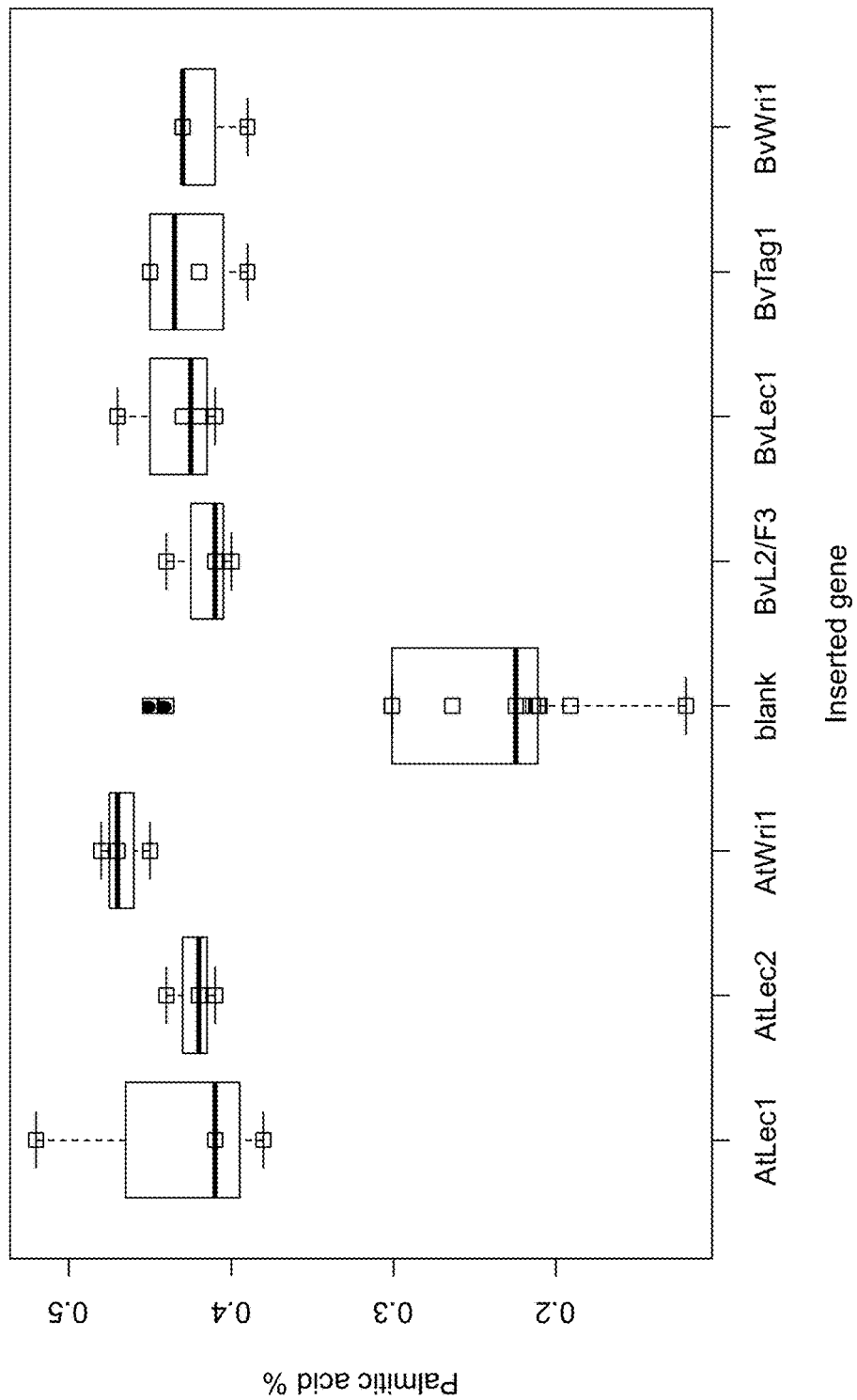
FIG. 5 shows the palmitic acid content in sugar beet roots transformed with either BvLec1, BvLec2/Fusca3, BvWri1, BvTag1, AtLec1, AtLec2, or AtWri1.
Figure 6:
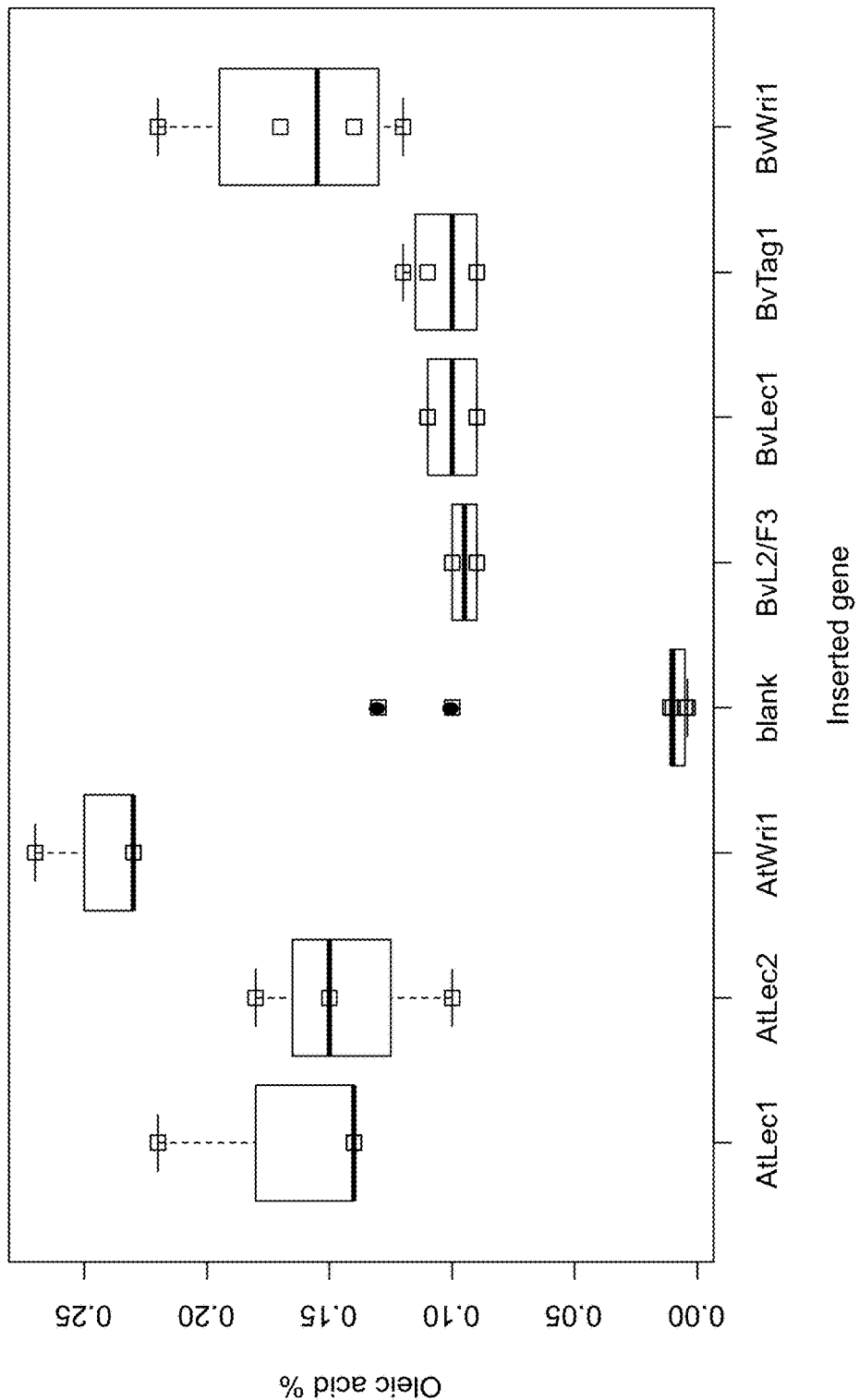
FIG. 6 shows the oleic acid content in sugar beet roots transformed with either BvLec1, BvLec2/Fusca3, BvWri1, BvTag1, AtLec1, AtLec2, or AtWri1.
Figure 7:
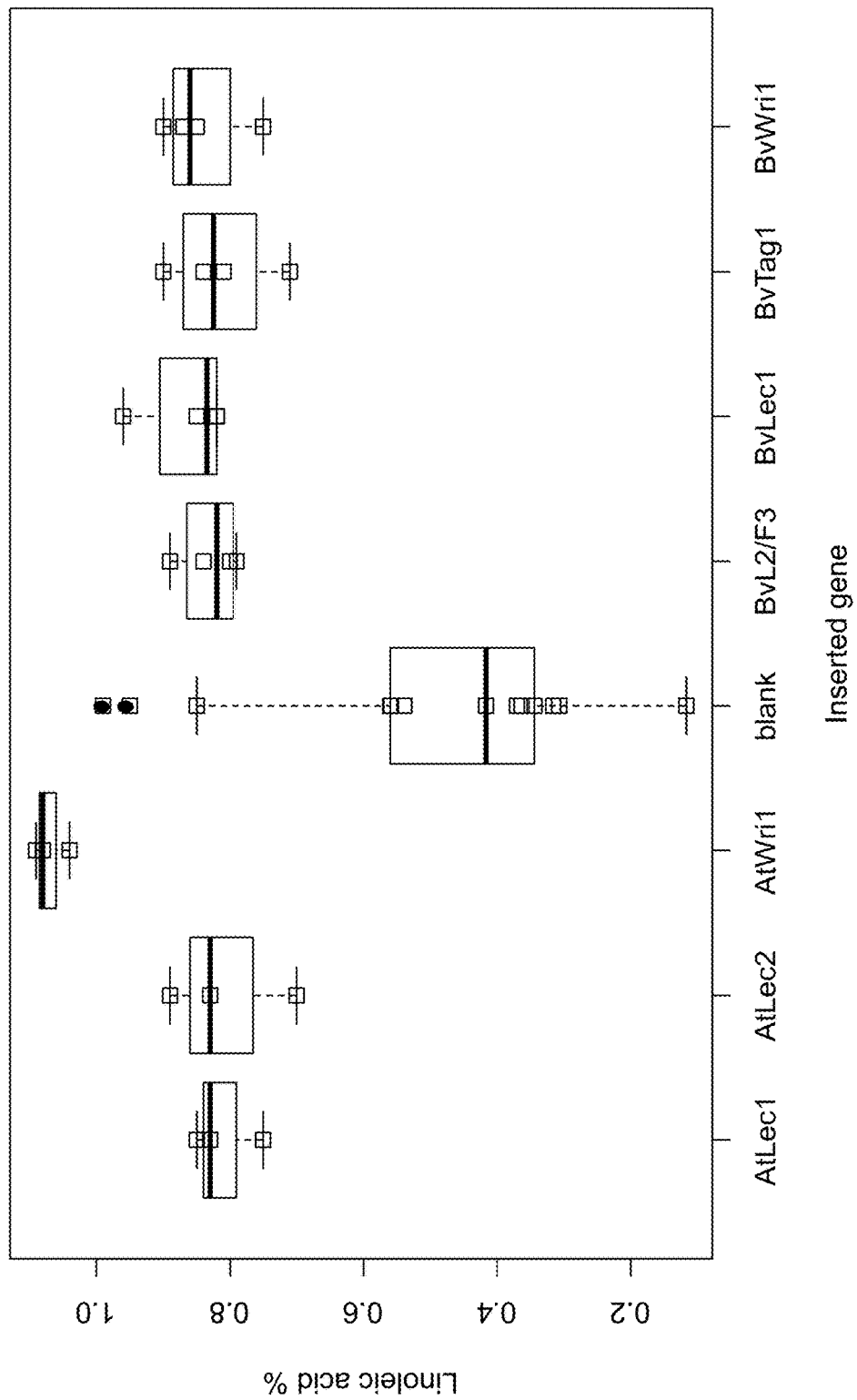
FIG. 7 shows the linoleic acid content in sugar beet roots transformed with either BvLec1, BvLec2/Fusca3, BvWri1, BvTag1, AtLec1, AtLec2, or AtWri1.
Figure 8:
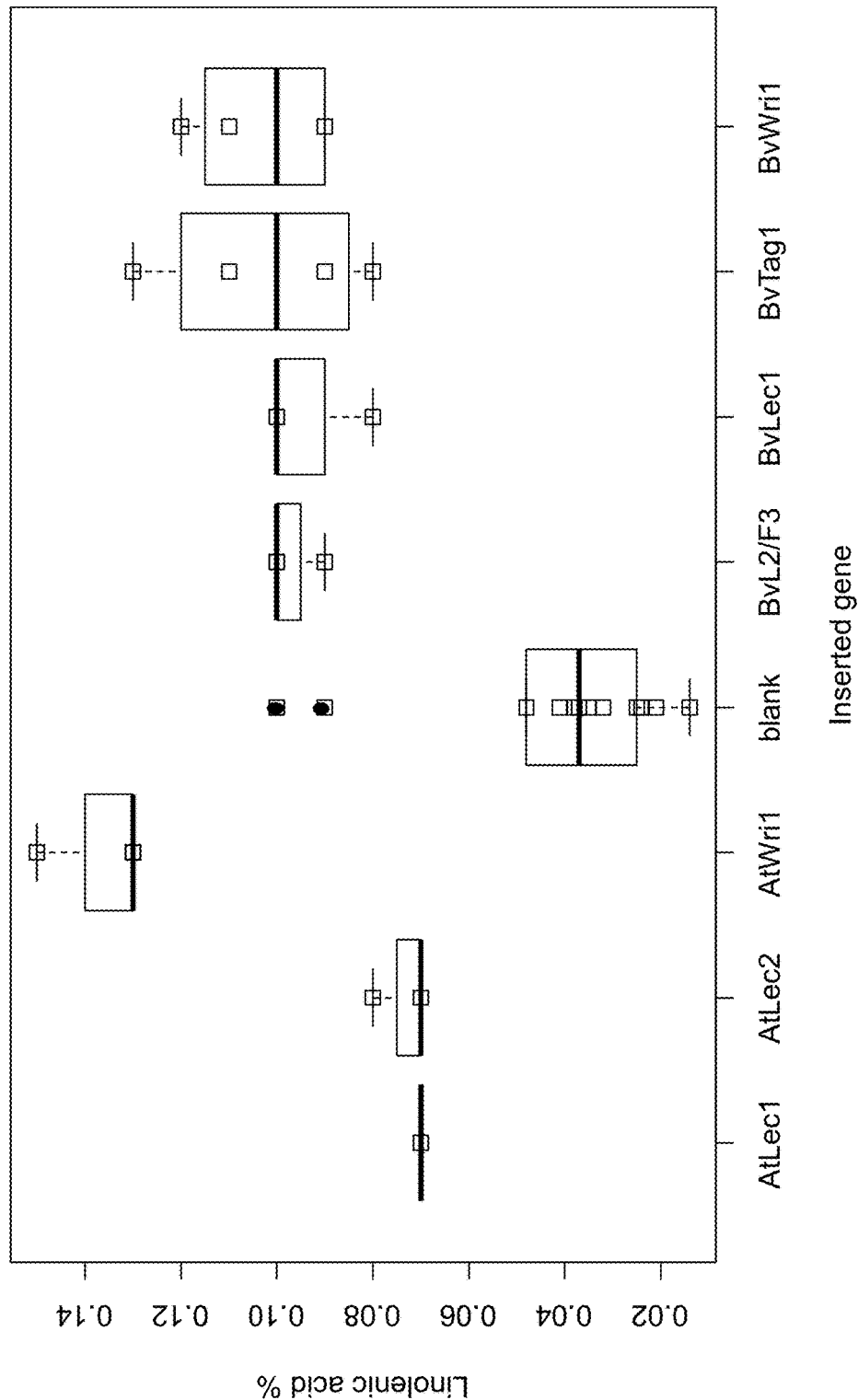
FIG. 8 shows the linolenic acid content in sugar beet roots transformed with either BvLec1, BvLec2/Fusca3, BvWri1, BvTag1, AtLec1, AtLec2, or AtWri1.

In Table 5 and FIG. 4, the wild-type (no vector) *N. benthamiana* and the empty vector (blank) *N. benthamiana* produce between approximately 2.5% to approximately 4% fatty acids by dry weight. As such, any genetically altered *N. benthamiana* plant that produces approximately 4.5% or higher fatty acids is considered producing higher amounts of fatty acids produced by the wild-type plant. In Table 5, such genetically altered *N. benthamiana* producing BvLec1 are 29-3, 29-7, 78-3, 134-9, 136-2, and 136-8. Such genetically altered *N. benthamiana* producing BvLec2/Fusca3 are 38-1, 43-1, 43-4, 45-2, 56-2, 65-1, 66-2, 66-4, and 89-5. Such genetically altered *N. benthamiana* producing BvWri1 are 24-2, 24-4, 27-4, 75-1, 77-3, and 125-2. Such genetically altered *N. benthamiana* producing BvTag1 are 53-5, 82-3, and 82-4. Such genetically altered *N. benthamiana* producing AtLec1 are 2-4 and 3-5. No genetically altered *N. benthamiana* producing AtLec2 produced sufficiently high enough amounts of fatty acid. Such genetically altered *N. benthamiana* producing AtWri1 are 16-1, 16-9, 22-5, and 23-5.

Figure 3:
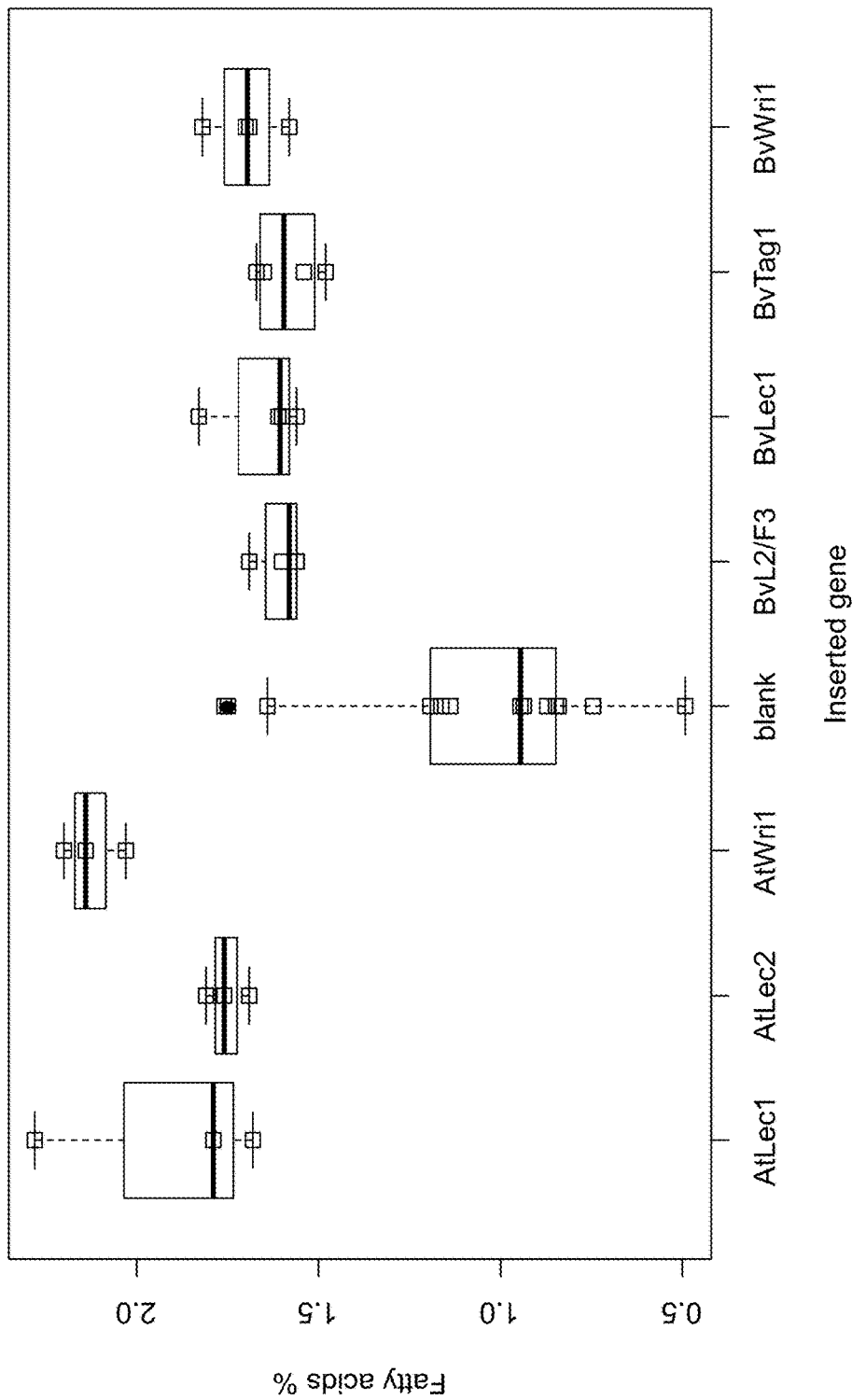
FIG. 3 shows the total fatty acid content (%) in sugar beet root samples transformed with either BvLec1, BvLec2/Fusca3, BvWri1, BvTag1, AtLec1, AtLec2, or AtWri1.

In Table 6 and FIG. 3, the wild-type (not transformed, no vector) *B. vulgaris* roots and the empty vector (blank) *B. vulgaris* hairy roots produced between approximately 0.4% to approximately 1.1% fatty acids by dry weight. As such, any genetically altered *B. vulgaris* hairy roots that produce approximately 1.5% or higher fatty acids is considered producing higher amounts of fatty acids than produced by the vector control plant. In Table 6, such genetically altered *B. vulgaris* hairy roots producing BvLec1 are 6-2, 6-7, 6-9, and 6-10. Such genetically altered *B. vulgaris* hairy roots producing BvLec2/Fusca3 are 8-3, 8-4, 8-9, and 8-10. Such genetically altered *B. vulgaris* hairy roots producing BvWri1 are 5-4, 5-5, 5-8, and 5-9. Such genetically altered *B. vulgaris* hairy roots producing BvTag1 are 7-1, 7-4, and 7-9. Such genetically altered *B. vulgaris* hairy roots producing AtLec1 are 1-4, 1-7, and 1-10. Such genetically altered *B. vulgaris* hairy roots producing AtLec2 are 2-4 and 2-9. Such genetically altered *B. vulgaris* hairy roots producing AtWri1 are 3-3, 3-4, and 3-5. In addition, as shown in FIG. 5, FIG. 6, FIG. 7 and FIG. 8, genetically altered *B. vulgaris* roots produced more palmitic acid, oleic acid, linoleic acid, and linolenic acid, respectively, when transformed with and transcribing BvLec1, BvLec2/Fusca3, BvWri1, BvTag1, AtLec1, AtLec2, and AtWri1 than wild-type *B. vulgaris* roots and the empty vector (blank) *B. vulgaris* hairy roots.

Figure 9:
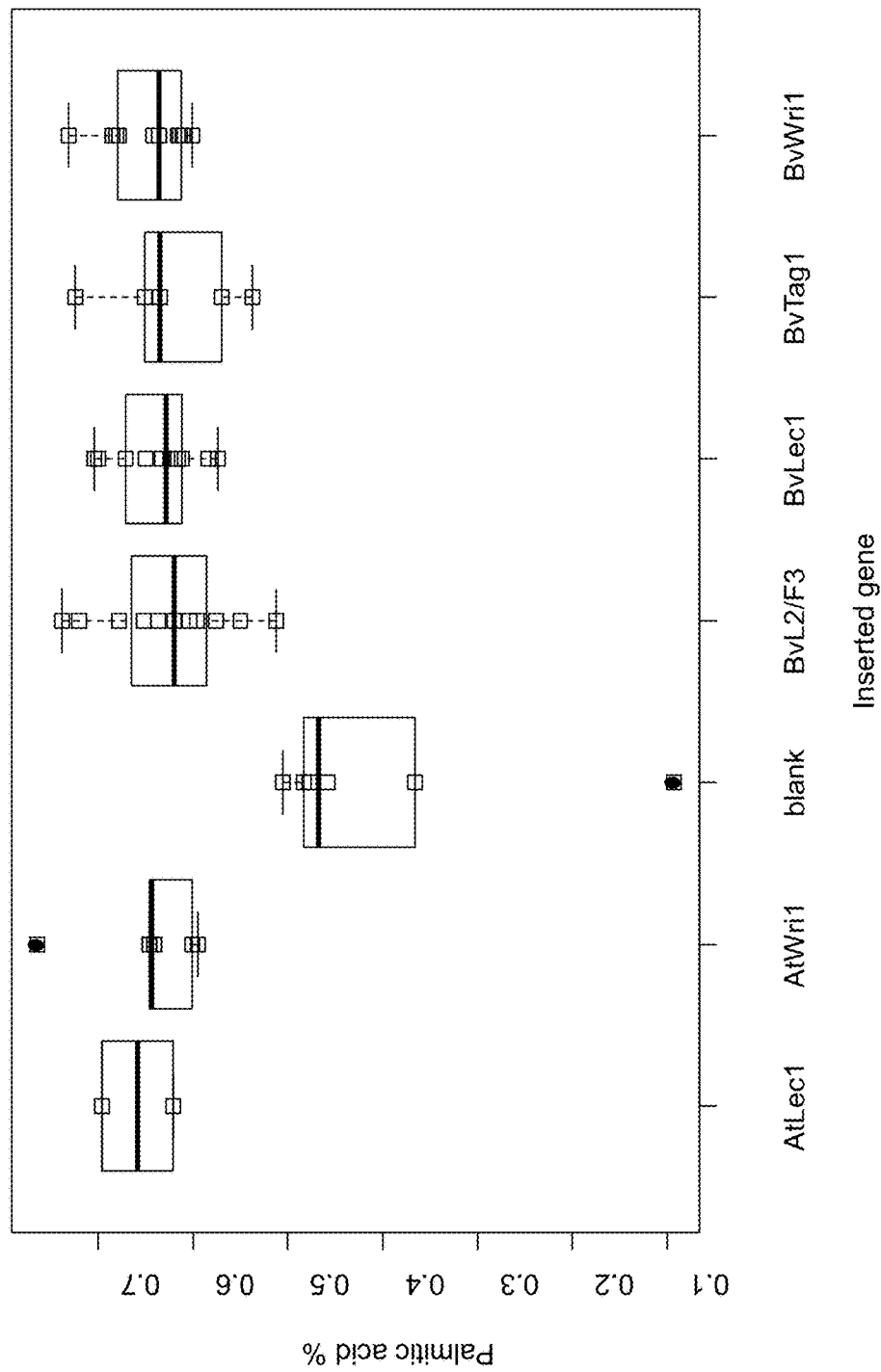
FIG. 9 shows the palmitic acid content in N. benthamiana transformed with either BvLec1, BvLec2/Fusca3, BvWri1, BvTag1, AtLec1, or AtWri1. The samples used in this assay had elevated fatty acid content of 4% or higher.
Figure 10:
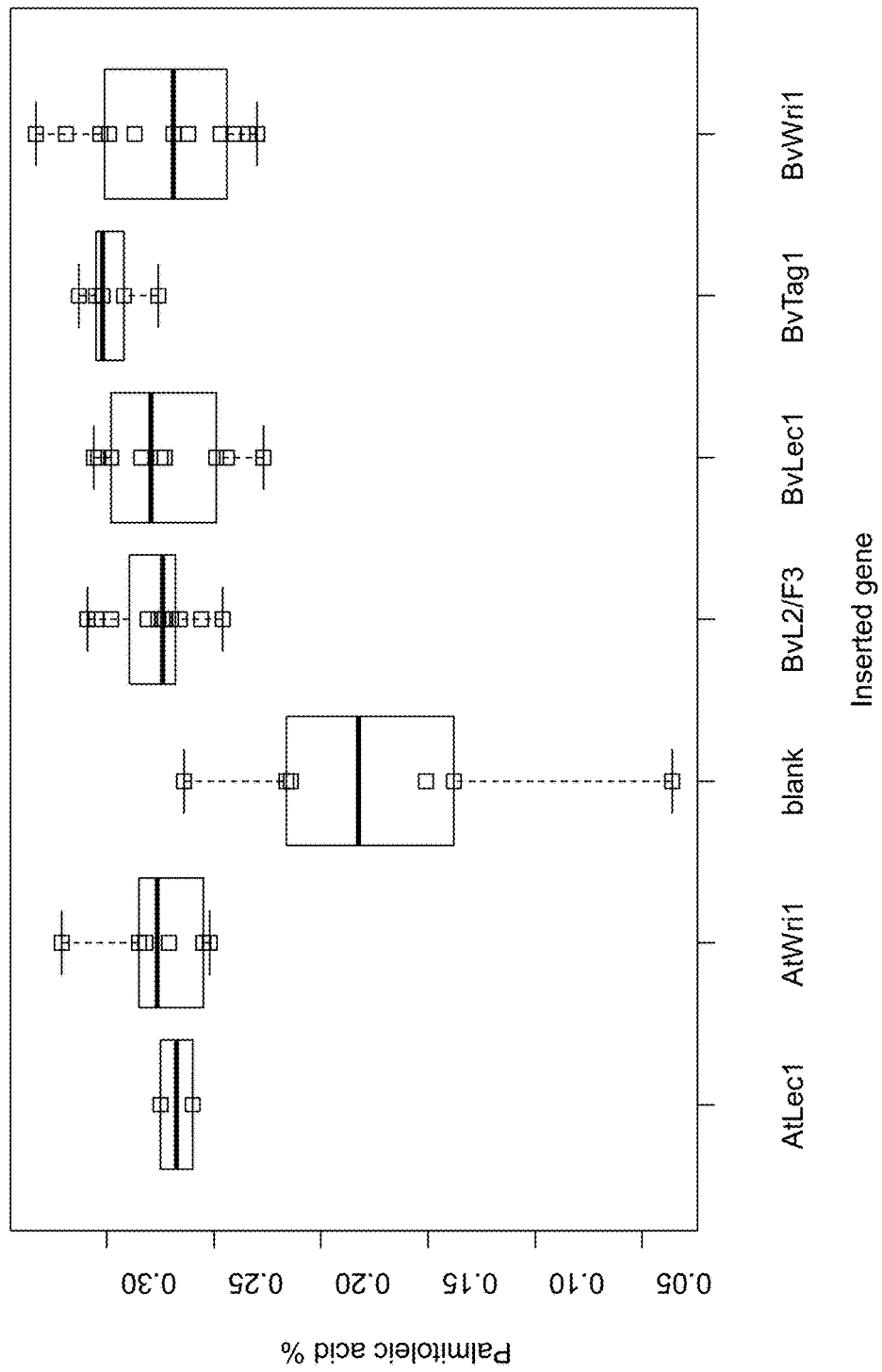
FIG. 10 shows the palmitoleic acid content in N. benthamiana transformed with either BvLec1, BvLec2/Fusca3, BvWri1, BvTag1, AtLec1, or AtWri1. The samples used in this assay had elevated fatty acid content of 4% or higher.
Figure 11:
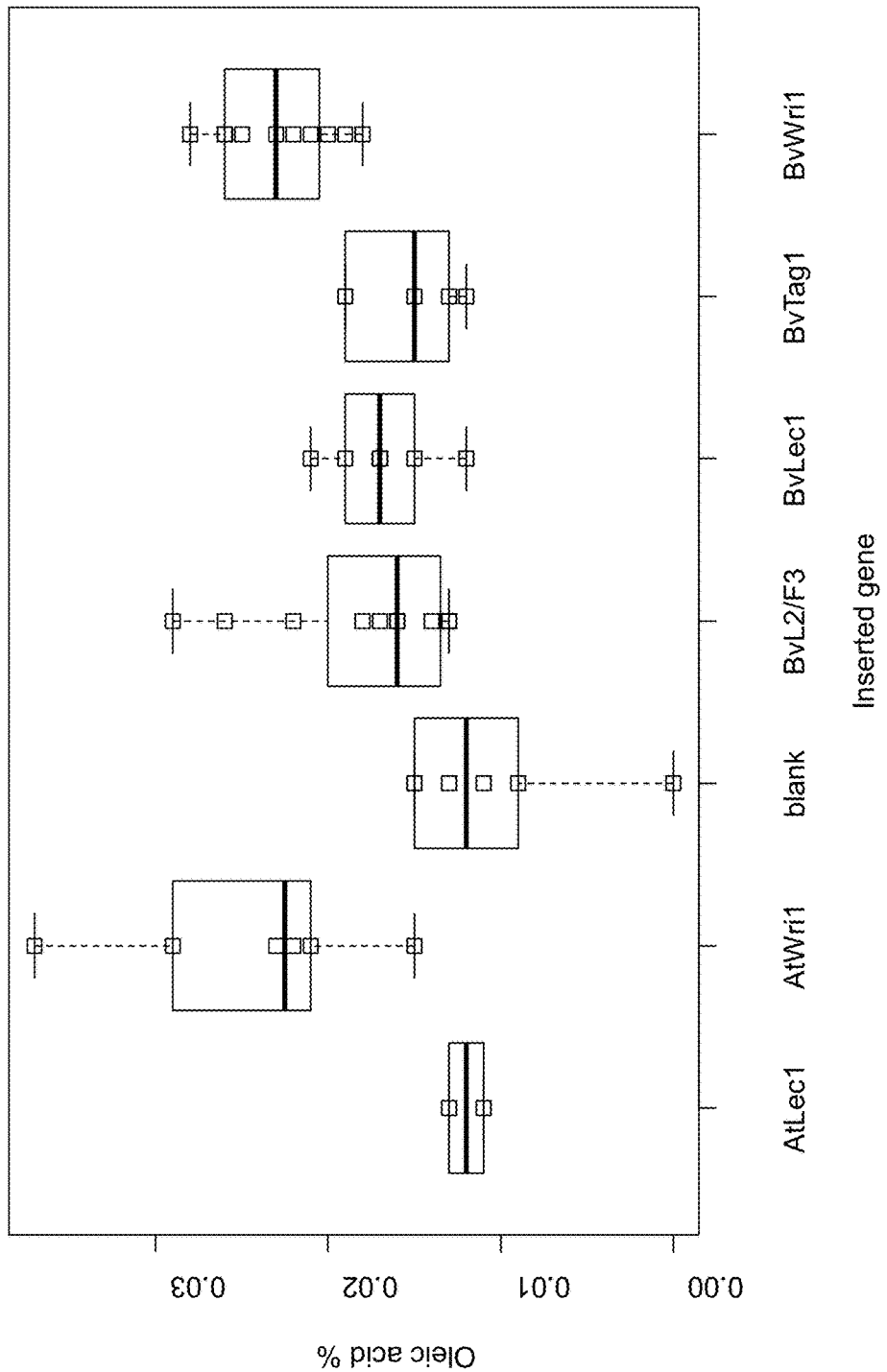
FIG. 11 shows the oleic acid content in N. benthamiana transformed with either BvLec1, BvLec2/Fusca3, BvWri1, BvTag1, AtLec1, or AtWri1. The samples used in this assay had elevated fatty acid content of 4% or higher.
Figure 12:
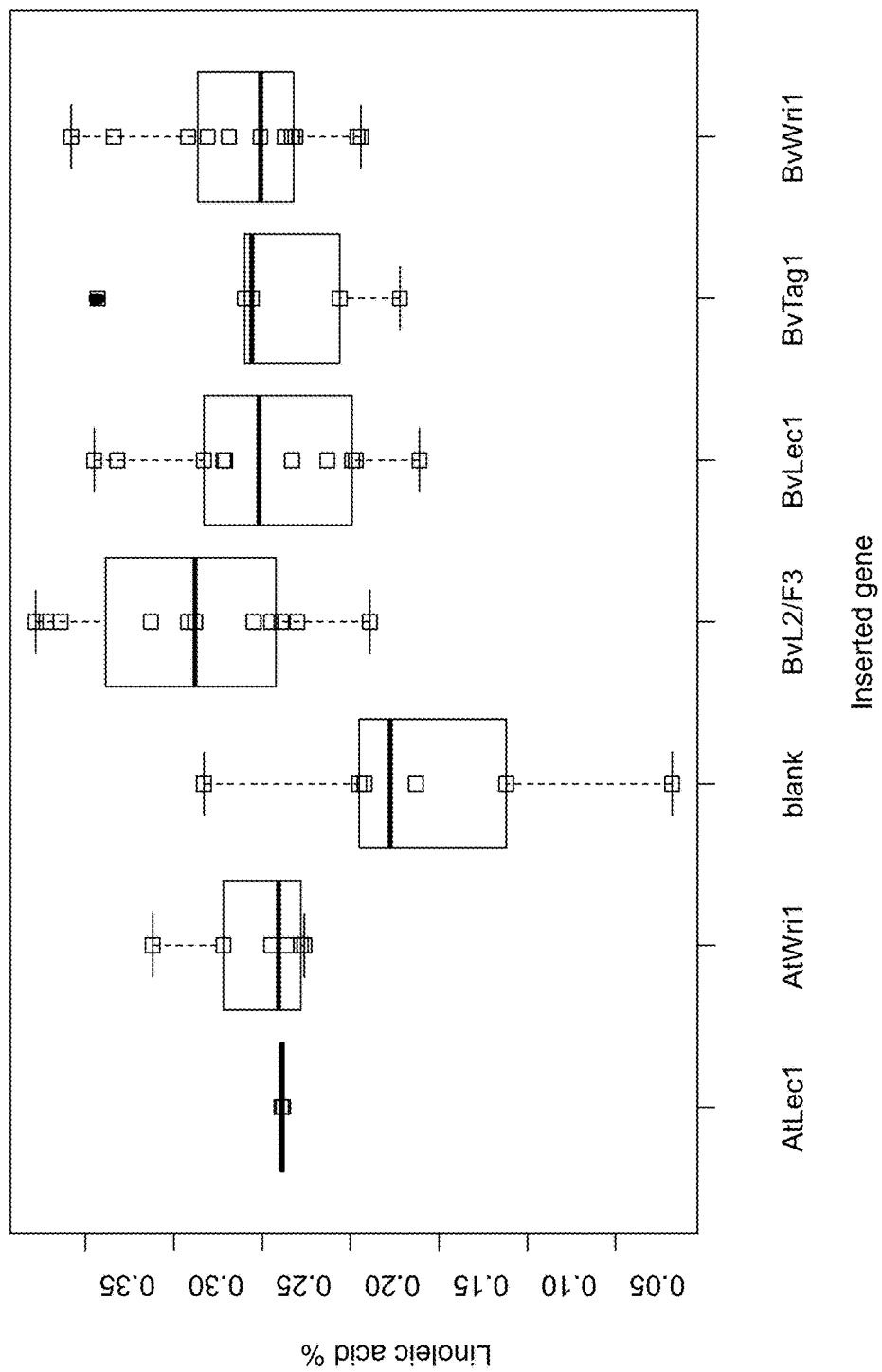
FIG. 12 shows the linoleic acid content in N. benthamiana transformed with either BvLec1, BvLec2/Fusca3, BvWri1, BvTag1, AtLec1, or AtWri1. The samples used in this assay had elevated fatty acid content of 4% or higher.
Figure 13:
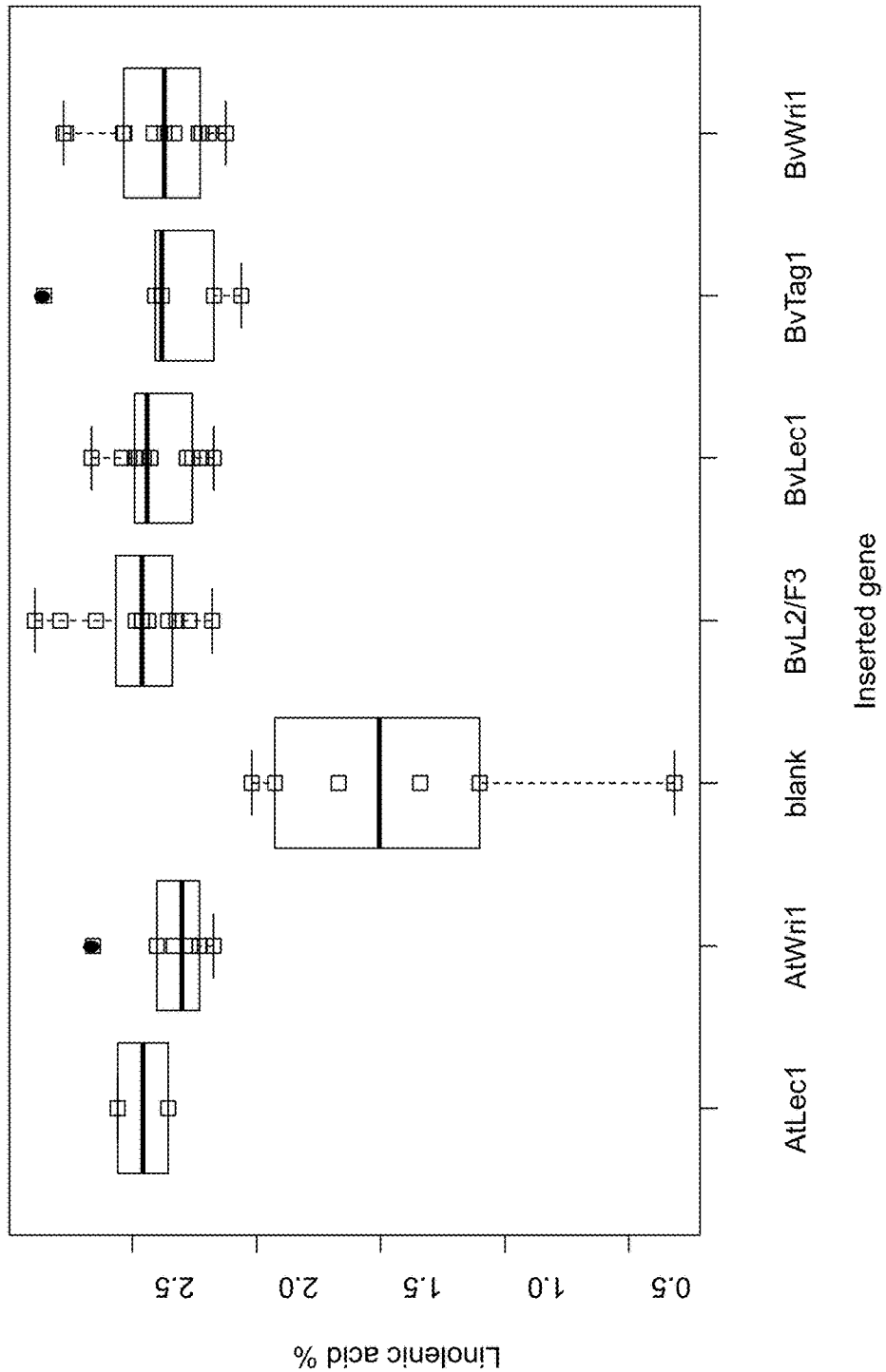
FIG. 13 shows the linolenic acid content in N. benthamiana transformed with either BvLec1, BvLec2/Fusca3, BvWri1, BvTag1, AtLec1, or AtWri1. The samples used in this assay had elevated fatty acid content of 4% or higher.

As shown in Table 5 and FIG. 13, the wild-type (no vector) *N. benthamiana* and the empty vector (blank) *N. benthamiana* produce between approximately 1.3% to approximately 2.0% linolenic acids by dry weight. As such, any genetically altered *N. benthamiana* plant that produces approximately 2.4% or higher linolenic acids is considered producing higher amounts of linolenic acids than produced by the wild-type plant. In Table 5, such genetically altered *N. benthamiana* producing BvLec1 are 29-3, 29-7, 78-3, 134-9, 136-2, and 136-8. Such genetically altered *N. benthamiana* producing BvLec2/Fusca3 are 38-1, 43-1, 43-4, 45-2, 56-2, 65-1, 66-2, 66-4, and 89-5. Such genetically altered *N. benthamiana* producing BvWri1 are 24-2, 24-4, 27-4, 75-1, 77-3, and 125-2. Such genetically altered *N. benthamiana* producing BvTag1 are 53-5, 82-3, and 82-4. Such genetically altered *N. benthamiana* producing AtLec1 are 2-4 and 3-5. No genetically altered *N. benthamiana* producing AtLec2 produced sufficiently high enough amounts of linolenic acid. Such genetically altered *N. benthamiana* producing AtWri1 are 16-1, 16-9, 22-5, and 23-5. This linolenic acid increase contrasts to a linolenic acid decrease reported by Andrianov, et al. (2010). In addition, as shown in FIG. 9, FIG. 10 and FIG. 12, the genetically modified *N. benthamiana* described herein (and those figures) produced increased amounts of palmitic acid, palmitoleic acid, and linoleic acid. Again, it is noted that Andrianov, et al. (2010) did not report that their *N. tabacum* plants transformed with either AtLec2 or AtTag1 produced increased amounts of palmitic acid, palmitoleic acid, or linoleic acid, possibly because their plants did not produce increased amounts of these fatty acids. In FIG. 11, an increase in oleic acid is observed in *N. benthamiana* leaves transformed with and expressing BvLec1, BvLec2/Fusca3, BvWri1, BvTag1, AtLec1, or AtWri1. As discussed above, Andrianov, et al. (2010) reported an increase in oleic acid in *N. tabacum* transformed with the AtLec2 or AtTag1.

Example 8. Obtaining Fats from Sugar Beets

Genetically altered sugar beet plants are generated which contain one or more expression cassettes containing individually BvLec1, BvLec2/Fusca3, BvWri1, BvTag1, AtLec1, AtLec2, and AtWri1 operably linked to the major latex-like protein promoter, BvSTI promoter or a constitutive promoter. Additionally, expression cassettes containing combinations of these genes (e.g., BvLec1 and BvTag1; BvLec2/Fusca3 and BvTag1; BvWri1 and BvTag1; BvLec1 and BvLec2/Fusca3; BvLec1 and BvWri1; BvLec2/Fusca3 and BvWri1; BvLec1, BvLec2/Fusca3, and BvTag1; BvLec2/Fusca3, BvWri1, and BvTag1; AtLec1 and BvTag1; AtLec2 and BvTag1; AtWri1 and BvTag1; AtLec1 and AtLec2; AtLec1 and AtWri1; AtLec2 and AtWri1; AtLec1, AtLec2, and BvTag1; AtLec2, AtWri1, and BvTag1) operably linked to the major latex-like protein promoter and/or BvSTI promoter and/or a constitutive promoter are also used to transform sugar beet plants (the expression cassette can contain one or more promoters operably linked to the polynucleotides encoding the proteins). The transformation process uses published regeneration methods (see, Ivic-Haymes and Smigocki, In-vitro *Cell. & Dev. Bio. Plant* 41:483-488 (2005)) with *Agrobacterium tumefaciens* or *A. rhizogenes* DNA transfer occurring on the sectioned sugar beet tissue edges followed by appropriate antibiotic selection (Ivic-Haymes and Smigocki, *Plant Cell Rep.* 23:699-704 (2005)).

The genetically altered sugar beet cells are then grown in the well-known manner that genetically altered sugar beet plants are produced which are then grown for a full season. The roots are harvested, and a fraction of the roots are analyzed for fatty acid content and profile using standard analytical chemistry techniques, and the remaining roots are replanted the following year to make seeds.

Example 9. Insect Feeding Resistance Via Leaf Feeding

The independently derived genetically altered *N. benthamiana* plants and genetically altered *B. vulgaris* hairy roots (described supra) with demonstrably high transcription levels of BvLec1, BvLec2/Fusca3, BvWri1, BvTag1, AtLec1, AtLec2, and AtWri1 and elevated levels of fatty acids (see Tables 5 and 6 supra) are used to assess the genetically altered plants' resistance to fall armyworms and beet armyworms which serve as a representative for other *Lepidoptera* insects. More specifically, these insect feeding assays are conducted to study the effect of the production of BvLec1, BvLec2/Fusca3, BvWri1, BvTag1, AtLec1, AtLec2, and AtWri1 proteins on the growth and development of these insects. Newly emerged fall armyworm (*Spodoptera frugiperda* J. E. Smith) and beet armyworm (*Spodoptera exigua* Hubner), generalist lepidopteran herbivores with a wide host range, are purchased from Benzon Research (Carlisle, Pa.) and are reared on the artificial diet provided by Benzon Research. The larval insects are maintained at room temperature for approximately one to approximately three days and are removed from the diet approximately two hours prior to the start of the insect feeding experiments. For leaf assays, a fully expanded leaf from a 4-month old greenhouse grown *Nicotiana* plant (either a genetically altered plant or a normal plant) is placed on water moistened filter paper in a Petri dish and is infested with weighed larva (second instar) for each insect. The Petri dish containing the leaf and insect larva are kept in the dark at room temperature, and larval weights and mortality are recorded daily until pupation. Each experiment is repeated between two to five times with each experiment containing between five and ten separate leaves (replicates) for that particular insect. The leaf assays are conducted with genetically altered *N. benthamiana* containing the pCAMBIA expression cassette and, the expression cassette containing individually, BvLEC1, BvLEC2/FUSCA3, BvWRI1, BvTAG1, AtLEC1, AtLEC2, and AtWRI1. The experiments are performed per the protocol set forth in Smigocki, et al., *PLoS ONE* 8(2): e57303, doi:10.1371 (2013) and Smigocki, et al., *Plant Cell Tiss. Org. Cult.*, 97:167-174 (2009). For sugar beet hairy root assays, roots are grown on filter papers placed on plant growth medium in Petri dishes for two weeks. The filter papers with the sugar beet hairy roots are placed in an empty Petri dish, and each dish is infested with weighed larva as described supra. The Petri dish containing the sugar beet hairy roots and insect larva are kept in the dark at room temperature, and larval weights and mortality are recorded daily. Larvae are weighed at the start of the experiment and only those larvae with non-significantly different weights are used in the bioassay. The experiments are performed per the protocol set forth in Smigocki, et al., *PLoS ONE* 8(2): e57303, doi:10.1371 (2013) and Smigocki, et al., *Plant Cell Tiss. Org. Cult.*, 97:167-174 (2009).

All statistical analysis is performed by one-way Analysis of Variance (ANOVA) using Analyse-it software (Analyze-it Software, Ltd., Leeds, United Kingdom). Results are expressed as mean±standard error (S.E.) for the number of replicates in each treatment. The acceptance level of statistical significance was $P<0.05$.

It is expected that any variation in weight, either decrease or increase, caused by feeding on genetically altered plants overexpressing BvLec1, BvLec2/Fusca3, BvWri1, BvTag1, AtLec1, AtLec2, and AtWri1 will alter the normal life cycle of the insect, thus changing the insect's dynamics and timing of the interaction with the transgenic economically valuable plant; a desirable strategy for enhancing insect tolerance.

Although this invention has been exemplified for purposes of illustration and description by reference to certain specific embodiments, it will be apparent to those skilled in the art that various modifications, alterations, and equivalents of the illustrated examples are possible. Any such changes, which derive directly from the teachings herein or do not depart from the spirit and scope of the invention, are deemed to be covered by this invention.

We, the inventors, claim:

1. A method for increasing the amount of at least one fatty acid produced in a genetically altered plant compared to the amount of the at least one fatty acid produced in a wild-type plant, the method comprising:
transforming a wild-type plant cell with a heterologous expression cassette comprising a heterologous promoter operably linked to a polynucleotide encoding at least one fatty acid biosynthesis protein to generate a transformed plant cell;
culturing said transformed plant cell to produce said genetically altered plant, wherein said genetically altered plant produces said at least one fatty acid biosynthesis protein and produces a higher amount of said at least one fatty acid compared to the amount of said at least one fatty acid produced by said wild-type plant; wherein said at least one fatty acid biosynthesis protein is selected from the group consisting of Beta vulgaris Leafy Cotyledon1 (BvLec1), Beta vulgaris Leafy Cotyledon2/Fusca3 (BvLec2/Fusca3), Beta vulgaris Wrinkled 1 (BvWri1), and a combination thereof; wherein said heterologous promoter is a constitutive promoter or a tissue-specific promoter; wherein said BvLec1 comprises an amino acid sequence of SEQ ID NO: 6 or a sequence at least 95% identical thereof; wherein said BvLec2/Fusca3 comprises an amino acid sequence of SEQ ID NO: 7 or a sequence at least 95% identical thereof; and wherein said BvWri1 comprises an amino acid sequence of SEQ ID NO: 8 or a sequence at least 95% identical thereof.

2. The method of claim 1, wherein said BvLec1 is encoded by a DNA sequence of SEQ ID NO: 2 or a sequence at least 90% identical thereof; wherein said BvLec2/Fusca3 is encoded by a DNA sequence of SEQ ID NO: 3 or a sequence at least 90% identical thereof; and wherein said BvWri1 is encoded by a DNA sequence of SEQ ID NO: 4 or a sequence at least 90% identical thereof.

3. The method of claim 1, wherein said genetically altered plant is a root crop plant or Nicotiana spp.

4. The method of claim 1, wherein said heterologous promoter is selected from the group consisting of CaMV 35S promoter, BvSTI promoter, and a By major latex-like protein promoter.

5. The method of claim 1, wherein said at least one fatty acid is selected from the group consisting of linolenic acid, linoleic acid, palmitic acid, palmitoleic acid, oleic acid, and a combination thereof.

6. A genetically altered plant produced by the method of claim 1, wherein said genetically altered plant transformed with at least one of the BvLec1, BvLec2/Fusca, or BvWri1 produces a higher amount of at least one fatty acid as compared to the amount of the at least one fatty acid produced by the corresponding wild-type plant not transformed with at least one of the BvLec1, BvLec2/Fusca, or BvWri1.

7. The genetically altered plant of claim 6, wherein said genetically altered plant is a root crop plant or Nicotiana spp.

8. The genetically altered plant of claim 6, wherein said heterologous promoter is selected from the group consisting of CaMV 35S promoter, a BvSTI promoter, and By major latex-like protein promoter.

9. The genetically altered plant of claim 6, wherein said at least one fatty acid is selected from the group consisting of linolenic acid, linoleic acid, palmitic acid, palmitoleic acid, oleic acid, and a combination thereof.

10. A genetically altered cell of said genetically altered plant of claim 6, wherein said genetically altered cell comprises said heterologous expression cassette.

11. A genetically altered pollen of said genetically altered plant of claim 6, wherein said genetically altered pollen comprises said heterologous expression cassette.

12. A genetically altered seed of said genetically altered plant of claim 6, wherein said genetically altered seed comprises said heterologous expression cassette.

13. A genetically altered plant or part thereof that produces a higher amount of at least one fatty acid compared to the amount of the at least one fatty acid produced by a wild-type plant, said genetically altered plant comprising a heterologous expression cassette, wherein said expression cassette comprises a heterologous promoter operably linked a polynucleotide encoding at least one fatty acid biosynthesis protein, wherein said at least one fatty acid biosynthesis protein is selected from the group consisting of BvLec1, BvLec2/Fusca3, BvWri1, and a combination thereof; wherein said genetically altered plant produces said at least one fatty acid biosynthesis protein encoded by said polynucleotide; wherein said produced at least one fatty acid biosynthesis protein increases the production of at least one fatty acid in said genetically altered plant compared to the amount of the at least one fatty acid produced by said wild-type plant; wherein said BvLec1 comprises an amino acid sequence of SEQ ID NO: 6 or a sequence at least 95% identical thereof; wherein said BvLec2/Fusca3 comprises an amino acid sequence of SEQ ID NO: 7 or a sequence at least 95% identical thereof; and wherein said BvWri1 comprises an amino acid sequence of SEQ ID NO: 8 or a sequence at least 95% identical thereof.

14. The genetically altered plant of claim 13, wherein said BvLec1 is encoded by a DNA sequence of SEQ ID NO: 2 or a sequence at least 90% identical thereof; wherein said BvLec2/Fusca3 has a DNA sequence of SEQ ID NO: 3 or a sequence at least 90% identical thereof; and wherein said BvWri1 is encoded by a DNA sequence of SEQ ID NO: 4 or a sequence at least 90% identical thereof.

15. The genetically altered plant of claim 13, wherein said genetically altered plant is a root crop plant or *Nicotiana* spp.

16. The genetically altered plant of claim 13, wherein said heterologous promoter is selected from the group consisting of CaMV 35S promoter, a BvSTI promoter, and By major latex-like protein promoter.

17. The genetically altered plant of claim 13, wherein said at least one fatty acid is selected from the group consisting of linolenic acid, linoleic acid, palmitic acid, palmitoleic acid, oleic acid, and a combination thereof.

18. A genetically altered cell of said genetically altered plant of claim 13, wherein said genetically altered cell comprises said heterologous expression cassette.

19. A genetically altered pollen of said genetically altered plant of claim 13, wherein said genetically altered pollen contains said heterologous expression cassette.

20. A genetically altered seed of said genetically altered plant of claim 13, wherein said genetically altered seed contains said heterologous expression cassette.

21. A method for increasing a genetically altered plant's resistance to an insect that feeds on said genetically altered plant compared to a wild-type plant's resistance to said insect feeding on said wild-type plant, the method comprising: transforming a wild-type plant cell with a heterologous expression cassette comprising a heterologous promoter operably linked to a polynucleotide encoding at least one fatty acid biosynthesis protein to generate a transformed plant cell; culturing said transformed plant cell to develop said genetically altered plant; wherein said genetically altered plant produces said at least one fatty acid biosynthesis protein; wherein said genetically altered plant produces said at least one fatty acid in an amount higher than the amount of said at least one fatty acid produced by said wild-type plant; wherein said genetically altered plant's resistance to said insect is increased compared to said wild-type plant's resistance to said insect; wherein said at least one fatty acid biosynthesis protein is BvWri1, wherein said BvWri1 comprises an amino acid sequence of SEQ ID NO: 8 or a sequence at least 95% identical thereof.

22. The method of claim 21, wherein said BvWri1 is encoded by a DNA sequence of SEQ ID NO: 4 or a sequence at least 90% identical thereof.

23. The method of claim 21, wherein said genetically altered plant is a root crop plant or *Nicotiana* spp.

24. The method of claim 21, wherein said heterologous promoter is selected from the group of constitutive promoter and a tissue-specific promoter.

25. The method of claim 24, wherein said heterologous promoter is selected from the group of CaMV 35S promoter, a BvSTI promoter, and By major latex-like protein promoter.

26. The method of claim 21, wherein said at least one fatty acid is selected from the group consisting of linolenic acid, linoleic acid, palmitic acid, palmitoleic acid, oleic acid, and a combination thereof.

27. A fatty acid produced by the genetically altered plant of claim 13, wherein said fatty acid comprises a detectable amount of said heterologous expression cassette encoding SEQ ID NO: 6 or a sequence at least 95% identical thereof, SEQ ID NO: 7 or a sequence at least 95% identical thereof; SEQ ID NO: 8 or a sequence at least 95% identical thereof, or a combination thereof.

* * * * *

SEQUENCE LISTING

```
<160> NUMBER OF SEQ ID NOS: 42

<210> SEQ ID NO 1
<211> LENGTH: 4089
<212> TYPE: DNA
<213> ORGANISM: Beta vulgaris

<400> SEQUENCE: 1
ctcgaggatc cttgatttgt tttttttgacc aatgagcatt aagagtgatc aagcacatgg      60
atttcaaaat atcaatggtt ggatttttat cattctcaaa tcaatggtta aagttaaata     120
ttctattttc taatttctaa atttataatt ctatactcta gtattgattt gataagcaat     180
tagtaatcta cttaaattcc taaactatta ttaataatat aaattaataa aaattataaa     240
cttagaagtt taattattat ttttaatttc aaacaagttg attgatgtaa atatgattat     300
gaatgacgtg aaacagttaa ggcaaagttg tagtttagta actttaaaaa ttagtagtgt     360
tattataact taatagaaat tataaacttt caaaattaaa ttagtattat tgattttttaa    420
```

```
gaaattatta ttctaaattt ataaattcag aaatatgtga acatgttaca tgcggtgatt    480
acggattaat ttaatgctaa catgtaagac gtaaacacaat aacagttaac ctactactac   540
tacttgtata ggtcttacat taatacttaa gttattggtt ataaacttat attaatatac    600
ggttatttct tctattaagc gtagatttct tataaccttta cttatacaat tatttactat   660
tactcaacta taatttgatt gtattcagtt aagtgaactt atataagtta taacaagcct    720
taatcagtac tagaccttag cttatactat actacatata cgaattttcg cttttcatat    780
tagtatctta ctgataagca ataaagttta ctacgacata gtaacaataa ttaactactt    840
gtttcaattc aattagatga tttgggtttt gaaatgaatt taacttaaag atgattacct    900
tagatagagt attgttatct tctattaagt taattactta acttacatta atacatttgt    960
tgatattatc caatatccat tatcttaaac gaacttacgc catcttgaat tagctaatcg   1020
acttacattg atacatcgat ctaatccaat attaacttgt atcaattcaa attagatgtt   1080
ttgagtttca atatgcaact taacttagag acgattaact aaatgaagc attgttatat    1140 tgaaccaatc tactgagtta tactattcta catctgtttg aattagatgc tttcggttcc   1200
gaaatgaatt caacttaaag atgattaact taagtagagt actgttatta tcttgaatta   1260
aacttagggt actgttaaac tagatgtttt gagtttcaat atgaatttaa cttagagacg   1320
attaacttaa atggagtatt gttatattga accaatctac tgagttccat tgttctacat   1380
ttgttgcaac tcaattagat gctttcagtt ccgaaatgaa ttcaacttaa aaagatgatt   1440
aacttaagta gagtactatt attatattga actagtttat cgacttacat tgatacactc   1500
attcaaataa caacatgttt caatttaagt aaacgttttg agtttcaatt actttatcga   1560
cttacgtcga tacattcatc taatctaata tcaattgtaa tttctttag tttggctaag    1620 atatgtgagt ttcaaattga atataaattg ttagcgatta acttaaatgg agtaatgtta   1680
tcttgatttc acttatcgat tcacatagat accttgagct aatccataat caacttattt   1740
tacgtcgatt atagatatat taatccattg aactaataca ctaagagtaa gacactaaca   1800
tagatttgtc ttattccaaa tcatatatat taagtaataa agtacacttt aaccgatgtc   1860
actttcattc acgtttttat gaagtacaac tattttttg aggcaattgt ggaagtgccg    1920
acaacactta tttgttgcat taattttag ccggacccga aaacacctga ccaaaaccga    1980
catgaagcac aattttttccc gaacaaatac aagagtgtga ttaacttcta cccgaaccga   2040
tgcgattatt gtcgaagtta tgtggttttt tgtcaataac tgaaataaac cgaaacgaaa   2100
ctgaaaataa ccgcaacaaa ttttaactga tatggattca accgttggtt ggtttaactg   2160
tttggttaaa actgatttaa actgcaactg aactgaactg aaaatggaaa gggaaaaaac   2220
tgaattaaac tgaactgaaa agtttgttaa ctgaactgaa ctgttaatta tttcaactaa   2280
tacaaactga actgatatca actgaactgt ttggttataa ccataactga actgttgaac   2340
tgaattgaca cctctaattg caacggcaac aatagaactg ttacagtagc ccaatctaca   2400
aaactaaatt gacaagaact gttgcattag atactcctac tacaacggta cgtaataatg   2460
tgttgcacta gtaaatttta gcctttgcct ttgattaaaa atgttgtagt gacacatcac   2520
aataaaatca aatctaatga atatgctata acaaacaat tgttccaaaa tcaactattc    2580
ttacgaaata ctctttttcga gggacgacat ttttctgaaa cacccctaagc gacgttattg  2640 actctaatac atagatgaaa tatcaataaa aagggattta tgaggtat tctttaattt    2700 tttttttaaga acatatgagg taccatagta ttttaaaaat caatccatgt gcccctaact  2760
```

```
tcgtaatgta tccatcatat atatcccttt tttttttagg ggtccatcat atatatcctt    2820
aatgcatgac tatcaaacat tagatatgtc ttaatccccc cctaacaatc aaccaaaatt    2880
ccaaaattgg ttactctatt tgttcctatt acaccttcca ccaatctcaa caaattttgg    2940
cattctggtt aagtactcga aggactactt aacgaaatat ttgatgtttg ttagccatta    3000
aggtttatgt gttggattca ttataaatgg tttgaaaagt ttattatcat ctttattaaa    3060
agttcaatag tacctcatga gaactctcta taaatcaact atattagtta tcaataataa    3120
gatacattcg gattctattt ggcaacacat ttaagtcacc tcaaatgaat aggtgttaaa    3180
agtttaagtc acctaaaata aatagtcatg attaaagtaa gagcttaaat caaatgtaag    3240
ctaaaaaatt gactgaaatt aaattggtat caagtataac atcttaattt aaggtgttaa    3300
aattttcaac taacttatca attgagcttt tttcatcaat ttcacctcta tttcagcttt    3360 gttttagct tatatttcca aaattgccaa taggtctcat ttatacctaa gatattcaac     3420
aatcctggct ctcttcctgc tcgttcattc caaatttccc aaatgtaatc agattaaagc    3480
agtagtgatc ggatcattgc agacttttcg gtagaataac tgaataagtg tactgagata    3540
gtgtcaaaat actgttattt aagttttcta taagtactaa aatatgaatt agttcaacat    3600
catcttatat tgtcggccaa taagattgcc cactgtataa taatataaaa caaaatcaca    3660
gaggtgatat cgccttaaaa aaaaaaaatc atagatgtga attaatgtaa ccgagcataa    3720
atcaactgtt tccttttttt ttaaaagaga aatcaactgt ttcctagaaa caattgaata    3780
ttatatggtg gtttattgtt tcaaatttca gaaaacaaa aaaaaaaag cctttgctac       3840 ttacttacat agttgcatct atataaaggg cacctagccc aaccatttta cttacctaaa    3900
ctgtctgtgt ttgcaccact ctcatctaaa aaatctgtga aagtgagcgt ttcaaaattt    3960
tcaaaagatg cacataacag gtaaattaga agttgaagtt gatatcaatt gtcatggtga    4020
tattttccat gaaattttta gcaccaggcc acatgatgtc tccaccatgt cacctgagaa    4080
tatccatgg                                                           4089

<210> SEQ ID NO 2
<211> LENGTH: 708
<212> TYPE: DNA
<213> ORGANISM: Beta vulgaris

<400> SEQUENCE: 2
atgaccaatc acagcagcaa caacaacaat aataatgcta actttaacaa tggaagtcat      60
agcaaccaca ataatcactc agcatcaact gacaccgata caacgagtg cacagtgcgg     120 gagcaggatc gttttatgcc tatcgccaat gtcatacgca tcatgcgcaa gattcttcca     180
ccccatgcaa aaatatctga tgatgctaag gaaacaatcc aggagtgtgt gtcagagtac     240
ataagcttta taacagggga agcaaacgag aggtgccaga gggagcaacg taagaccata     300
accgcagaag atgtgctatg ggccatgagc aagctgggct cgacgacta cattgagcca     360 ctaacacttt acttgcaccg ctacagggag ctggagggg aacgtggttc catccgcact      420
tgtgagccac tccttaaact gagtagggca gccatggatc agtatgcagc ttatggacca     480
gtctttcaca ttggaccacc gccgcctcat cctcatcatc caggctatta tggagggcca     540
gggccgtcat ctgtgaatgg atacttgaaa gaagcttctg ctgctggtgt gtctgataca     600
gttacagttg ggcctccgca acctcctact gctgctgcta ctgtcgctgc tggagggccg     660
gctgctaatt ctgttaccag tttcgagcca tatggtcacc acaactaa                  708
```

<210> SEQ ID NO 3
<211> LENGTH: 900
<212> TYPE: DNA
<213> ORGANISM: Beta vulgaris

<400> SEQUENCE: 3

| | | | | | |
|---|---|---|---|---|---|
| atgatgatga | tggtggagga | gagagaaaat | gagaaaaatg | atgtccttgg | atttgcccaa | 60 |
| aataatggag | tcgttgtttt | taacagtggt | aactcagcga | gtgggaacgg | tggactcggt | 120 |
| aactcgggtg | agtcaactcg | ggcgattttg | gggtgttttg | gagaacataa | aattcagagg | 180 |
| aagaaaagga | tggctagaca | agaaggtcc | tctgttagtc | tcttacccctt | tgcttcctct | 240 |
| cacgtgccta | ctctctctct | tcctgcacgt | gtcattgatc | caaggagatt | gagatttta | 300 |
| tttcaaaagc | aacttcagaa | cagtgacgtc | agctcgctaa | ggaggatggt | gctaccaaag | 360 |
| aaagcagccg | agtcacacct | ccctactcta | gaaactaagg | agggaattta | tatcagcatg | 420 |
| gatgatatgg | acggggtgca | cctctggaac | ttcaagtata | ggttttggcc | aaataacaac | 480 |
| agtcgaatgt | atgtcctaga | aaacacaggg | actttgtta | gtgctcatcg | tttgcagctt | 540 |
| ggggacttca | taatggtcta | tcaagacatc | attaaccta | actatgtgat | tcaagccaag | 600 |
| aagacttcac | aacaagaaat | atacaatgac | tatacaacca | atgcagttag | tgatcattac | 660 |
| tatcaagttc | acaattttga | gataaaccgg | tacaatcaat | taagctggaa | cgatcccgga | 720 |
| aaaatggagg | atgataataa | gacatgcatg | tcatttgtat | atgagacaac | cagcttctcc | 780 |
| aatgactcgc | ctttcgattt | tcttggcggg | tccatgacta | actactactc | agggatgggg | 840 |
| ggtcatggct | tcgaaaactt | cggatctgtt | gacaatttgt | ccttgacga | cttctattga | 900 |

<210> SEQ ID NO 4
<211> LENGTH: 1374
<212> TYPE: DNA
<213> ORGANISM: Beta vulgaris

<400> SEQUENCE: 4

| | | | | | |
|---|---|---|---|---|---|
| atgaagaaga | ggtcaattac | taatgcagca | gactcctctg | ctgcatcgcc | ttcgtcgcgc | 60 |
| tcgtcgtcgt | cgtcttcgtc | ttcatgtgtc | gttgattatc | ataatcatca | tcataataat | 120 |
| caattaattg | atgatactaa | tgacaaggat | gaaaaacctc | ctaagcctaa | aagaactcga | 180 |
| agaaaaaaag | tttctgttaa | tcctaaaacc | caaaaatgtc | ccattaatcc | ccctgctaat | 240 |
| cgtcgtagct | ccatttacag | aggtgtcaca | agacatagat | ggacaggaag | atttgaagct | 300 |
| catttatggg | ataaaagttc | ttggaatagc | attcaaaaca | aaaaaggaag | acaagtttat | 360 |
| ttgggagcat | atgatagtga | agtagatgca | gcgcggacgt | acgatctggc | ggcacttaag | 420 |
| tactggggac | cagagaccac | attaaattt | cctatagaaa | actatacaaa | agaggttgaa | 480 |
| gaaatgcaaa | atgcaaccaa | ggaagaatac | ttggcatcat | tgagacgaag | aagtagcgga | 540 |
| ttttcgagag | gtgtctctaa | ataccgtggt | gtggctaggc | atcatcacaa | tggaagatgg | 600 |
| gaggcacgaa | ttgggcgcgt | tttcgggaac | aaatacctct | acttgggcac | tttcagttca | 660 |
| caagaagaag | cagcagcagc | gtatgatctg | gctgcaatag | agtacagagg | ggcaaatgca | 720 |
| gtaactaatt | tcgacattag | caactacatt | gggcgtgtaa | agaatctttt | gcctaaaggt | 780 |
| caatcacaac | aaccgaatcc | caagcaaact | aaaaccataa | ccccacaacg | gcagcaacaa | 840 |
| caacaaataa | aacaacagga | agaggaggaa | gaacttcaag | aaccagtagc | gaaacacaga | 900 |
| gatttagcag | atatagagca | acaggaacaa | catatggtaa | tcccatctca | gctcgaggag | 960 |
| tctaagctta | ttaattccat | tgatgatcac | tcgtccatgc | ttgggatgaa | tcggccagag | 1020 |

| gatgaccgag aaaacccgtg gagcttttgc ttgatgtgg gagtttacga ccccctctta | 1080 |
| gtccccgata tccccttcga agaagatggc aggttgcttg atttatttga tcagacgggt | 1140 |
| tttgaagata atattgatat gatctttgag ggggaaggaa acttgattag tatgggtggc | 1200 |
| actttctttg atggcacaga ggtcataggt tgtgaaacca taattaaaac ttccgaggat | 1260 |
| ttagataaga agattgagac tttgccaaag gtagaggaaa attcacttta ttttcttcg | 1320 |
| tcgtctccat catcaccttc ttcaataact agcttagtct catgtcaatt gtaa | 1374 |

```
<210> SEQ ID NO 5
<211> LENGTH: 1557
<212> TYPE: DNA
<213> ORGANISM: Beta vulgaris

<400> SEQUENCE: 5
```

| atggcgattt cggattcgcc tgagacgatc ggtgttacca cggcgactga tcatggcgaa | 60 |
| tccgttcgta ggcgaccgat tagtgcacca gctggtaatg gtaaagcttc tacatcttca | 120 |
| tcttcaatgg cggaagaatt ggaggatttc aagaatgtct ccaatggcgg tgatgttgac | 180 |
| aggattgttg ataataatga acggatttat tctgaaaatg tgagcggtga aggtgaaggt | 240 |
| gaagagagag ttgtcaatgg tggaggagct caaaactctg agaatgcgat tcggtactcg | 300 |
| tatcgaccgt cgtctcccgc tcatttgaag gttaaggaga gtcctcttag ctctgacgcc | 360 |
| attttcagac agagtcatgc tggtctcttc aatctttgtg tagtggtact tgttgctgtg | 420 |
| aacagccggc ttatcattga aaatctcatg aagtatggtt tgctcataag agctggtttc | 480 |
| tggtttagct caaagtcact aagggattgg cctcttttca tgtgctgtct ttctctccca | 540 |
| gtttttccat tggctgcttt cttcgtagaa aagttggcac aaagaaggcg catatctgat | 600 |
| ccggtggttg tcctacttca tatattgatt gccacaatta caatcttgta tccagttttt | 660 |
| gtaatactca ggtgcgattc tgctgttctt tttggtgtca cattgatgct ttttgcttgc | 720 |
| accatgtggt taaagttggt atcatatgca catacaaatt atgatatgag agcaattgcc | 780 |
| aaagcatcta ttaaggatga tgaactagat atggaacttc cttatgatgt caacttcgac | 840 |
| agtttggtgt acttcatggt tgctcccacg ctatgttacc agccaagtta tcctaatact | 900 |
| gcatgtattc gaaaaggatg ggtggctcga caagtattga aattggtgat atttactgga | 960 |
| ttaatggggt tcatcgtaga gcaatatatc aatccaattg tacaaaattc acagcatcca | 1020 |
| ctgaaaggaa acttgttgta tgcaatagaa agagttttga agctctcagt cccgaatttg | 1080 |
| tacgtgtggc tgtgcatgtt ctattgcttt ttccacctct ggttgaacat attggctgag | 1140 |
| cttcttaagt ttggagaccg tgagttttac aaagattggt ggaatgcaag aacattcgaa | 1200 |
| gagtattgga ggatgtggaa tatgcctgta cataaatgga tggttcgcca tgtatacttt | 1260 |
| ccttgcttgc gcaatggaat accgaaggga gttgcagtgt tgattgcttt cctcatatct | 1320 |
| gccatatttc atgagctatg cattgctgtc ccttgccata tcttcaaact ttgggctttt | 1380 |
| ctgggcatta tgtttcaggt tcccttggtt ttgcttacaa atttcctgca aaggaagttc | 1440 |
| cagaactcca tgcttggaaa tatgatcttc tggttcatct tcagcatatt tggtcaacca | 1500 |
| atgtgtgttc ttctttatta ccatgatcta atgaatcgca aaggcaattt agcatga | 1557 |

```
<210> SEQ ID NO 6
<211> LENGTH: 235
<212> TYPE: PRT
<213> ORGANISM: Beta vulgaris

<400> SEQUENCE: 6
```

Met Thr Asn His Ser Asn Asn Asn Asn Ala Asn Phe Asn
1               5                   10                  15

Asn Gly Ser His Ser Asn His Asn His Ser Ala Ser Thr Asp Thr
                20                  25                  30

Asp Asn Asn Glu Cys Thr Val Arg Glu Gln Asp Arg Phe Met Pro Ile
            35                  40                  45

Ala Asn Val Ile Arg Ile Met Arg Lys Ile Leu Pro Pro His Ala Lys
        50                  55                  60

Ile Ser Asp Asp Ala Lys Glu Thr Ile Gln Glu Cys Val Ser Glu Tyr
65                  70                  75                  80

Ile Ser Phe Ile Thr Gly Glu Ala Asn Glu Arg Cys Gln Arg Glu Gln
                85                  90                  95

Arg Lys Thr Ile Thr Ala Glu Asp Val Leu Trp Ala Met Ser Lys Leu
                100                 105                 110

Gly Phe Asp Asp Tyr Ile Glu Pro Leu Thr Leu Tyr Leu His Arg Tyr
            115                 120                 125

Arg Glu Leu Glu Gly Glu Arg Gly Ser Ile Arg Thr Cys Glu Pro Leu
        130                 135                 140

Leu Lys Leu Ser Arg Ala Ala Met Asp Gln Tyr Ala Ala Tyr Gly Pro
145                 150                 155                 160

Val Phe His Ile Gly Pro Pro Pro His Pro His Pro Gly Tyr
                165                 170                 175

Tyr Gly Gly Pro Gly Pro Ser Ser Val Asn Gly Tyr Leu Lys Glu Ala
            180                 185                 190

Ser Ala Ala Gly Val Ser Asp Thr Val Thr Val Gly Pro Pro Gln Pro
        195                 200                 205

Pro Thr Ala Ala Ala Thr Val Ala Ala Gly Gly Pro Ala Ala Asn Ser
        210                 215                 220

Val Thr Ser Phe Glu Pro Tyr Gly His His Asn
225                 230                 235

<210> SEQ ID NO 7
<211> LENGTH: 299
<212> TYPE: PRT
<213> ORGANISM: Beta vulgaris

<400> SEQUENCE: 7

Met Met Met Met Val Glu Glu Arg Glu Asn Glu Lys Asn Asp Val Leu
1               5                   10                  15

Gly Phe Ala Gln Asn Asn Gly Val Val Val Phe Asn Ser Gly Asn Ser
                20                  25                  30

Ala Ser Gly Asn Gly Gly Leu Gly Asn Ser Gly Glu Ser Thr Arg Ala
            35                  40                  45

Ile Leu Gly Cys Phe Gly Glu His Lys Ile Gln Arg Lys Lys Arg Met
        50                  55                  60

Ala Arg Gln Arg Arg Ser Ser Val Ser Leu Leu Pro Phe Ala Ser Ser
65                  70                  75                  80

His Val Pro Thr Leu Ser Leu Pro Ala Arg Val Ile Asp Pro Arg Arg
                85                  90                  95

Leu Arg Phe Leu Phe Gln Lys Gln Leu Gln Asn Ser Asp Val Ser Ser
            100                 105                 110

Leu Arg Arg Met Val Leu Pro Lys Lys Ala Ala Glu Ser His Leu Pro
        115                 120                 125

Thr Leu Glu Thr Lys Glu Gly Ile Tyr Ile Ser Met Asp Asp Met Asp

```
                130                 135                 140
Gly Val His Leu Trp Asn Phe Lys Tyr Arg Phe Trp Pro Asn Asn Asn
145                 150                 155                 160

Ser Arg Met Tyr Val Leu Glu Asn Thr Gly Asp Phe Val Ser Ala His
                165                 170                 175

Arg Leu Gln Leu Gly Asp Phe Ile Met Val Tyr Gln Asp Ile Ile Asn
            180                 185                 190

Leu Asn Tyr Val Ile Gln Ala Lys Lys Thr Ser Gln Gln Glu Ile Tyr
            195                 200                 205

Asn Asp Tyr Thr Thr Asn Ala Val Ser Asp His Tyr Tyr Gln Val His
            210                 215                 220

Asn Phe Glu Ile Asn Arg Tyr Asn Gln Leu Ser Trp Asn Asp Pro Gly
225                 230                 235                 240

Lys Met Glu Asp Asp Asn Lys Thr Cys Met Ser Phe Val Tyr Glu Thr
                245                 250                 255

Thr Ser Phe Ser Asn Asp Ser Pro Phe Asp Phe Leu Gly Gly Ser Met
            260                 265                 270

Thr Asn Tyr Tyr Ser Gly Met Gly Gly His Gly Phe Glu Asn Phe Gly
            275                 280                 285

Ser Val Asp Asn Leu Ser Leu Asp Asp Phe Tyr
            290                 295
```

<210> SEQ ID NO 8
<211> LENGTH: 457
<212> TYPE: PRT
<213> ORGANISM: Beta vulgaris

<400> SEQUENCE: 8

```
Met Lys Lys Arg Ser Ile Thr Asn Ala Ala Asp Ser Ser Ala Ala Ser
1               5                   10                  15

Pro Ser Arg Ser Ser Ser Ser Ser Ser Ser Cys Val Val Asp
                20                  25                  30

Tyr His Asn His His His Asn Asn Gln Leu Ile Asp Asp Thr Asn Asp
                35                  40                  45

Lys Asp Glu Lys Pro Pro Lys Pro Lys Arg Thr Arg Arg Lys Lys Val
            50                  55                  60

Ser Val Asn Pro Lys Thr Gln Lys Cys Pro Ile Asn Pro Pro Ala Asn
65                  70                  75                  80

Arg Arg Ser Ser Ile Tyr Arg Gly Val Thr Arg His Arg Trp Thr Gly
                85                  90                  95

Arg Phe Glu Ala His Leu Trp Asp Lys Ser Ser Trp Asn Ser Ile Gln
                100                 105                 110

Asn Lys Lys Gly Arg Gln Val Tyr Leu Gly Ala Tyr Asp Ser Glu Val
            115                 120                 125

Asp Ala Ala Arg Thr Tyr Asp Leu Ala Ala Leu Lys Tyr Trp Gly Pro
130                 135                 140

Glu Thr Thr Leu Asn Phe Pro Ile Glu Asn Tyr Thr Lys Glu Val Glu
145                 150                 155                 160

Glu Met Gln Asn Ala Thr Lys Glu Glu Tyr Leu Ala Ser Leu Arg Arg
                165                 170                 175

Arg Ser Ser Gly Phe Ser Arg Gly Val Ser Lys Tyr Arg Gly Val Ala
            180                 185                 190

Arg His His His Asn Gly Arg Trp Glu Ala Arg Ile Gly Arg Val Phe
            195                 200                 205
```

```
Gly Asn Lys Tyr Leu Tyr Leu Gly Thr Phe Ser Ser Gln Glu Glu Ala
    210                 215                 220

Ala Ala Ala Tyr Asp Leu Ala Ile Glu Tyr Arg Gly Ala Asn Ala
225                 230                 235                 240

Val Thr Asn Phe Asp Ile Ser Asn Tyr Ile Gly Arg Val Lys Asn Leu
                245                 250                 255

Leu Pro Lys Gly Gln Ser Gln Pro Asn Pro Lys Gln Thr Lys Thr
            260                 265                 270

Ile Thr Pro Gln Arg Gln Gln Gln Gln Ile Lys Gln Glu Glu
            275                 280                 285

Glu Glu Glu Leu Gln Glu Pro Val Ala Lys His Arg Asp Leu Ala Asp
290                 295                 300

Ile Glu Gln Gln Glu Gln His Met Val Ile Pro Ser Gln Leu Glu Glu
305                 310                 315                 320

Ser Lys Leu Ile Asn Ser Ile Asp Asp His Ser Ser Met Leu Gly Met
                325                 330                 335

Asn Arg Pro Glu Asp Asp Arg Glu Asn Pro Trp Ser Phe Cys Leu Asp
                340                 345                 350

Val Gly Val Tyr Asp Pro Leu Leu Val Pro Asp Ile Pro Phe Glu Glu
                355                 360                 365

Asp Gly Arg Leu Leu Asp Leu Phe Asp Gln Thr Gly Phe Glu Asp Asn
                370                 375                 380

Ile Asp Met Ile Phe Glu Gly Glu Gly Asn Leu Ile Ser Met Gly Gly
385                 390                 395                 400

Thr Phe Phe Asp Gly Thr Glu Val Ile Gly Cys Glu Thr Ile Ile Lys
                405                 410                 415

Thr Ser Glu Asp Leu Asp Lys Lys Ile Glu Thr Leu Pro Lys Val Glu
                420                 425                 430

Glu Asn Ser Leu Tyr Phe Ser Ser Ser Pro Ser Ser Pro Ser Ser
            435                 440                 445

Ile Thr Ser Leu Val Ser Cys Gln Leu
    450                 455

<210> SEQ ID NO 9
<211> LENGTH: 518
<212> TYPE: PRT
<213> ORGANISM: Beta vulgaris

<400> SEQUENCE: 9

Met Ala Ile Ser Asp Ser Pro Glu Thr Ile Gly Val Thr Thr Ala Thr
1               5                   10                  15

Asp His Gly Glu Ser Val Arg Arg Pro Ile Ser Ala Pro Ala Gly
            20                  25                  30

Asn Gly Lys Ala Ser Thr Ser Ser Ser Met Ala Glu Glu Leu Glu
            35                  40                  45

Asp Phe Lys Asn Val Ser Asn Gly Gly Asp Val Asp Arg Ile Val Asp
        50                  55                  60

Asn Asn Glu Arg Ile Tyr Ser Glu Asn Val Ser Gly Glu Gly Glu Gly
65                  70                  75                  80

Glu Glu Arg Val Val Asn Gly Gly Ala Gln Asn Ser Glu Asn Ala
                85                  90                  95

Ile Arg Tyr Ser Tyr Arg Pro Ser Ser Pro Ala His Leu Lys Val Lys
            100                 105                 110

Glu Ser Pro Leu Ser Ser Asp Ala Ile Phe Arg Gln Ser His Ala Gly
        115                 120                 125
```

```
Leu Phe Asn Leu Cys Val Val Leu Val Ala Val Asn Ser Arg Leu
    130                 135                 140

Ile Ile Glu Asn Leu Met Lys Tyr Gly Leu Leu Ile Arg Ala Gly Phe
145                 150                 155                 160

Trp Phe Ser Ser Lys Ser Leu Arg Asp Trp Pro Leu Phe Met Cys Cys
                165                 170                 175

Leu Ser Leu Pro Val Phe Pro Leu Ala Ala Phe Phe Val Glu Lys Leu
            180                 185                 190

Ala Gln Arg Arg Arg Ile Ser Asp Pro Val Val Leu Leu His Ile
        195                 200                 205

Leu Ile Ala Thr Ile Thr Ile Leu Tyr Pro Val Phe Val Ile Leu Arg
210                 215                 220

Cys Asp Ser Ala Val Leu Phe Gly Val Thr Leu Met Leu Phe Ala Cys
225                 230                 235                 240

Thr Met Trp Leu Lys Leu Val Ser Tyr Ala His Thr Asn Tyr Asp Met
                245                 250                 255

Arg Ala Ile Ala Lys Ala Ser Ile Lys Asp Asp Glu Leu Asp Met Glu
            260                 265                 270

Leu Pro Tyr Asp Val Asn Phe Asp Ser Leu Val Tyr Phe Met Val Ala
        275                 280                 285

Pro Thr Leu Cys Tyr Gln Pro Ser Tyr Pro Asn Thr Ala Cys Ile Arg
290                 295                 300

Lys Gly Trp Val Ala Arg Gln Val Leu Lys Leu Val Ile Phe Thr Gly
305                 310                 315                 320

Leu Met Gly Phe Ile Val Glu Gln Tyr Ile Asn Pro Ile Val Gln Asn
                325                 330                 335

Ser Gln His Pro Leu Lys Gly Asn Leu Leu Tyr Ala Ile Glu Arg Val
            340                 345                 350

Leu Lys Leu Ser Val Pro Asn Leu Tyr Val Trp Leu Cys Met Phe Tyr
        355                 360                 365

Cys Phe Phe His Leu Trp Leu Asn Ile Leu Ala Glu Leu Leu Lys Phe
370                 375                 380

Gly Asp Arg Glu Phe Tyr Lys Asp Trp Trp Asn Ala Arg Thr Phe Glu
385                 390                 395                 400

Glu Tyr Trp Arg Met Trp Asn Met Pro Val His Lys Trp Met Val Arg
                405                 410                 415

His Val Tyr Phe Pro Cys Leu Arg Asn Gly Ile Pro Lys Gly Val Ala
            420                 425                 430

Val Leu Ile Ala Phe Leu Ile Ser Ala Ile Phe His Glu Leu Cys Ile
        435                 440                 445

Ala Val Pro Cys His Ile Phe Lys Leu Trp Ala Phe Leu Gly Ile Met
450                 455                 460

Phe Gln Val Pro Leu Val Leu Thr Asn Phe Leu Gln Arg Lys Phe
465                 470                 475                 480

Gln Asn Ser Met Leu Gly Asn Met Ile Phe Trp Phe Ile Phe Ser Ile
                485                 490                 495

Phe Gly Gln Pro Met Cys Val Leu Leu Tyr Tyr His Asp Leu Met Asn
            500                 505                 510

Arg Lys Gly Asn Leu Ala
        515
```

<210> SEQ ID NO 10
<211> LENGTH: 794

```
<212> TYPE: DNA
<213> ORGANISM: Beta vulgaris

<400> SEQUENCE: 10
actatgaaag aaaggaagta ataaaaatag cattttctca cgtatcgtcg atagatttta      60
caaaatttta tattgtatta gatttatcta aaatttccat gttgtactct aacctttaa     120 acgttgcaaa atatctctat acacgatatg aaacagtgaa ctttgagact ttcttaccct    180
gtagacgtag agtaggattt ctgagccttg ttagttgact gaggtttgag atataacttg    240
agaaaataaa tgctaagtga ggtttggagt aggaatttct attaataggg gtattttgtg    300
tgatgtgtcg aaagtttagg ggaacgatct ataaaattca aaaatgtcgg atgcaacata    360
aaatttcata aaatacaaaa acaataggta gcacaaaaaa tcataaaaat attagttgat    420
tgccaaccaa caactcatcc taggtcatgt tttatacgca acaaatgaat attttatacc    480
tcataaataa tatctatttc ttacatttaa aatgaaacgg aggaagtatg ttgatgatga    540
gcaatataaa actcttatat aattaaattc gcacgatgat tgtatgctaa attgctaatc    600
aattattgaa acgaaaagg gcccaagtgc ccatatgctt aatttatgta cgatttaatt     660
tcctccacta gcttgcatga ttttaaaacc agcatacaaa ccttctataa atactagcat    720
tcttcagcta ctaactctca tccccaacat ccctcaaaca actatcagta acatacacac    780
caaacaaaaa caac                                                     794

<210> SEQ ID NO 11
<211> LENGTH: 717
<212> TYPE: DNA
<213> ORGANISM: Arabidopsis thaliana

<400> SEQUENCE: 11
atggaacgtg gagctcccct ctctcactat cagctaccaa aatccatctc tgaattgaac      60
ttggaccagc acagcaacaa cccaacccca atgaccagct cagtcgtagt agccggcgcc    120
ggtgacaaga acaatggtat cgtggtccag cagcaaccac catgtgtggc tcgtgagcaa    180
gaccaataca tgccaatcgc aaacgtcata agaatcatgc gtaaaacctt accgtctcac    240
gccaaaatct ctgacgacgc caaagaaacg attcaagaat gtgtctccga gtacatcagc    300
ttcgtgaccg gtgaagccaa cgagcgttgc aacgtgagc aacgtaagac cataactgct     360
gaagatatcc tttgggctat gagcaagctt gggttcgata actacgtgga ccccctcacc    420
gtgttcatta accggtaccg tgagatagag accgatcgtg ttctgcact tagaggtgag     480 ccaccgtcgt tgagacaaac ctatggagga atggtattg ggtttcacgg cccatctcat     540
ggcctacctc ctccgggtcc ttatggttat ggtatgttgg accaatccat ggttatggga    600
ggtggtcggt actaccaaaa cgggtcgtcg ggtcaagatg aatccagtgt tggtggtggc    660
tcttcgtctt ccattaacgg aatgccggct tttgaccatt atggtcagta taagtga       717

<210> SEQ ID NO 12
<211> LENGTH: 1092
<212> TYPE: DNA
<213> ORGANISM: Arabidopsis thaliana

<400> SEQUENCE: 12
atggataact tcttaccctt tccctcttct aacgcaaact ctgtccaaga actctctatg      60
gatcctaaca caatcgctc gcacttcaca acagtcccta cttatgatca tcatcaggct    120
cagcctcatc acttcttgcc tccgttttca tacccggtgg agcagatggc ggcggtgatg    180
```

```
aatcctcagc cggtttactt atcggagtgt tatcctcaga tcccggttac gcaaaccgga      240
agtgaattcg gttctctggt tggtaatcct tgtttgtggc aagagagagg tggttttctt      300
gatccgcgta tgacgaagat ggcaaggatc aacaggaaaa acgccatgat gagatcaaga      360
aacaactcta gccctaattc tagtccaagt gagttggttg attcaaagag acagctgatg      420
atgcttaact tgaaaaataa cgtgcagatc tccgacaaga aagatagcta ccaacagtcc      480
acatttgata caagaagct tagggttttg tgtgagaagg aattgaagaa cagcgatgtt      540
gggtcactcg ggaggatagt tctaccaaag agagatgcag aagcaaatct tccgaagcta      600
tctgataaag aaggaatcgt tgtacagatg agagatgttt tctctatgca gtcttggtct      660
ttcaaataca gttttggtc caataacaag agcagaatgt atgtcctcga aacacagga      720 gaatttgtga agcaaaatgg agctgagata ggagactttt taacaatata cgaggacgaa      780
agcaagaatc tctacttcgc catgaatgga aattcgggaa acaaaatga aggaagagaa      840 aatgagtcga gggaaaggaa ccactacgaa gaggcaatgc ttgattacat accaagagac      900
gaagaggaag cttccattgc aatgctcatc ggaaatctaa acgatcacta tcccatccct      960
aacgatctca tggacctcac cactgacctt cagcaccatc aagccacgtc ctcatcaatg     1020
ccacctgagg atcacgcgta cgtgggttca tccgatgatc aggtgagctt taacgacttt     1080
gagtggtggt ga                                                         1092

<210> SEQ ID NO 13
<211> LENGTH: 1293
<212> TYPE: DNA
<213> ORGANISM: Arabidopsis thaliana

<400> SEQUENCE: 13
atgaagaagc gcttaaccac ttccacttgt tcttcttctc catcttcctc tgtttcttct       60
tctactacta cttcctctcc tattcagtcg gaggctccaa ggcctaaacg agccaaaagg      120
gctaagaaat cttctccttc tggtgataaa tctcataacc cgacaagccc tgcttctacc      180
cgacgcagct ctatctacag aggagtcact agacatagat ggactgggag attcgaggct      240
catctttggg acaaaagctc ttggaattcg attcagaaca agaaaggcaa acaagtttat      300
ctgggagcat atgacagtga agaagcagca gcacatacgt acgatctggc tgctctcaag      360
tactggggac ccgacaccat cttgaatttt ccggcagaga cgtacacaaa ggaattggaa      420
gaaatgcaga gagtgacaaa ggaagaatat ttggcttctc tccgccgcca gagcagtggt      480
ttctccagag gcgtctctaa atatcgcggc gtcgctaggc atcaccacaa cggaagatgg      540
gaggctcgga tcggaagagt gtttgggaac aagtacttgt acctcggcac ctataatacg      600
caggaggaag ctgctgcagc atatgacatg gctgcgattg agtatcgagg cgcaaacgcg      660
gttactaatt tcgacattag taattacatt gaccggttaa agaagaaagg tgttttcccg      720
ttccctgtga accaagctaa ccatcaagag ggtattcttg ttgaagccaa acaagaagtt      780
gaaacgagag aagcgaagga agagcctaga gaagaagtga acaacagta cgtggaagaa      840 ccaccgcaag aagaagaaga aaggaagaa gagaaagcag agcaacaaga agcagagatt      900
gtaggatatt cagaagaagc agcagtggtc aattgctgca tagactcttc aaccataatg      960
gaaatggatc gttgtgggga caacaatgag ctggcttgga acttctgtat gatggataca     1020
gggttttctc cgttttttgac tgatcagaat ctcgcgaatg agaatcccat agagtatccg     1080
gagctattca atgagttagc atttgaggac aacatcgact tcatgttcga tgatgggaag     1140
cacgagtgct tgaacttgga aaatctggat tgttgcgtgg tgggaagaga gagcccaccc     1200
```

```
tcttcttctt caccattgtc ttgcttatct actgactctg cttcatcaac aacaacaaca    1260
acaacctcgg tttcttgtaa ctatttggtc tga                                 1293
```

<210> SEQ ID NO 14
<211> LENGTH: 238
<212> TYPE: PRT
<213> ORGANISM: Arabidopsis thaliana

<400> SEQUENCE: 14

```
Met Glu Arg Gly Ala Pro Phe Ser His Tyr Gln Leu Pro Lys Ser Ile
1               5                   10                  15

Ser Glu Leu Asn Leu Asp Gln His Ser Asn Asn Pro Thr Pro Met Thr
            20                  25                  30

Ser Ser Val Val Val Ala Gly Ala Gly Asp Lys Asn Asn Gly Ile Val
        35                  40                  45

Val Gln Gln Gln Pro Pro Cys Val Ala Arg Glu Gln Asp Gln Tyr Met
    50                  55                  60

Pro Ile Ala Asn Val Ile Arg Ile Met Arg Lys Thr Leu Pro Ser His
65                  70                  75                  80

Ala Lys Ile Ser Asp Asp Ala Lys Glu Thr Ile Gln Glu Cys Val Ser
                85                  90                  95

Glu Tyr Ile Ser Phe Val Thr Gly Glu Ala Asn Glu Arg Cys Gln Arg
            100                 105                 110

Glu Gln Arg Lys Thr Ile Thr Ala Glu Asp Ile Leu Trp Ala Met Ser
        115                 120                 125

Lys Leu Gly Phe Asp Asn Tyr Val Asp Pro Leu Thr Val Phe Ile Asn
    130                 135                 140

Arg Tyr Arg Glu Ile Glu Thr Asp Arg Gly Ser Ala Leu Arg Gly Glu
145                 150                 155                 160

Pro Pro Ser Leu Arg Gln Thr Tyr Gly Gly Asn Gly Ile Gly Phe His
                165                 170                 175

Gly Pro Ser His Gly Leu Pro Pro Gly Pro Tyr Gly Tyr Gly Met
            180                 185                 190

Leu Asp Gln Ser Met Val Met Gly Gly Gly Arg Tyr Tyr Gln Asn Gly
        195                 200                 205

Ser Ser Gly Gln Asp Glu Ser Ser Val Gly Gly Ser Ser Ser Ser
    210                 215                 220

Ile Asn Gly Met Pro Ala Phe Asp His Tyr Gly Gln Tyr Lys
225                 230                 235
```

<210> SEQ ID NO 15
<211> LENGTH: 363
<212> TYPE: PRT
<213> ORGANISM: Arabidopsis thaliana

<400> SEQUENCE: 15

```
Met Asp Asn Phe Leu Pro Phe Pro Ser Ser Asn Ala Asn Ser Val Gln
1               5                   10                  15

Glu Leu Ser Met Asp Pro Asn Asn Asn Arg Ser His Phe Thr Thr Val
            20                  25                  30

Pro Thr Tyr Asp His His Gln Ala Gln Pro His His Phe Leu Pro Pro
        35                  40                  45

Phe Ser Tyr Pro Val Glu Gln Met Ala Ala Val Met Asn Pro Gln Pro
    50                  55                  60

Val Tyr Leu Ser Glu Cys Tyr Pro Gln Ile Pro Val Thr Gln Thr Gly
```

```
                65                  70                  75                  80
        Ser Glu Phe Gly Ser Leu Val Gly Asn Pro Cys Leu Trp Gln Glu Arg
                        85                  90                  95

Gly Gly Phe Leu Asp Pro Arg Met Thr Lys Met Ala Arg Ile Asn Arg
                    100                 105                 110

Lys Asn Ala Met Met Arg Ser Arg Asn Asn Ser Ser Pro Asn Ser Ser
                    115                 120                 125

Pro Ser Glu Leu Val Asp Ser Lys Arg Gln Leu Met Met Leu Asn Leu
                130                 135                 140

Lys Asn Val Gln Ile Ser Asp Lys Lys Asp Ser Tyr Gln Gln Ser
        145                 150                 155                 160

Thr Phe Asp Asn Lys Lys Leu Arg Val Leu Cys Glu Lys Glu Leu Lys
                        165                 170                 175

Asn Ser Asp Val Gly Ser Leu Gly Arg Ile Val Leu Pro Lys Arg Asp
                    180                 185                 190

Ala Glu Ala Asn Leu Pro Lys Leu Ser Asp Lys Glu Gly Ile Val Val
                    195                 200                 205

Gln Met Arg Asp Val Phe Ser Met Gln Ser Trp Ser Phe Lys Tyr Lys
                210                 215                 220

Phe Trp Ser Asn Asn Lys Ser Arg Met Tyr Val Leu Glu Asn Thr Gly
        225                 230                 235                 240

Glu Phe Val Lys Gln Asn Gly Ala Glu Ile Gly Asp Phe Leu Thr Ile
                        245                 250                 255

Tyr Glu Asp Glu Ser Lys Asn Leu Tyr Phe Ala Met Asn Gly Asn Ser
                    260                 265                 270

Gly Lys Gln Asn Glu Gly Arg Glu Asn Glu Ser Arg Glu Arg Asn His
                    275                 280                 285

Tyr Glu Glu Ala Met Leu Asp Tyr Ile Pro Arg Asp Glu Glu Glu Ala
                    290                 295                 300

Ser Ile Ala Met Leu Ile Gly Asn Leu Asn Asp His Tyr Pro Ile Pro
        305                 310                 315                 320

Asn Asp Leu Met Asp Leu Thr Thr Asp Leu Gln His Gln Ala Thr
                        325                 330                 335

Ser Ser Ser Met Pro Pro Glu Asp His Ala Tyr Val Gly Ser Ser Asp
                    340                 345                 350

Asp Gln Val Ser Phe Asn Asp Phe Glu Trp Trp
                    355                 360

<210> SEQ ID NO 16
<211> LENGTH: 430
<212> TYPE: PRT
<213> ORGANISM: Arabidopsis thaliana

<400> SEQUENCE: 16

Met Lys Lys Arg Leu Thr Thr Ser Thr Cys Ser Ser Ser Pro Ser Ser
1               5                   10                  15

Ser Val Ser Ser Ser Thr Thr Ser Ser Pro Ile Gln Ser Glu Ala
                20                  25                  30

Pro Arg Pro Lys Arg Ala Lys Arg Ala Lys Lys Ser Ser Pro Ser Gly
            35                  40                  45

Asp Lys Ser His Asn Pro Thr Ser Pro Ala Ser Thr Arg Arg Ser Ser
        50                  55                  60

Ile Tyr Arg Gly Val Thr Arg His Arg Trp Thr Gly Arg Phe Glu Ala
65                  70                  75                  80
```

-continued

```
His Leu Trp Asp Lys Ser Ser Trp Asn Ser Ile Gln Asn Lys Lys Gly
                 85                  90                  95

Lys Gln Val Tyr Leu Gly Ala Tyr Asp Ser Glu Glu Ala Ala Ala His
            100                 105                 110

Thr Tyr Asp Leu Ala Ala Leu Lys Tyr Trp Gly Pro Asp Thr Ile Leu
            115                 120                 125

Asn Phe Pro Ala Glu Thr Tyr Thr Lys Glu Leu Glu Glu Met Gln Arg
        130                 135                 140

Val Thr Lys Glu Glu Tyr Leu Ala Ser Leu Arg Gln Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
            180                 185                 190

Leu Tyr Leu Gly Thr Tyr Asn Thr Gln Glu Glu Ala Ala Ala Ala Tyr
        195                 200                 205

Asp Met Ala Ala Ile Glu Tyr Arg Gly Ala Asn Ala Val Thr Asn Phe
    210                 215                 220

Asp Ile Ser Asn Tyr Ile Asp Arg Leu Lys Lys Lys Gly Val Phe Pro
225                 230                 235                 240

Phe Pro Val Asn Gln Ala Asn His Gln Glu Gly Ile Leu Val Glu Ala
                245                 250                 255

Lys Gln Glu Val Glu Thr Arg Glu Ala Lys Glu Glu Pro Arg Glu Glu
            260                 265                 270

Val Lys Gln Gln Tyr Val Glu Glu Pro Pro Gln Glu Glu Glu Glu Lys
        275                 280                 285

Glu Glu Glu Lys Ala Glu Gln Gln Glu Ala Glu Ile Val Gly Tyr Ser
    290                 295                 300

Glu Glu Ala Ala Val Val Asn Cys Cys Ile Asp Ser Ser Thr Ile Met
305                 310                 315                 320

Glu Met Asp Arg Cys Gly Asp Asn Asn Glu Leu Ala Trp Asn Phe Cys
                325                 330                 335

Met Met Asp Thr Gly Phe Ser Pro Phe Leu Thr Asp Gln Asn Leu Ala
            340                 345                 350

Asn Glu Asn Pro Ile Glu Tyr Pro Glu Leu Phe Asn Glu Leu Ala Phe
        355                 360                 365

Glu Asp Asn Ile Asp Phe Met Phe Asp Asp Gly Lys His Glu Cys Leu
    370                 375                 380

Asn Leu Glu Asn Leu Asp Cys Cys Val Val Gly Arg Glu Ser Pro Pro
385                 390                 395                 400

Ser Ser Ser Ser Pro Leu Ser Cys Leu Ser Thr Asp Ser Ala Ser Ser
                405                 410                 415

Thr Thr Thr Thr Thr Thr Ser Val Ser Cys Asn Tyr Leu Val
            420                 425                 430

<210> SEQ ID NO 17
<211> LENGTH: 22
<212> TYPE: DNA
<213> ORGANISM: Arabidopsis thaliana

<400> SEQUENCE: 17
atggaacgtg gagctccctt ct                                          22

<210> SEQ ID NO 18
<211> LENGTH: 23
```

<212> TYPE: DNA
<213> ORGANISM: Arabidopsis thaliana

<400> SEQUENCE: 18
ttcacttata ctgaccataa tgg                                            23

<210> SEQ ID NO 19
<211> LENGTH: 22
<212> TYPE: DNA
<213> ORGANISM: Arabidopsis thaliana

<400> SEQUENCE: 19
atggataact tcttaccctt tc                                             22

<210> SEQ ID NO 20
<211> LENGTH: 22
<212> TYPE: DNA
<213> ORGANISM: Arabidopsis thaliana

<400> SEQUENCE: 20
tcaccaccac tcaaagtcgt ta                                             22

<210> SEQ ID NO 21
<211> LENGTH: 20
<212> TYPE: DNA
<213> ORGANISM: Arabidopsis thaliana

<400> SEQUENCE: 21
atgaagaagc gcttaaccac                                                20

<210> SEQ ID NO 22
<211> LENGTH: 20
<212> TYPE: DNA
<213> ORGANISM: Arabidopsis thaliana

<400> SEQUENCE: 22
ctcagaccaa atagttacaa                                                20

<210> SEQ ID NO 23
<211> LENGTH: 24
<212> TYPE: DNA
<213> ORGANISM: Beta vulgaris

<400> SEQUENCE: 23
atgaccaatc acagcagcaa caac                                           24

<210> SEQ ID NO 24
<211> LENGTH: 24
<212> TYPE: DNA
<213> ORGANISM: Beta vulgaris

<400> SEQUENCE: 24
ttagttgtgg tgaccatatg gctc                                           24

<210> SEQ ID NO 25
<211> LENGTH: 25
<212> TYPE: DNA
<213> ORGANISM: Beta vulgaris

<400> SEQUENCE: 25
atgatgatga tggtggagga gagag                                          25

<210> SEQ ID NO 26

-continued

<211> LENGTH: 26
<212> TYPE: DNA
<213> ORGANISM: Beta vulgaris

<400> SEQUENCE: 26
tcaatagaag tcgtcaaggg acaaat                                           26

<210> SEQ ID NO 27
<211> LENGTH: 23
<212> TYPE: DNA
<213> ORGANISM: Beta vulgaris

<400> SEQUENCE: 27
atgaagaaga ggtcaattac taa                                              23

<210> SEQ ID NO 28
<211> LENGTH: 23
<212> TYPE: DNA
<213> ORGANISM: Beta vulgaris

<400> SEQUENCE: 28
ttacaattga catgagacta agc                                              23

<210> SEQ ID NO 29
<211> LENGTH: 24
<212> TYPE: DNA
<213> ORGANISM: Beta vulgaris

<400> SEQUENCE: 29
atggcgattt cggattcgcc tgag                                             24

<210> SEQ ID NO 30
<211> LENGTH: 25
<212> TYPE: DNA
<213> ORGANISM: Beta vulgaris

<400> SEQUENCE: 30
tcatgctaaa ttgcctttgc gattc                                            25

<210> SEQ ID NO 31
<211> LENGTH: 22
<212> TYPE: DNA
<213> ORGANISM: Beta vulgaris

<400> SEQUENCE: 31
gtattgtkag caactgggat ga                                               22

<210> SEQ ID NO 32
<211> LENGTH: 21
<212> TYPE: DNA
<213> ORGANISM: Beta vulgaris

<400> SEQUENCE: 32
aackytcagc ccratggtaa t                                                21

<210> SEQ ID NO 33
<211> LENGTH: 537
<212> TYPE: DNA
<213> ORGANISM: Cauliflower mosaic virus

<400> SEQUENCE: 33
atggagtcaa agattcaaat agaggaccta acagaactcg ccgtaaagac tggcgaacag      60
ttcatacaga gtctcttacg actcaatgac aagaagaaaa tcttcgtcaa catggtggag     120

```
cacgacacac ttgtctactc caaaaatatc aaagatacag tctcagaaga ccaaagggca      180
attgagactt ttcaacaaag ggtaatatcc ggaaacctcc tcggattcca ttgcccagct      240
atctgtcact ttattgtgaa gatagtggaa aaggaaggtg gctcctacaa atgccatcat      300
tgcgataaag gaaaggccat cgttgaagat gcctctgccg acagtggtcc caagatgga       360 cccccaccca cgaggagcat cgtggaaaaa gaagacgttc caaccacgtc ttcaaagcaa      420
gtggattgat gtgatatctc cactgacgta agggatgacg cacaatccca ctatccttcg      480 caagacccctt cctctatata aggaagttca tttcatttgg agagaacacg ggggact       537
```

```
<210> SEQ ID NO 34
<211> LENGTH: 20
<212> TYPE: DNA
<213> ORGANISM: Artificial Sequence
<220> FEATURE:
<223> OTHER INFORMATION: Synthesized

<400> SEQUENCE: 34
tcatttggag agaacacggg                                                   20

<210> SEQ ID NO 35
<211> LENGTH: 19
<212> TYPE: DNA
<213> ORGANISM: Artificial Sequence
<220> FEATURE:
<223> OTHER INFORMATION: Synthesized

<400> SEQUENCE: 35
aagaccggca acaggattc                                                    19

<210> SEQ ID NO 36
<211> LENGTH: 754
<212> TYPE: DNA
<213> ORGANISM: Beta vulgaris

<400> SEQUENCE: 36
cgtatcgtcg atagatttta caaaatttta tattgtatta gatttatcta aaatttccat       60
gttgtactct aaccttttaa acgttgcaaa atatctctat acacgatatg aaacagtgaa      120
ctttgagact ttcttaccct gtagacgtag agtaggattt ctgagccttg ttagttgact      180
gaggtttgag atataacttg agaaaataaa tgctaagtga ggtttggagt aggaatttct      240
attaataggg gtattttgtg tgatgtgtcg aaagtttagg ggaacgatct ataaaattca      300
aaaatgtcgg atgcaacata aaatttcata aaatacaaaa acaataggta gcacaaaaaa      360
tcataaaaat attagttgat tgccaaccaa caactcatcc taggtcatgt tttatacgca      420
acaaatgaat atttttatacc tcataaataa tatctatttg ttacatttaa aatgaaacgg      480
aggaagtatg ttgatgatga gcaatataaa actcttatat aattaaattc gcacgatgat      540
tgtatgctaa attgctaatc aattattgaa acgaaaagg gccccaagtgc ccatatgctt      600 aatttatgta cgatttaatt tcctccacta gcttgcatga ttttaaaacc agcatacaaa      660
ccttctataa atactagcat tcttcagcta ctaactctca tccccaacat ccctcaaaca      720
actatcagta acatacacac caaacaaaaa caac                                  754

<210> SEQ ID NO 37
<211> LENGTH: 739
<212> TYPE: DNA
<213> ORGANISM: Beta vulgaris
```

```
<400> SEQUENCE: 37 aagcttttc tcgtatcgtc gatagatttt acaaaattt  atattgtatt agatttatct      60
aaaatttcca tgttgtactc taacctttta aacgttgcaa aatatctcta tacacgatat     120
gaaacagtga actttgagac tttcttaccc tgtagacgta gagtaggatt tctgagcctt     180
gttagttgac tgaggtttga gatataactt gagaaaataa atgctaagtg aggtttggag     240
taggaatttc tattaatagg ggtattttgt gtgatgtgtc gaaagtttag gggaacgatc     300
tataaaattc aaaaatgtcg gatgcaacat aaaatttcat aaaatacaaa acaataggt      360
agcacaaaaa atcataaaaa tattagttga ttgccaacca caactcatc  ctaggtcatg     420
ttttatacgc aacaaatgaa tattttatac ctcataaata atatctattt gttacattta     480
aaatgaaacg gaggaagtat gttgatgatg agcaatataa aactcttata taattaaatt     540
cgcacgatga ttgtatgcta aattgctaat caattattga aaacgaaaag ggcccaagtg     600
cccatatgct taatttatgt acgatttaat ttcctccact agcttgcatg attttaaaac     660
cagcatacaa accttctata aatactagca ttcttcagct actaactctc atccccaaca     720
tccctcaaac aactatcag                                                  739

<210> SEQ ID NO 38
<211> LENGTH: 754
<212> TYPE: DNA
<213> ORGANISM: Beta vulgaris

<400> SEQUENCE: 38
cgtatcgtcg atagatttta caaaatttta tattgtatta gatttatcta aaatttccat     60
gttgtactct aaccttttaa acgttgcaaa atatctctat acacgatatg aaacagtaaa     120
ctttgagact ttcttaccct gtagacgtag agtaggattt ctgagccttg ttagttgact     180
gaggtttgag atgtaacttg agaaaataaa tgctaagtga ggtttggagt aggaatttct     240
attaataggg gtattttgtg tgatgtgtcg aaagtttagg ggaacgatct ataaaattca     300
aaaatgtcgg atgcaacata aaatttcata aaatacaaaa acaataggta gcacaaaaaa     360
tcataaaaat attagttgat tgccaaccaa caactcatcc taggtcatgt tttatacgca     420
acaaatgaat attttatacc tcataaataa tatctatttg ttacatttaa aataaaacgg     480
aggaagtatg ttgatgatga gcaatataaa actcttatat aattaaattc gcacgatgat     540
tgtatgctaa attgctaatc aattattgaa aacgaaaagg gcccaagtgc ccatatgctt     600
aatttatgta cgatttaatt tcctccactag cttgcatga ttttcaaacc agcatacaat     660
ccttctataa atactagcat tcttcatcta ctaactctca tccccaacat ccctcaaaca     720
actatcatca gtaacataca cagcaaacaa aaac                                 754

<210> SEQ ID NO 39
<211> LENGTH: 754
<212> TYPE: DNA
<213> ORGANISM: Beta vulgaris

<400> SEQUENCE: 39
cgtatcgtcg atagatttta caaaatttta tattgtatta gatttatcta aaatttccat     60
gttgtactct aaccttttaa acgttgcaaa atatctctat acacgatatg aaacagtaaa     120
ctttgagact ttcttaccct gtagacgtag agtaggattt ctgagccttg ttagttgact     180
gaggtttgag atgtaacttg agaaaataaa tgctaagtga ggtttggagt aggaatttct     240
attaataggg gtattttgtg tgatgtgtcg aaagtttagg ggaacgatct ataaaattca     300
```

```
aaaatgtcgg atgcaacata aaatttcata aaatacaaaa acaataggta gcacaaaaaa    360
tcataaaaat attagttgat tgccaaccaa caactcatcc taggtcatgt tttatacgca    420
acaaatgaat attttatacc tcataaataa tatctatttg ttacatttaa aatgaaacgg    480
aggaagtatg ttgatgatga gcaatataaa actcttatat aattaaattc gcacgatgat    540
tgtatgctaa attgctaatc aattattgaa aacgaaaagg gcccaagtgc ccatatgctt    600
aatttatgta cgatttaatt tcctccacta gcttgcatga ttttcaaacc agcatacaaa    660
ccttctataa atactagcat tcttcagcta ctaactctca tccccaacat ccctcaaaca    720
actatcagta acatacacac caaacaaaaa caac                                754

<210> SEQ ID NO 40
<211> LENGTH: 766
<212> TYPE: DNA
<213> ORGANISM: Beta vulgaris

<400> SEQUENCE: 40
aagcattttt ctcgtatcgt cgatagattt tacaaaattt tatattgtat tagatttatc     60
taaaatttcc atgttgtact ctaacctttt aaacgttgca aaatatctct atacacgata    120
tgaaacagtg aactttgaga cttcttaccc tgtagacgta gagtaggatt ttctgagcct    180
tgttagttga ctgaggtttg agatataact tgagaaaata atgctaagtg agggtttgga    240
gtaggaattt ctattaatag gggtattttg tgtgatgtgt cgaaagttta ggggaacgat    300
ctataaaatt caaaaatgtc ggatgcaaca taaaatttca taaatacaa aaacaatagg     360 tagcacaaaa aatcataaaa atattagttg attgccaacc aacaactcat cctaggtcat    420
gttttatacg caacaaatga atattttata cctcataaat aatatctatt tgttacattt    480
aaaatgaaac ggaggaagta tgttgatgat gagcaatata aaactcttat ataattaaat    540
tcgcacgatg attgtatgct aaattgctaa tcaattattg aaaacgaaaa gggcccaagt    600
gcccatatgc ttaatttatg tacgatttaa tttcctccac tagcttgcat gattttaaaa    660
ccagcataca aaccttctat aaatactagc attcttcagc tactaactct catccccaac    720
atccctcaaa caactatcag taacatacac accaaacaaa aacaac                    766

<210> SEQ ID NO 41
<211> LENGTH: 754
<212> TYPE: DNA
<213> ORGANISM: Beta vulgaris

<400> SEQUENCE: 41
cgtatcgtcg atagatttta caaaatttta tattgtatta gatttatcta aaatttccat     60
gttgtactct aaccttttaa acgttgcaaa atatctctat acacgatatg aaacagtgaa    120
ctttgagact tcttaccct gtagacgtag agtaggattt ctgagccttg ttagttgact    180
gaggtttgag atataacttg agaaaataa tgctaagtga ggtttggagt aggaatttct    240
attaataggg gtattttgtg tgatgtgtcg aaagtttagg ggaacgatct ataaaattca    300
aaaatgtcgg atgcaacata aaatttcata aatacaaaa acaataggta gcacaaaaa    360 tcataaaaat attagttgat tgccaaccaa caactcatcc taggtcatgt tttatacgca    420
acaaatgaat attttatacc tcataaataa tatctatttg ttacatttaa aatgaaacgg    480
aggaagtatg ttgatgatga gcaatataaa actcttatat aattaaattc gcacgatgat    540
tgtatgctaa attgctaatc aattattgaa aacgaaaagg gcccaagtgc ccatatgctt    600
```

-continued

```
aatttatgta cgatttaatt tcctccacta gcttgcatga ttttaaaacc agcatacaaa      660
ccttctataa atactagcat tcttcagcta ctaactctca tccccaacat ccctcaaaca      720
actatcagta acatacacac caaacaaaaa caac                                  754

<210> SEQ ID NO 42
<211> LENGTH: 770
<212> TYPE: DNA
<213> ORGANISM: Beta vulgaris

<400> SEQUENCE: 42
ataaagcatt tttcccgtat cgtcgaatag attttacaaa attttatatt gtattagatt       60
tatctaaaat ttccatgttg tactctaacc ttttaaacgt tgcaaaatat ctctatacac      120
gatatgaaac agtgaacttt gagactttct taccctgtag acgtagagta ggatttctga      180
gccttgttag ttgactgagg tttgagatat aacttgagaa aataaatgct aagtgaggtt      240
tggagtagga atttctatta ataggggtat tttgtgtgat gtgtcgaaag tttaggggaa      300
cgatctataa aattcaaaaa tgtcggatgc aacataaaat ttcataaaat acaaaaacaa      360
taggtagcac aaaaaatcat aaaaatatta gttgattgcc aaccaacaac tcatcctagg     420
tcatgtttta tacgcaacaa atgaatattt tatacctcat aaataatatc tatttgttac      480
atttaaaatg aaacggagga agtatgttga tgatgagcaa tataaaactc ttatataatt      540
aaattcgcac gatgattgta tgctaaattg ctaatcaatt attgaaaacg aaaagggccc     600
aagtgcccat atgcttaatt tatgtacgat ttaatttcct ccactagctt gcatgatttt     660
aaaaccagca tacaaacctt ctataaatac tagcattctt cagctactaa ctctcatccc     720
caacatccct caaacaacta tcagtaacat acacaccaaa caaaaacaac               770
```